US011369068B2

(12) United States Patent
Vilperte et al.

(10) Patent No.: US 11,369,068 B2
(45) Date of Patent: Jun. 28, 2022

(54) METHOD OF GENERATING PLANTS HAVING WHITE FOLIAGE

(71) Applicant: Klemm+Sohn GmbH & Co. KG, Stuttgart (DE)

(72) Inventors: Vinicius Vilperte, Hannover (DE); Thomas Debener, Wunstorf (DE); Robert Boehm, Winnenden (DE); Andrea Dohm, Pforzheim (DE); Guido Von Tubeuf, Stuttgart (DE); Ulrich Sander, Stuttgart (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 17/490,972

(22) Filed: Sep. 30, 2021

(65) Prior Publication Data
US 2022/0007605 A1 Jan. 13, 2022

Related U.S. Application Data

(63) Continuation of application No. 16/894,710, filed on Jun. 5, 2020, which is a continuation-in-part of application No. PCT/EP2019/064735, filed on Jun. 5, 2019.

(51) Int. Cl.
*A01H 3/04* (2006.01)
*A01H 6/38* (2018.01)
*A01H 5/02* (2018.01)
*C12N 9/10* (2006.01)
*A01H 1/04* (2006.01)
*A01H 1/06* (2006.01)
*A01H 5/12* (2018.01)
*C12N 15/82* (2006.01)

(52) U.S. Cl.
CPC .............. *A01H 3/04* (2013.01); *A01H 1/045* (2021.01); *A01H 1/06* (2013.01); *A01H 5/02* (2013.01); *A01H 5/12* (2013.01); *A01H 6/385* (2018.05); *C12N 9/1088* (2013.01); *C12N 15/825* (2013.01); *C12N 15/8213* (2013.01); *C12Y 205/01018* (2013.01)

(58) Field of Classification Search
CPC .................................................. C12N 9/1088
See application file for complete search history.

(56) References Cited

U.S. PATENT DOCUMENTS

| | | | |
|---|---|---|---|
| PP4,938 P | 11/1982 | Ecke, Jr. | |
| PP7,250 P | 6/1990 | Gutbier | |
| PP10,160 P | 12/1997 | Jacobsen | |
| 8,440,432 B2 | 5/2013 | Voytas et al. | |
| 8,450,471 B2 | 5/2013 | Voytas et al. | |
| PP23,786 P2 | 7/2013 | Klemm et al. | |
| 8,586,363 B2 | 11/2013 | Voytas et al. | |
| 8,586,526 B2 | 11/2013 | Gregory et al. | |
| 8,592,645 B2 | 11/2013 | DeKelver et al. | |
| 8,697,359 B1 | 4/2014 | Zhang | |
| 8,697,853 B2 | 4/2014 | Voytas et al. | |
| 8,704,041 B2 | 4/2014 | Gordon-Kamm et al. | |
| 8,771,945 B1 | 7/2014 | Zhang | |
| 8,871,445 B2 | 10/2014 | Cong et al. | |
| 8,889,418 B2 | 11/2014 | Zhang et al. | |
| 8,912,138 B2 | 12/2014 | Gregory et al. | |
| 8,921,112 B2 | 12/2014 | Cai et al. | |
| PP28,863 P3 * | 1/2018 | Snijder | A01H 6/38 Plt./304 |
| 2020/0383288 A1 | 12/2020 | Vilperte et al. | |

FOREIGN PATENT DOCUMENTS

CN 105936898 A 9/2016
WO WO-2005032242 A1 4/2005

OTHER PUBLICATIONS

Alfenito et al., "Functional Complementation of Anthocyanin Sequestration in the Vacuole by Widely Divergent Glutathione S-Transferases," Plant Cell 10, 1135-1149 (1998).
Altschul, S. et al., "Basic local alignment search tool", J Mol Biol (1990); 215(3):403-410.
Clarke et al., "Agrobacterium tumefaciens-mediated transformation of poinsettia, Euphorbia pulcherrima, with virus-derived hairpin RNA constructs confers resistance to Poinsettia mosaic virus," Plant Cell Rep 27(6):1027-1038 (2008).
Conn et al., "Purification, molecular cloning, and characterization of glutathione S-transferases (GSTs) from pigmented Vitis vinifera L. cell suspension cultures as putative anthocyanin transport proteins," J. Exp. Bot. 59(13):3621-3634 (2008).
Database EMBL [Online] Oct. 4, 2005 (Oct. 4, 2005), "CV03095B1 G07.f1 CV03-normalized library Euphorbia esula cDNA clone CV03095B1G07.f1 5, mRNA sequence.", XP002796731, retrieved from EBI accession No. EMBL:DV154667 Database accession No. DV154667, 2 pages.
Database UniProt [Online] Dec. 5, 2018 (Dec. 5, 2018), "RecName: Full=Glutathione transferase {ECO:0000256I ARBA:ARBA00012452}; EC=2.5.1.18 {ECO:0000256I ARBA:ARBA00012452};", retrieved from EBI accession No. UNIPROT:A0A2R6R622 Database accession No. A0A2R6R622, 2 pages.

(Continued)

*Primary Examiner* — David H Kruse
(74) *Attorney, Agent, or Firm* — Cooley LLP

(57) ABSTRACT

The disclosure relates to a method for the generation of plants, such as *Euphorbia pulcherrima*, having a dysfunctional glutathione S-transferase (GST), and the seeds, plant parts or plant cells derived therefrom. The disclosure further relates to a molecular marker capable of identifying a dysfunctional GST gene, to isolated DNA encoding such a dysfunctional GST gene and to the use of such DNA for the preparation of a molecular marker and for use in methods of targeted mutagenesis to inactivate the GST gene to generate plants with a white foliage phenotype.

10 Claims, 13 Drawing Sheets
Specification includes a Sequence Listing.

(56) References Cited

OTHER PUBLICATIONS

Dixon & Edwards, "Roles for Stress-inducible Lambda Glutathione Transferases in Flavonoid Metabolism in Plants as Identified by Ligand Fishing," J. Biol. Chem. 285, 36322-36329 (2010).
Examination Report No. 1 issued by the European Patent Office for Application No. 201786258, dated Jan. 25, 2021, 7 pages.
Examination Report No. 3 issued by the European Patent Office for Application No. 201786258, dated Sep. 29, 2021, 6 pages.
International Search Report and Written Opinion issued by the International Searching Authority for Application No. PCT/EP2019/064735, dated Jun. 24, 2020, 12 pages.
Kitamura et al., "Transparent Testa 19 Is Involved in the Accumulation of Both Anthocyanins and Proanthocyanidins in *Arabidopsis*," Plant J 37:104-114 (2004).
Larsen et al., "A carnation anthocyanin mutant is complemented by the glutathione S-transferases encoded by maize BZ2 and petunia AN9," Plant Cell Rep 21:900-904 (2003).
Li et al., "The *Arabidopsis* tt19-4 mutant differentially accumulates proanthocyanidin and anthocyanin through a 3' amino acid substitution in glutathione S-transferase," Plant Cell Environ. 34, 374-388 (2011).
Luo et al., "Reduced Anthocyanins in Petioles codes for a GST anthocyanin transporter that is essential for the foliage and fruit coloration in strawberry," Journal of Experimental Botany 69(10):2595-2608 (2018).
Marrs et al., "A glutathione S-transferase involved in vacuolar transfer encoded by the maize gene Bronze-2," Nature 375:397-400 (1995).
Needleman and Wunsch, "A General method applicable to the search for similarities in the Amino Acid Sequence of two proteins", Journal of Molecular Biology (1970); 48(3): 443-453.
Office Action issued by the European Patent Office for Application No. 20178625 dated May 11, 2021, 5 pages.
Pearson & Lipman, "Improved tools for biological sequence comparison," Proc. Natl. Acad. Sci. 85:2444-2448 (1988).
Potier, B., "Poplar Poinsettia Open House at UNH is Nov. 29-Dec. 1, 2012 LINH Today, No. 4094 (2012).
Response to Office Action issued by the European Patent Office for Application No. 20178625, dated Jul. 13, 2021, 13 pages.
Response to Office Action issued by the European Patent Office for Application No. 20178625, dated Mar. 26, 2021, 14 pages.
Schuelke, "An economic method for the fluorescent labeling of PCR fragments," Nature Biotechnol 18:233-234 (2000).
Silva et al., "Meganucleases and Other Tools for Targeted Genome Engineering: Perspectives and Challenges for Gene Therapy," Current Gene Therapy 11(1):11-27 (2011).
Smith et al.,"*Arabidopsis* AtGSTF2 is regulated by ethylene and auxin, and encodes a glutathione S-transferase that interacts with flavonoids," Plant J. 36, 433-442 (2003).
Smith, TF et al., 'Identification of Common Molecular Subsequences,' Journal of Molecular Biology, 147:195-197, PMID 7265238. doi:10.1016/0022-2836(81)90087-5, (1981).
Steinert et al., "Highly efficient heritable plant genome engineering using Cas9 orthologues from *Streptococcus thermophilus* and *Staphylococcus aureus*," Plant J. 84:1295-1305 (2015).
Stoddard et al., Homing endonucleases from mobile group I introns: discovery to genome engineering, Mobile DNA 5, (2014), 16 pages.
Sun et al., "*Arabidopsis* TT19 Functions as a Carrier to Transport Anthocyanin from the Cytosol to Tonoplasts," Mol. Plant 5, 387-400 (2012).
Vilperte et al., "Hybrid de novo transcriptome assembly of poinsettia (*Euphorbia pulcherrima* Willd. Ex Klotsch) bracts," BMC Genomics, 18 pages (2019).
Zhao, "Flavonoid Transport Mechanisms: How to Go, and With Whom," Trends Plant Sci 20(9):576-585 (2015).
Response to Office Action issued by the European Patent Office for Application No. 20178625, dated Nov. 17, 2021, 51 pages.

* cited by examiner

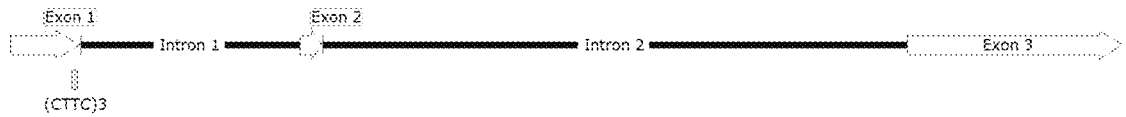

Euphorbia pulcherrima GST
2314 bp

Figure 1A

```
   1 AAAACTCTATAACAAACAAGAAATCAAGGCTAAAAAAATGGTAGTGAAAGTGTATGGAGC
  61 AGCTCAGGCAGCTTGCCCACAAAGAGTAATGGCCTGCCTTTTAGAGAAAGATATTCCTTT
 121 TGATCTTGTTCATGTTGATCTTCCTTCTGCTCAACATAAACTCTCTTCCTTCCTTCTCAA
 181 ACAGGTTCTTTACTTCCCTTTTTTTACTATACATTTCTTCTAGGCCTAATATACATCTAG
 241 ACCCCCTATAGTTGTTCCTGAAAACCCCTCAGCCCCCTGAACTTGTTAAAGTGGATCTTA
 301 CAGCCCCTTAAACTTGGTCAAACTGAACCTCAAAACCCCTTAATGGTAACATGCCCAGTT
 361 TTGTTCCGGTAAATCAGTTTTCGATTCAATCTTTGACGAAACAATCTTAGATTCAATCTT
 421 TAGAAAATAATACTTGACATATCAGCATCAAGCGGCTATGGGGTTCACTTTTAACAAGT
 481 TCAGGGTGCTATAAAGTCCACTTTAATAAATTCAGGGTTAAGGATACCTTTTGTAAGTTT
 541 AGGTGGTTGAGGGGTTTTAAGGGAACTATAGGAGGCCTAGATTTATTAGCTCTCTTGTTT
 601 GATGTCACAATTAATTATGTTTATTTATTTATTCTGTAGCCCTTTGGGTTAGTTCCAGCT
 661 ATAGAAGATGGGGATTTCAGGCTTTTTGGTATGTTTCTTAATCTTTTCATTTCAGTGATA
 721 GCCCTCAGTATTTCGTTTTACTAAGATTTCGGGACCACAATTCGTTTTTGTAGTGTCACT
 781 ATGGATAATTGTTAAAAATGAGACATGTACAAAACAAATCCTATTCGAATCTTCTATCGT
 841 TGGTCATAACCACATGGATATCTACGCATAAAAATACCAAAAAATATTTTAACATGTACA
 901 TGTTCTTTTGTATTCCGTCCACTATTTCGATAAGCATCGATTTATCGTTTTTGGCTTTA
 961 AATTATAATGGACTAAACTAAAATGATTCATTAAACTGTCTGAACTTCTTTATTGTGAAA
1021 TCACGGATAGCTGTTGCAACTCCACTTCAGGGTCAATTGGAAACAACATCTCTGTAATTA
1081 CATGGGTAAGGCTGCATACACTCAACCCCCCGACACTGCTTGTGAGGGAGCCTTATTAGG
1141 CATTGGGGTGATGTTGTTGTTTTACACGTTATTTTGTATCATTGTAATCTATCAAACTAT
1201 TATAATTACTTATTACCAAGTATAATTTATTACATTGATTAAAGTATAATTTATTCCACT
1261 AAATTTATGTTTTATGCACCTTACCCTGAACTTTGATTTTTTATTTAGTATTATAAAATG
1321 TTGTTTAAGTAAATAAAATAGATACTATTTAAAAATAATTTAGAAAAAAATAATAAAATA
1381 GAGCAAGGTCTCCATACAAAACCATCGTACTTATTTGAACAGATATATATGTAGTGTTAT
1441 TCATATTTTTTTTATAATAACATAGAACTGATGAATCTGGATTAGAAATGATGATATAA
1501 TGGCTTGCCTCATTCACGATCACACAATTGATAAGTCTGATTTTACCAACAAATATCAGT
1561 TTTTCAATATTATGTGTTGCTATTTTCTTGAAGAAGAAATTTTGCACGACCATATTTAAG
1621 AATAGGCTTAGATTGATCGGTCAAACAAATCTTAGGTTATTTTTTCATTTTCCTTTTCT
1681 CATTAGTTAGAATCAAAATTTGGAATTAAATTTTTTGTTTTAATTTTACTTCTAACTATT
1741 GAGATCATATATCACCAAATATATGCTTTCTTTATTATTTCTACATAAAAAAATATATGG
1801 TTTTACAACTACCTAACTATGCTTTTTTTTAAAGTTTGCCTCATTAGGCTTACAACTACC
1861 AAACTATGTTGAATTAATATAATTTTGTTTGTGTGTGTGAAGAATCAAGAGCCATAATGA
1921 GATACTATGCAACAAAATATGAAGAAAGAGGGCCCAATTTGTTAGGAAAAACATTAGAAG
1981 AGAAAGCAATAGTTGATCAATGGGTTGAAGTGGAAGCCCATAATTTCAATAATTTGGTTT
2041 ACAATATTGTAATTGAAGTTTTGATAAAGCCAAAAATGGGGGAACAAGGTGACATCAACA
2101 TAGTCAAAAGCTGTGAACATAAGCTGGATAAAGTGTTCGATGTGTACGAGGAAAGGCTAT
2161 CCAGTTCCAAATATCTTGGAGGAGATTATTTCACACTTGCTGATTTAACCCATATGCCTT
2221 CCATTAGGTACCTTGTTCATGAGCTTGGGTTAGCCCATTTGGTTCACAATAGAAACAAGG
2281 TCAATGCTTGGTGGATTGATATATCGGACCGACCGGCTTGGAAAAATTTGATGATTCTTG
2341 CTGGTTATTAG
```

Figure 1B

METHOD OF GENERATING PLANTS HAVING WHITE FOLIAGE

CROSS REFERENCE TO RELATED APPLICATION

This application is a continuation of U.S. application Ser. No. 16/894,710 filed on Jun. 5, 2020, which is a continuation-in-part of and claims the benefit of priority to: PCT Application No. PCT/EP2019/064735 filed on Jun. 5, 2019, the entire contents of which are incorporated herein by reference for all purposes.

SUBMISSION OF SEQUENCE LISTING

The contents of the text file submitted electronically herewith are incorporated herein by reference in their entirety: A computer readable format copy of the Sequence Listing (file name: SELE_001_02US_SubSeqList_ST25.txt.; date recorded: Aug. 11, 2020; file size: 65 kb).

BACKGROUND

Poinsettia is particularly well known for its red and green foliage and is widely used in Christmas floral displays. The coloured bracts, which are most often flaming red but can be orange, pale green, cream, pink, white, or marbled, are often mistaken for flower petals because of their groupings and colours but are actually leaves. The colouration of the bracts is triggered by photoperiodism, meaning that they require short day conditions (12 hours at a time for at least five days in a row) to change colour. At the same time, the plants require abundant light during the day for the brightest colour.

Breeding of new plant varieties requires the continuous development of genetic diversity to obtain new, improved characteristics and traits. New genetic diversity can be established by crossing, random mutagenesis, or with the help of modern biotechnology.

The foregoing examples of the related art and limitations related therewith are intended to be illustrative and not exclusive. Other limitations of the related art will become apparent to those of skill in the art upon a reading of the specification.

SUMMARY

The present disclosure relates to a method for the generation of a *Euphorbia pulcherrima* (Poinsettia) plant having a having a white foliage phenotype comprising the steps of: a. providing a target *E. pulcherrima* plant without a white foliage phenotype comprising in its genome at least one functional allele of a glutathione S-transferase gene (EpGST) comprising a simple sequence repeat (SSR) in the region encoding amino acids at positions 40-50 of the protein of SEQ ID NO: 3, comprising a stretch of 12 nucleotides consisting of a threefold CTTC repeat; b. subjecting said *E. pulcherrima* plant to a mutagenesis treatment to produce a mutant *E. pulcherrima* plant; c. selecting a mutant *E. pulcherrima* plant, wherein at least one allele of the EpGST gene comprises a CTTC deletion in said SSR motif; d. repeating steps b. and c. until all alleles of the EpGST gene in the plant genome comprise said CTTC deletion in said SSR motif; and e. selecting a *E. pulcherrima* plant having a white foliage phenotype, wherein said plant is homozygous for said CTTC deletion in said SSR motif.

In some embodiments, the present disclosure teaches a method for the generation of *E. pulcherrima* plants having a white foliage phenotype further comprising propagating said *E. pulcherrima* plant being homozygous for the EpGST gene comprising said CTTC deletion in said SSR motif and/or crossing said *E. pulcherrima* plant being homozygous for the EpGST gene comprising said CTTC deletion in said SSR motif with another *Euphorbia* sp. plant.

In some embodiments, the present disclosure teaches a method wherein said mutant *E. pulcherrima* plants without a white foliage phenotype are selected by a molecular marker suitable for the detection of said CTTC deletion in said SSR motif of the EpGST gene.

In some embodiments, the present disclosure teaches a method wherein the mutagenesis treatment is a human-induced random mutagenesis treatment selected from the group consisting of agents which cause a DNA double-strand break, ultraviolet (UV) irradiation, hydroxylamine, N-methyl-N'-nitro-N-nitrosoguanidine (MNNG), O-methyl hydroxylamine, nitrous acid, ethyl methane sulphonate (EMS), sodium bisulphite, formic acid, and nucleotide analogues.

In some embodiments, the present disclosure teaches a method wherein the functional EpGST gene in said target *E. pulcherrima* is selected from the group consisting of: a. A EpGST gene encoding the protein of SEQ ID NO: 3 and functional homologs or variants thereof having at least 60%, amino acid identity to SEQ ID NO: 3, wherein said homologs or variants have a first domain at positions 11-13 of SEQ ID NO: 3 being AAC, AGC or AAN, where N can be any amino acid (SEQ ID NO: 62), a second domain at positions 53-56 of SEQ ID NO: 3 being LVPA, QVPA (SEQ ID NO: 63) or QPVP (SEQ ID NO: 64) and a third amino acid domain at positions 65-68 of SEQ ID NO: 3 being FESR, b. A gene encoding an mRNA corresponding to the cDNA of SEQ ID NO: 2 and functional homologs or variants thereof having at least 90% nucleotide identity to SEQ ID NO: 2, wherein said homologs or variants comprises a stretch of 12 nucleotides consisting of a threefold CTTC repeat in the region of positions 118-150 of SEQ ID NO: 2, c. the EpGST gene of SEQ ID NO: 1 and functional homologs or variants thereof having at least 90% nucleotide identity to SEQ ID NO: 1, wherein said homolog or variant comprises a stretch of 12 nucleotides consisting of a threefold CTTC repeat in the region of positions 128-139 of SEQ ID NO: 1, and d. the EpGST gene of SEQ ID NO: 61 and functional homologs or variants thereof having at least 90% nucleotide identity to SEQ ID NO: 61, wherein said homolog or variant comprises a stretch of 12 nucleotides consisting of a threefold CTTC repeat in the region of positions 155-187 of SEQ ID No 61.

In some embodiments, the present disclosure teaches a method wherein the functional homolog or variant of the protein of SEQ ID NO: 3 further has at least one of a V on position 2 of SEQ ID NO: 3, a F or an L on position 62 of SEQ ID NO: 3, a LE on positions 90-91 of SEQ ID NO: 3, and an S on position 153 of SEQ ID NO: 3.

In some embodiments, the present disclosure relates to a plant or plant part having white foliage produced by the method disclosed herein, wherein said plant has all of the essential morphological and physiological traits of the target *E. pulcherrima* plant.

In some embodiments, the present disclosure teaches a white-foliaged *E. pulcherrima* plant derived from a non-white foliaged cultivated *E. pulcherrima* plant, wherein said non-white plant comprises in its genome a gene encoding a homolog or variant having at least 60% amino acid identity to SEQ ID NO: 3, said homolog or variant having a SSR comprising a stretch of 12 nucleotides consisting of a threefold CTTC repeat at positions 40-50 of the protein of SEQ ID NO: 3, wherein said derived white-foliaged *E. pulcherrima* plant comprises a CTTC deletion in said SSR, and wherein said white-foliaged *E. pulcherrima* plant is at least 99.9% genetically identical to said non-white foliaged *E. pulcherrima* plant.

In some embodiments, the present disclosure relates to white-foliaged *E. pulcherrima* plants, wherein said derived from non-white foliaged cultivated *E. pulcherrima* plant comprises in its genome a first domain at positions 11-13 of SEQ ID NO: 3 being AAC, AGC or AAN, where N can be any amino acid (SEQ ID NO: 62), a second domain at positions 53-56 of SEQ ID NO: 3 being LVPA, QVPA (SEQ ID NO: 63) or QPVP (SEQ ID NO: 64), and a third amino acid domain at positions 65-68 of SEQ ID NO: 3 being FESR.

In some embodiments, the present disclosure relates to seeds, plant parts, plant cells, or a plant population of a white-foliage *E. pulcherrima* plant derived from a non-white-foliage *E. pulcherrima* plant.

In some embodiments, the present disclosure teaches a method for the generation of a *E. pulcherrima* plant having a white foliage phenotype comprising the steps of: a. providing a target *E. pulcherrima* plant without a white foliage phenotype comprising in its genome at least one dysfunctional allele of EpGST and one functional allele of EpGST; b. subjecting said *E. pulcherrima* plant to a mutagenesis treatment to produce a mutant *E. pulcherrima* plant; c. selecting a mutant *E. pulcherrima* plant having white foliage and wherein at least one allele of the EpGST gene comprises a CTTC deletion in the region encoding amino acids at positions 40-50 of the protein of SEQ ID NO: 3.

In some embodiments, the present disclosure teaches a method further comprising propagating said *E. pulcherrima* plant having at least one allele of EpGST comprising said CTTC deletion and/or crossing said *E. pulcherrima* plant having at least one allele of EpGST comprising said CTTC deletion with another *Euphorbia* sp. plant.

In some embodiments, the present disclosure teaches a method wherein said mutant *E. pulcherrima* plants having white foliage are selected by a molecular marker suitable for the detection of said CTTC deletion in the EpGST gene.

In some embodiments, the present disclosure teaches a method of generating a *E. pulcherrima* plant with a white foliage phenotype, wherein said plant is derived from a white foliaged plant as first donor plant by breeding technologies with one or more non-white foliaged second donor *E. pulcherrima* plants comprising one or more elite properties, wherein said derived plant comprises one or more elite properties from the one or more second donor plants.

In some embodiments, the present disclosure relates to isolated nucleic acid of the EpGST gene described by SEQ ID NO: 61 or a variant thereof having at least 80% identity to the sequence described by SEQ ID NO: 1 and encoding a functional homolog or variant of the protein of SEQ ID NO: 3, wherein said homolog or variant has a first domain at positions 11-13 of SEQ ID NO: 3 being AAC, AGC or AAN, where N can be any amino acid (SEQ ID NO: 62), a second domain at positions 53-56 of SEQ ID NO: 3 being LVPA, QVPA (SEQ ID NO: 63) or QPVP (SEQ ID NO: 64), and a third amino acid domain at positions 65-68 of SEQ ID NO: 3 being FESR, and further comprising, in the region encoding amino acids at positions 40-50 of the protein of SEQ ID NO: 3, a stretch of 12 nucleotides consisting of a threefold CTTC repeat.

In some embodiments, the present disclosure teaches a method of use of the isolated nucleic acid for the preparation of a molecular marker or for a method for targeted mutagenesis of said EpGST gene.

In some embodiments, the present disclosure relates to isolated nucleic acid selected from the group consisting of SEQ ID NO: 44, SEQ ID NO: 45, SEQ ID NO: 46, SEQ ID NO: 47, SEQ ID NO: 48, SEQ ID NO: 49, or variants thereof with at least 95% identity.

In some embodiments, the present disclosure teaches a method wherein a continuous stretch of at least 17 nucleotides from any of the isolated DNA sequences is used to produce a guide RNA or an expression construct therefore for a CRISPR/Cas-based method of gene editing or to produce a silencing RNA or an expression construct therefore for a method of RNA-mediated gene silencing.

In some embodiments, the present disclosure teaches a method wherein the targeted mutagenesis is introduced by a DNA modification enzyme selected from the group consisting of meganucleases (MNs), zinc-finger nucleases (ZFNs), transcription-activator like effector nucleases (TALENs), Cas9 nuclease, Cpf1 nuclease (Cas12a), dCas9-FokI, dCpf1-FokI, chimeric Cas9-cytidine deaminase, chimeric Cas9-adenine deaminase, chimeric FEN1-FokI, and Mega-TALs, a nickase Cas9 (nCas9), chimeric dCas9 non-FokI nuclease, dCpf1 non-FokI nuclease, chimeric Cpf1-cytidine deaminase, and Cpf1-adenine deaminase.

In some embodiments, the present disclosure teaches a method wherein the DNA sequence used to design a guide RNA is an 18-21 nucleotide sequence and is at least 90% identical to a target sequence.

In some embodiments, the present disclosure teaches a method wherein the target sequence is SEQ ID: 61.

In some embodiments, the present disclosure teaches a method of use of the isolated nucleic acid disclosed herein for the generation of a molecular marker, wherein said marker is capable of identifying a dysfunctional EpGST allele.

In some embodiments, the present disclosure relates to molecular markers which identify a CTTC deletion within positions 128-139 of the EpGST gene of SEQ ID NO: 1.

In some embodiments, the present disclosure teaches a method for producing a *E. pulcherrima* plant having a white foliage phenotype comprising: Screening a population of *E. pulcherrima* plants for dysfunctional GST using the markers disclosed herein; Selecting a first *E. pulcherrima* plant having at least one dysfunctional GST allele; Crossing said first selected *E. pulcherrima* plant having at least one dysfunctional GST allele with a second *E. pulcherrima* plant having at least one dysfunctional GST allele or itself to produce $F_1$ progeny; and Screening said $F_1$ progeny *E. pulcherrima* plants using said marker for homozygous dysfunctional GST alleles.

In some embodiments, the present disclosure relates to plants or plant parts having white foliage produced by marker-assisted breeding.

In some embodiments, the present disclosure relates to a method of use of the isolated DNA as described above as well as the sequences of SEQ ID NO: 44 to 49, or variants with at least 95% identity therewith for the preparation of a molecular marker as described above or for a method for targeted mutagenesis of a GST gene in a target plant.

In some embodiments, the present disclosure relates to a molecular marker or method of targeted mutatgenesis comprising continuous stretch of at least 17 nucleotides from any isolated DNA sequences disclosed herein to (a) produce a guide RNA or an expression construct therefor for a CRISPR/Cas-based method of gene editing or (b) produce a silencing RNA or an expression construct therefor for a method of RNA-mediated gene silencing.

In some embodiments, the present disclosure also teaches a method for the production of plants having a reduced level of anthocyanins comprising the steps of: a. providing a plant comprising in its genome at least one functional copy of a glutathione S-transferase GST gene encoding a protein selected from the group consisting of SEQ ID NO: 3, and 53 to 59 or encoding a functional homolog or variant of said protein with at least 60%, amino acid identity, the homolog or variant having a first domain corresponding to positions 11-13 of SEQ ID NO: 3 being AAC, AGC or AAN, where N can be any amino acid (SEQ ID NO: 62), a second domain corresponding to positions 53-56 of SEQ ID NO: 3 being LVPA, QVPA (SEQ ID NO: 63) or QPVP (SEQ ID NO: 64), and a third amino acid domain corresponding to positions 65-68 of SEQ ID NO: 3 being FESR; b. subjecting the plant of step a. to targeted mutagenesis treatment to produce a mutant GST gene therein, and c. selecting a plant with reduced level of anthocyanins being homozygous for mutated GST gene.

In some embodiments, the present disclosure relates to mutations in the GST gene, wherein the mutations are selected from the group consisting of a loss-of-function mutation, a partial loss-of-function mutation, a restored frameshift mutation, an in-frame deletion mutation, or a promoter deletion.

In some embodiments, the present disclosure teaches a method of GST mutagenesis involving the use of at least one DNA sequence selected from the group consisting of: (i) the sequences of any of the claims 11-13, (ii) the sequences of SEQ ID NO: 44 to 49, or variants thereof with at least 95% identity, (iii) the complements to the sequences under (i) and (ii), and (iv) a fragment of the sequences under (i) to (iii) of at least 17 contiguous nucleotides, wherein said DNA sequence is used to produce a guide RNA targeting GST.

In some embodiments the present disclosure teaches a method of GST mutagenesis in a target plant, wherein the target plant is a variety of red wine (*Vitis vinifera*) and wherein the target plant is converted into a white wine variety while otherwise retaining all its other essential characteristics.

In some embodiments, the present disclosure teaches a method for producing a plant having reduced levels of anthocyanins comprising: a. Providing a plant comprising in its genome at least one functional allele of a glutathione S-transferase gene; b. subjecting said plant to targeted mutagenesis treatment to produce a mutant GST gene therein, wherein said mutation is selected from the group consisting of loss-of-function, partial loss-of-function, a restored frameshift, an in-frame deletion, or a promoter deletion, and wherein said targeted mutagenesis uses at least one of the sequences of SEQ ID NO: 44-49, or variants thereof having at least 95% identity, to produce a guide RNA; and; c. selecting a plant having reduced levels of anthocyanins.

The following embodiments and aspects thereof are described and illustrated in conjunction with products and methods, which are meant to be exemplary and illustrative, not limiting in scope.

BRIEF DESCRIPTION OF THE SEQUENCE LISTINGS

SEQ ID NO: 1 discloses the wild type EpGST nucleotide sequence.

SEQ ID NO: 2 discloses the corresponding coding sequence of EpGST.

SEQ ID NO: 3 discloses the amino acid sequence of the EpGST protein.

SEQ ID NO: 4 discloses a forward amplification primer designated "F1" for the full length EpGST gene.

SEQ ID NO: 5 discloses a reverse amplification primer designated "R1" for the full length EpGST gene.

SEQ ID NO: 6 discloses a forward amplification primer designated "F2" for an intronic region of the EpGST gene.

SEQ ID NO: 7 discloses a reverse amplification primer designated "R2" for an intronic region of the EpGST gene.

SEQ ID NO: 8 discloses a reverse amplification primer designated "R3" for an intronic region of the EpGST gene.

SEQ ID NO: 9 discloses a forward amplification primer as shown in FIG. 2.

SEQ ID NO: 10 discloses a reverse amplification primer as shown in FIG. 2.

SEQ ID NO: 11 discloses a forward amplification primer designated "M13(−21)".

SEQ ID NO: 12 discloses a reverse amplification primer designated "Cas9-R".

SEQ ID NO: 13 discloses the wildtype EpGST coding sequence of 'Christmas Feelings'.

SEQ ID NO: 14 discloses the wildtype EpGST coding sequence of 'Christmas Glory'.

SEQ ID NO: 15 discloses the wildtype EpGST coding sequence of 'Christmas Joy'.

SEQ ID NO: 16 discloses the wildtype EpGST coding sequence of 'Titan Red'.

SEQ ID NO: 17 discloses the wildtype EpGST coding sequence of 'Bravo Bright Red'.

SEQ ID NO: 18 discloses the wildtype EpGST coding sequence of 'SK130'.

SEQ ID NO: 19 discloses the mutant EpGST coding sequence of 'Christmas Feelings White'.

SEQ ID NO: 20 discloses the mutant EpGST coding sequence of 'Christmas Glory White'.

SEQ ID NO: 21 discloses the mutant EpGST coding sequence of 'Christmas Joy White'.

SEQ ID NO: 22 discloses the mutant EpGST coding sequence of 'Titan White'.

SEQ ID NO: 23 discloses the mutant EpGST coding sequence of 'Bravo White'.

SEQ ID NO: 24 discloses the mutant EpGST coding sequence of 'SK130 White'.

SEQ ID NO: 25 discloses the mutant EpGST coding sequence of PRINCETTIA® 'Pearl'.

SEQ ID NO: 26 discloses the mutant EpGST coding sequence of PRINCETTIA® 'Pure White'.

SEQ ID NO: 27 discloses the mutant EpGST coding sequence of 'Alaska'.

SEQ ID NO: 28 discloses the mutant EpGST coding sequence of 'Alpina'.

SEQ ID NO: 29 discloses the mutant EpGST coding sequence of 'SK158'.

SEQ ID NO: 30 discloses the mutant EpGST coding sequence of 'Christmas Beauty White'.

SEQ ID NO: 31 discloses the mutant EpGST coding sequence of PRINCETTIA® 'Dark Pink'.

SEQ ID NO: 32 discloses the mutant EpGST coding sequence of PRINCETTIA® 'Hot Pink'.

SEQ ID NO: 33 discloses the mutant EpGST coding sequence of PRINCETTIA® 'Pink'.

SEQ ID NO: 34 discloses the mutant EpGST coding sequence of PRINCETTIA® 'Soft Pink'.

SEQ ID NO: 35 discloses the mutant EpGST coding sequence of 'Premium'.

SEQ ID NO: 36 discloses the mutant EpGST coding sequence of 'Freedom'.

SEQ ID NO: 37 discloses the mutant EpGST coding sequence of 'Otto'.

SEQ ID NO: 38 discloses the mutant EpGST coding sequence of 'Christmas Season'.

SEQ ID NO: 39 discloses the mutant EpGST coding sequence of 'Christmas Beauty'.

SEQ ID NO: 40 discloses the mutant EpGST coding sequence of 'SK158 Red'.

SEQ ID NO: 41 discloses a mutant EpGST coding sequence of SEQ ID NO: 2 comprising a CTTC deletion in the region 128-139 therein.

SEQ ID NO: 42 discloses a related GST from AtTT19 (*Arabidopsis thaliana*—NM_121728.4.

SEQ ID NO: 43 discloses a related GST from AtGSTF11 (*Arabidopsis thaliana*—NM111189.3_

SEQ ID NO: 44 discloses a related GST from PhAN9 (*Petunia hybrida*—Y07721.1).

SEQ ID NO: 45 discloses a related GST from CkmGST3 (*Cyclamen persicum* x *Cyclamen purpurascens*—AB682678.1).

SEQ ID NO: 46 discloses a related GST from VvGST4 (*Vitis vinifera*—AY971515.1).

SEQ ID NO: 47 discloses a related GST from LcGST4 (*Litchi chinensis*—KT946768.1).

SEQ ID NO: 48 discloses a related GST from PpRiant1 (*Prunus persica*—KT312847.1).

SEQ ID NO: 49 discloses a related GST from PpRiant2 (*Prunus persica*—KT312848.1).

SEQ ID NO: 50 discloses the amino acid sequence of a C-truncated mutant dysfunctional protein as a result of the CTTC deletion on positions 136-139 of the CDNA of SEQ ID No 2, resulting in a frame shifted stop codon at positions 158-160.

SEQ ID NO: 51 discloses the amino acid sequence of an N-truncated mutant dysfunctional protein as a result of the CTTC deletion on positions 136-139 of the CDNA of SEQ ID No 2, resulting in a new in-frame start codon at positions 211-213.

SEQ ID NO: 52 discloses the corresponding amino acid sequence of SEQ ID NO: 42 from AtTT19 (*Arabidopsis thaliana*—NM_121728.4.)

SEQ ID NO: 53 discloses the corresponding amino acid sequence of SEQ ID NO: 43 from AtGSTF11 (*Arabidopsis thaliana*—NM111189.3).

SEQ ID NO: 54 discloses the corresponding amino acid sequence of SEQ ID NO: 44 from PhAN9 a related GST from *Petunia hybrida* Y07721.1.

SEQ ID NO: 55 discloses the corresponding amino acid sequence of SEQ ID NO: 45 from CkmGST3 (*Cyclamen persicum* x *Cyclamen purpurascens*—AB682678.1).

SEQ ID NO: 56 discloses the corresponding amino acid sequence of SEQ ID NO: 46 from VvGST4 (*Vitis vinifera*—AY971515.1).

SEQ ID NO: 57 discloses the corresponding amino acid sequence of SEQ ID NO: 47 from LcGST4 (*Litchi chinensis*—KT946768.1).

SEQ ID NO: 58 discloses the corresponding amino acid sequence of SEQ ID NO: 48 from PpRiant1 (*Prunus persica*—KT312847.1).

SEQ ID NO: 59 discloses the corresponding amino acid sequence of SEQ ID NO: 49 from PpRiant2 (*Prunus persica*—KT312848.1).

SEQ ID NO: 60 discloses a forward amplification primer designated "Ft".

SEQ ID NO: 61 discloses the genomic DNA of the wild type EpGST gene including a 5'UTR stretch of 37 nucleotides.

SEQ ID NO: 62 discloses a variant amino acid sequence of SEQ ID NO: 3.

SEQ ID NO: 63 discloses the amino acid sequence of a QVPA variant in the second domain at positions 53-56 of SEQ ID NO: 3.

SEQ ID NO: 64 discloses the amino acid sequence of a QPVP variant in the second domain at positions 53-56 of SEQ ID NO: 3.

BRIEF DESCRIPTION OF THE DRAWINGS

The accompanying figures, which are incorporated herein and form a part of the specification, illustrate some, but not the only or exclusive, example embodiments and/or features. It is intended that the embodiments and figures disclosed herein are to be considered illustrative rather than limiting.

FIG. 1A is a schematic representation of the full-length sequence (2314 bp) of the *Euphorbia pulcherrima* GST gene (EpGST) as depicted in SEQ ID NO: 1.

FIG. 1B shows the corresponding genomic gene sequence as depicted in SEQ ID NO: 61.

FIGS. 6A-1 to 6A-4 represent a CLUSTALW sequence alignment of the coding nucleotide sequences from GST genes of different species. Both wild type (SEQ ID NO: 2) and mutated (SEQ ID NO: 41) (first and second row, respectively) with known anthocyanin-related GST genes from other plant species: AtGSTF11 (SEQ ID NO: 43), AtTT19 (SEQ ID NO: 42), PhAN9 (SEQ ID NO: 44), CkmGST3 (SEQ ID NO: 45), VvGST4 (SEQ ID NO: 46), LcGST4 (SEQ ID NO: 47), PpRiant1 (SEQ ID NO: 48) and PpRiant2 (SEQ ID NO: 49) (rows 3-10, respectively). The CTTC$_3$ SSR locus is marked above the alignment. Conserved sequences among all the genes are shown with a grey background. Sequences encoding anthocyanin binding domains are indicated in boxes.

FIGS. 7A-1 to A-3 represent a CLUSTALW amino acid sequence alignment of the EpGST gene (SEQ ID NO: 3), an EpGST mutation in ORF1 (SEQ ID NO: 50), an EpGST mutation in ORF2 (SEQ ID NO: 51), and known anthocyanin-related GST genes from other plant species: AtGSTF11 (SEQ ID NO: 53), AtTT19 (SEQ ID NO: 52), PhAN9 (SEQ ID NO: 54), CkmGST3 (SEQ ID NO: 55), VvGST4 (SEQ ID NO: 56), LcGST4 (SEQ ID NO: 57), PpRiant1 (SEQ ID NO: 58) and PpRiant2 (SEQ ID NO: 59) (rows 4-11, respectively). Conserved sequences among all the genes are shown with a grey background. Anthocyanin binding domains are indicated in boxes.

FIG. 7B shows a phylogenetic tree (Constructed Neighbour-Joining tree) of the EpGST amino acid sequence with known anthocyanin-related genes. Bootstrap values were calculated from 1000 replicate analyses and are shown under the tree branches.

DEFINITIONS

Figure 2:
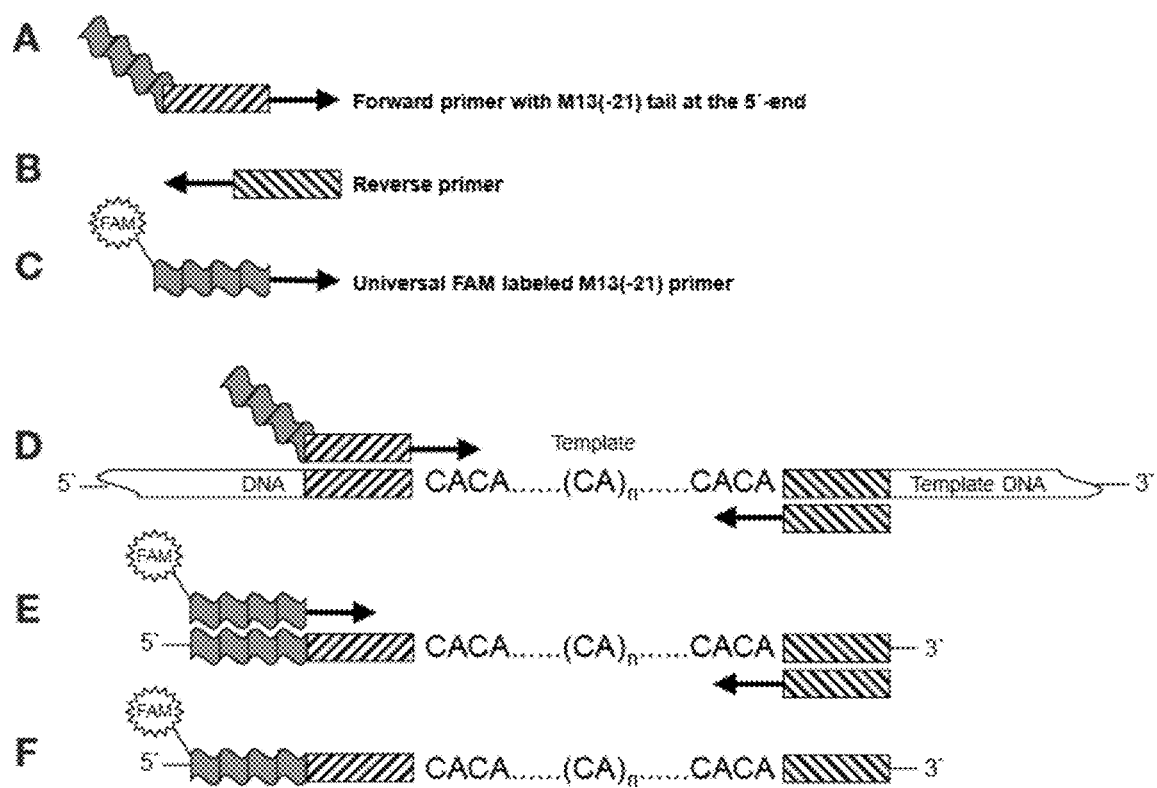
FIG. 2 is an amplification scheme for the fluorescent labelling of PCR fragments. The hatched boxes indicate the deletion-specific primers, the undulating grey box indicates the universal M13(-21) sequence, and the star the fluorescent FAM label.

While the following terms are believed to be well understood by one of ordinary skill in the art, the following definitions are set forth to facilitate explanation of the presently disclosed subject matter.

All technical and scientific terms used herein, unless otherwise defined below, are intended to have the same meaning as commonly understood by one of ordinary skill in the art. References to techniques employed herein are intended to refer to the techniques as commonly understood in the art, including variations on those techniques and/or substitutions of equivalent techniques that would be apparent to one of skill in the art.

Following long-standing patent law convention, the terms "a," "an," and "the" refer to "one or more" when used in this application, including the claims. For example, the phrase "a cell" refers to one or more cells, and in some embodiments can refer to a tissue and/or an organ. Similarly, the phrase "at least one", when employed herein to refer to an entity, refers to, for example, 1, 2, 3, 4, 5, 6, 7, 8, 9, 10, 15, 20, 25, 30, 35, 40, 45, 50, 75, 100, or more of that entity, including but not limited to all whole number values between 1 and 100 as well as whole numbers greater than 100.

Unless otherwise indicated, all numbers expressing quantities of ingredients, reaction conditions, and so forth used in the specification and claims are to be understood as being modified in all instances by the term "about." The term "about," as used herein when referring to a measurable value such as an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods and/or employ the discloses compositions, nucleic acids, polypeptides, etc. Accordingly, unless indicated to the contrary, the numerical parameters set forth in this specification and attached claims are approximations that can vary depending upon the desired properties sought to be obtained by the presently disclosed subject matter.

As used herein, the term "and/or" when used in the context of a list of entities, refers to the entities being present singly or in combination. Thus, for example, the phrase "A, B, C, and/or D" includes A, B, C, and D individually, but also includes any and all combinations and subcombinations of A, B, C, and D (e.g., AB, AC, AD, BC, BD, CD, ABC, ABD, and BCD). In some embodiments, one of more of the elements to which the "and/or" refers can also individually be present in single or multiple occurrences in the combinations(s) and/or subcombination(s).

As used herein, the phrase "associated with" refers to a recognizable and/or assayable relationship between two entities. For example, a marker is "associated with" a trait when it is linked to it and when the presence of the marker is an indicator of whether and/or to what extent the desired trait or trait form will occur in a plant/germplasm comprising the marker. Similarly, a marker is "associated with" an allele when it is linked to it and when the presence of the marker is an indicator of whether the allele is present in a plant/germplasm comprising the marker. For example, "a marker associated with EpGST gene" or the "CTTC deletion" refers to a marker whose presence or absence can be used to predict whether a plant is homozygous or heterozygous for the functional or dysfunctional EpGST gene.

As used herein, the term "human-induced mutation" refers to any mutation that occurs as a result of either direct or indirect human action. This term includes, but is not limited to, mutations obtained by any method of targeted or human-induced random mutagenesis.

As used herein, the term "nucleotide sequence identity" refers to the presence of identical nucleotides at corresponding positions of two polynucleotides. Readily available sequence comparison and multiple sequence alignment algorithms are, respectively, the Basic Local Alignment Search Tool (BLAST) and ClustalW/ClustalW2/Clustal Omega programs available on the Internet (e.g., the website of the EMBL-EBI). Other suitable programs include, but are not limited to, GAP, BestFit, Plot Similarity, and FASTA, which are part of the Accelrys GCG Package available from Accelrys, Inc. of San Diego, Calif., United States of America. See also Smith & Waterman, 1981; Needleman & Wunsch, 1970; Pearson & Lipman, 1988; Ausubel et al., 1988; and Sambrook & Russell, 2001. One example of an algorithm that is suitable for determining percent sequence identity and sequence similarity is the BLAST algorithm, which is described in Altschul et al., 1990. Unless otherwise noted, alignments disclosed herein utilized ClustalW.

As used herein, the term "plant" can refer to a whole plant, any part thereof, or a cell or tissue culture derived from a plant. Thus, the term "plant" can refer to any of whole plants, plant components or organs (e.g., leaves, stems, roots, etc.), plant tissues, seeds and/or plant cells.

A plant cell is a cell of a plant, taken from a plant, or derived through culture from a cell taken from a plant. Thus, the term "plant cell" includes without limitation cells within seeds, suspension cultures, embryos, meristematic regions, callus tissue, leaves, shoots, gametophytes, sporophytes, pollen, and microspores. The phrase "plant part" refers to a part of a plant, including single cells and cell tissues such as plant cells that are intact in plants, cell clumps, and tissue cultures from which plants can be regenerated. Examples of plant parts include, but are not limited to, single cells and tissues from pollen, ovules, leaves, embryos, roots, root tips, anthers, flowers, fruits, stems, shoots, and seeds; as well as scions, rootstocks, protoplasts, calli, and the like.

As used herein, the term 'white' with respect to the white foliage phenotype of the Poinsettia of the invention is not limited to pure white or bright white, but encompasses off-white variation, in particular some yellowish shading and creamy white shading.

DETAILED DESCRIPTION

All publications, patents and patent applications, including any drawings and appendices, are herein incorporated by reference to the same extent as if each individual publication or patent application was specifically and individually indicated to be incorporated by reference.

The following description includes information that may be useful in understanding the present disclosure. It is not an admission that any of the information provided herein is prior art or relevant to the presently claimed disclosures, or that any publication specifically or implicitly referenced is prior art.

Embodiments described herein provide methods for the generation of plants having a dysfunctional glutathione S-transferase (GST) allele, and the seeds, plant parts or plant cells derived therefrom. Embodiments described herein also provide a molecular marker capable of identifying mutant GST, to isolating DNA encoding such a dysfunctional GST gene, and to the use of such DNA for the preparation of a molecular marker and for use in methods of targeted mutagenesis to inactivate the GST gene to generate plants with a white foliage phenotype.

GSTs comprise a family of eukaryotic and prokaryotic metabolic enzymes best known for their ability to catalyse the conjugation of the reduced form of glutathione (GSH) to xenobiotic substrates. GST also plays a role in transporting the red pigment anthocyanin into the vacuole, which is an essential step for the expression of red colour in plants. Thus, the knock-out of the transport mechanism (dysfunctional GST), through random or targeted mutagenesis, can provide a white foliage phenotype.

The *Euphorbia pulcherrima* GST gene (EpGST) gene described herein encodes an enzyme having the amino acid sequence of SEQ ID NO: 3, or encoding a functional homolog or variant of said protein with at least 60% amino acid identity, the gene having a Simple Sequence Repeat (SSR) of 4 nucleotides: CTTC-CTTC-CTTC, on positions 128-139 of the EpGST cDNA of SEQ ID NO: 2 and on positions 165-178 the gene sequence of SEQ ID NO: 1 in the region encoding amino acids at positions 40-50 of the protein.

Determination of the Gene and Amino Acid Sequence of EpGST from Poinsettia

To characterize the full-length sequence of the anthocyanin-related GST gene (EpGST, SEQ ID NO: 1), DNA from the red-bracted variety 'Vintage' was isolated from approximately 100 mg of leaf tissue using the NucleoSpin® Plant II kit (Macherey-Nagel GmbH & Co. KG, Germany) according to the manufacturer's instructions. The DNA concentration was analysed using NanoDrop™ 2000 (Thermo Fisher Scientific, USA) and gel electrophoresis.

Primers were designed from available DNA sequences previously obtained at the Institute for Plant Genetics of the Leibniz University of Hannover (Germany). The sequences of the primers used to amplify the full-length gene are F1 (TCCGATCTAAGAAATCAAGGCTA-forward, SEQ ID NO: 4) and R1 (CAGTCGGCCGCTACATAGAT-reverse, SEQ ID NO: 5). Two other primer pairs flanking the intronic regions were used in order to amplify smaller inner fragments to assure the correct sequencing: F2 (TGGCCTGCCTTTTAGAGAAA, SEQ ID NO: 6) and R2 (AAAGCCTGAAATCCCCATCT, SEQ ID NO: 7); F2 and R3 (TATGGGCTTCCACTTCAACC, SEQ ID NO: 8). The PCR reactions were performed in a 50 µL reaction containing 50 ng of DNA template, 1× PrimeSTAR® Buffer ($Mg^{2+}$ plus), 0.2 mM of each dNTP, 0.25 µM of forward and reverse primers and 1.25 U of PrimeSTAR® HS DNA Polymerase. The cycling conditions were 95° C. for 3 min; 30 cycles of 95° C. for 30 sec, 60° C. for 30 sec and 72° C. for 2 min; and a final extension of 10 min at 72° C. The PCR products were resolved in a 1% (w/v) agarose gel in horizontal electrophoresis for 90 min at 100 V. The correct bands were excised from the gel and purified using the NucleoSpin® Gel and PCR Clean-up (Macherey-Nagel GmbH & Co. KG, Germany) following manufacturer's recommendations. Finally, the purified PCR fragments were sent to Eurofins Genomics (Ebersberg, Germany) for Sanger sequencing. The generated sequences were aligned using BioEdit Sequence Alignment Editor v7.2.5 and a final full-length gene sequence for the EpGST was generated.

Shown in FIG. 1A is a schematic representation of the full-length sequence (2314 bp) of EpGST (SEQ ID NO: 1). Arrows represent the exon regions. Black lines represent the intron regions. The EpGST full-length sequence contains three exons (147 bp, 48 bp and 450 bp, respectively) and two introns (455 bp and 1214 bp, respectively). The box below exon 1 represents the location of the trinucleotide motif SSR locus ($CTTC_3$).

FIG. 1B shows the corresponding genomic gene sequence (as depicted in SEQ ID NO: 61) wherein the exons are shaded grey. Exon 1 corresponds to nucleotides 38-186, exon 2 corresponds to nucleotides 638-688, and exon 3 corresponds to nucleotides 1902-2351. The whole coding region has a size of 645 bp (SEQ ID NO: 2), which encodes for a putative protein of 214 amino acids (SEQ ID NO: 3) and has a mass of 24.6 kDa.

As disclosed herein, the use of random mutagenesis yields targeted deletions in the GST gene that are reproducible and consistent. Specifically, a four base pair deletion occurs in a part of the SSR ($CTTC_3$) GST gene. This deletion causes a frameshift and a functional knock-out of the GST target gene as the protein is truncated. The high reproducibility suggests a "hot spot" of mutation i.e., a region of DNA that exhibits an unusually high propensity to mutate. This provides a method for establishing targeted mutagenesis e.g. by using random mutagenesis techniques, or gene editing techniques therewith providing method to create plants with a dysfunctional GST, resulting in a white foliage phenotype.

An embodiment of present disclosure provides a method for the generation of plants having dysfunctional GST, comprising the steps of: providing a plant comprising in its genome at least one functional allele of a GST gene, or a functional variant thereof, wherein the GST gene comprises an SSR consisting of a threefold CTTC repeat in the region encoding amino acids at positions 40-50 of the protein of SEQ ID NO: 3; subjecting said plant to a mutagenesis treatment to produce a mutant plant; selecting a mutant plant wherein at least one allele of the GST gene comprises a CTTC deletion within said SSR region. The method may further comprise repeating said mutagenesis treatment until all alleles of the GST gene in the plant genome comprise the CTTC deletion; selecting a mutant plant that is homozygous for said CTTC GST deletion and having a white foliage phenotype, and may further comprise propagating and/or breeding said plant being homozygous for said CTTC GST deletion.

In another embodiment, the disclosure provides for plants, seeds, plant parts, and plant cells produced by the methods disclosed herein and having in its genome at least one dysfunctional allele of GST.

There are three domains in GST that have been identified to play an important and decisive role in anthocyanin binding (Conn et al., (2008) *J. Exp. Bot.* 59(13), 3621-3634). Thus, in another embodiment a functional homolog or variant may have a first domain at positions 11-13 of SEQ ID NO: 3 being AAC, AGC or AAN, where N can be any amino acid (SEQ ID NO: 62), a second domain at positions 53-56 of SEQ ID NO: 3 being LVPA, QVPA (SEQ ID NO: 63) or QPVP (SEQ ID NO: 64), and a third amino acid domain at positions 65-68 of SEQ ID NO: 3 being FESR, as well as the 12 nucleotides stretch [CTTC]3 in the region encoding amino acids at positions 40-50 of the protein. In this respect, a functional homolog is to be understood as a gene encoding a protein having the given amino acid identity.

In another embodiment, the homolog or variant of the protein encoded by the EpGST gene has a V on position 2 of SEQ ID NO: 3, and/or an F or an L on position 62 of SEQ ID NO: 3, and/or LE on positions 90-91 of SEQ ID NO: 3, and/or an S on position 153 of SEQ ID NO: 3, as these domains also play a role in the anthocyanin binding of the GST enzyme.

The plant targeted for mutagenesis may have other desirable traits that should not be lost when generating dysfunctional GST. As it was found that the white foliage trait (i.e. dysfunctional GST genes having the CTTC deletion) is recessive, the plant targeted for mutagenesis may be homozygous or heterozygous for the functional GST gene. Thus, at least one round of mutagenesis is necessary in order to arrive at a plant with a white foliage phenotype.

In another embodiment, the white-foliaged plant as described above has all of the essential phenotypic and morphologic characteristics of the non-white foliaged plant.

Examples of mutagens that may be used with the method disclosed herein include: radiation; such as X-rays, Gamma rays (e.g., cobalt 60 or cesium 137), neutrons, (product of nuclear fission by uranium 235 in an atomic reactor), Beta radiation (emitted from radioisotopes such as phosphorus 32 or carbon 14), or ultraviolet radiation (for example from 250 to 290 nm), temperature, long-term seed storage, tissue culture conditions, or chemical mutagens (such as base analogues (5-bromo-uracil)), related compounds (8-ethoxy caffeine), antibiotics (streptonigrin), alkylating agents (sulfur mustards, nitrogen mustards, epoxides, ethyleneamines, sulfates, sulfonates, sulfones, lactones), azide, hydroxylamine, nitrous acid, or acridines, proflavine, ICR191 and ethidium bromide (available on the world wide web at bio.brandeis.edu/classes/biol122a/Lecturerepeats.htm).
Other techniques such as gene editing are also possible and lie well within the scope of the skilled person.

The isolated DNA sequences disclosed herein and their fragments can be used for multiple purposes including but not limited to designing markers, probes, guide RNAs and other tools for the detection and/or modification of the GST gene.

In another embodiment the isolated DNA sequences are used to design molecular tools for targeted mutagenesis of the GST gene to deactivate said gene to achieve a white or essentially white foliage phenotype. The mutation in said GST gene may comprise a loss-of-function mutation, a partial loss-of-function mutation, a restored frameshift mutation, or an in-frame deletion mutation.

A further embodiment relates to a method of editing a GST gene of a plant, wherein said method is selected from the group comprising zinc finger nucleases, transcription activator-like effector nucleases (TALENs), engineered homing endonucleases/meganucleases, and the clustered regularly interspaced short palindromic repeat (CRISPR)-associated protein9 (Cas9) system, and plants produced therefrom.

Once a desired trait is observed through mutagenesis the trait may then be incorporated into existing germplasm by traditional breeding techniques. Details of mutation breeding can be found in Allard, Principles of Plant Breeding, John Wiley & Sons, Inc. (1960) but may include, for example, crossing, recurrent selection, mutation breeding, wherein said mutation breeding selects for a mutation that is spontaneous or artificially induced, backcrossing, pedigree breeding, marker enhanced selection, haploid/double haploid production, or transformation.

Breeding and selection schemes of the present disclosure can include crosses with plant lines that have undergone genome editing. In some embodiments, the breeding and selection methods of the present disclosure are compatible with plants that have been modified using any gene and/or genome editing tool, including, but not limited to: ZFNs, TALENS, CRISPR, and Mega nuclease technologies. In some embodiments, persons having skill in the art will recognize that the breeding methods of the present disclosure are compatible with many other gene editing technologies. In some embodiments, the present disclosure teaches gene-editing technologies can be applied for a single locus conversion, for example, conferring hemp plant with herbicide resistance. In some embodiments, the present disclosure teaches that the single locus conversion is an artificially mutated gene or nucleotide sequence that has been modified through the use of breeding techniques taught herein.

In some embodiments, the breeding and selection methods of the present disclosure are compatible with plants that have been modified through Zinc Finger Nucleases. Three variants of the ZFN technology are recognized in plant breeding (with applications ranging from producing single mutations or short deletions/insertions in the case of ZFN-1 and -2 techniques up to targeted introduction of new genes in the case of the ZFN-3 technique); 1) ZFN-1: Genes encoding ZFNs are delivered to plant cells without a repair template. The ZFNs bind to the plant DNA and generate site specific double-strand breaks (DSBs). The natural DNA-repair process (which occurs through nonhomologous end-joining, NHEJ) leads to site specific mutations, in one or only a few base pairs, or to short deletions or insertions; 2) ZFN-2: Genes encoding ZFNs are delivered to plant cells along with a repair template homologous to the targeted area, spanning a few kilo base pairs. The ZFNs bind to the plant DNA and generate site-specific DSBs. Natural gene repair mechanisms generate site-specific point mutations e.g. changes to one or a few base pairs through homologous recombination and the copying of the repair template; and 3) ZFN-3: Genes encoding ZFNs are delivered to plant cells along with a stretch of DNA which can be several kilo base pairs long and the ends of which are homologous to the DNA sequences flanking the cleavage site. As a result, the DNA stretch is inserted into the plant genome in a site-specific manner.

In some embodiments, the breeding and selection methods of the present disclosure are compatible with plants that have been modified through Transcription activator-like (TAL) effector nucleases (TALENs). TALENS are polypeptides with repeat polypeptide arms capable of recognizing and binding to specific nucleic acid regions. By engineering the polypeptide arms to recognize selected target sequences, the TAL nucleases can be used to direct double stranded DNA breaks to specific genomic regions. These breaks can then be repaired via recombination to edit, delete, insert, or otherwise modify the DNA of a host organism. In some embodiments, TALENSs are used alone for gene editing (e.g., for the deletion or disruption of a gene). In other embodiments, TALs are used in conjunction with donor sequences and/or other recombination factor proteins that will assist in the Non-homologous end joining (NHEJ) process to replace the targeted DNA region. For more information on the TAL-mediated gene editing compositions and methods of the present disclosure, see U.S. Pat. Nos. 8,440,432; 8,450,471; 8,586,526; 8,586,363; 8,592,645; 8,697,853; 8,704,041; 8,921,112; and 8,912,138, each of which is hereby incorporated in its entirety for all purposes.

In some embodiments, the breeding and selection methods of the present disclosure are compatible with plants that have been modified through Clustered Regularly Interspaced Short Palindromic Repeats (CRISPR) or CRISPR-associated (Cas) gene editing tools. CRISPR proteins were originally discovered as bacterial adaptive immunity systems which protected bacteria against viral and plasmid invasion. There are at least three main CRISPR system types (Type I, II, and III) and at least 10 distinct subtypes (Makarova, K. S., et. al., Nat Rev Microbiol. 2011 May 9; 9(6):467-477). Type I and III systems use Cas protein complexes and short guide polynucleotide sequences to target selected DNA regions. Type II systems rely on a single protein (e.g. Cas9) and the targeting guide polynucleotide, where a portion of the 5' end of a guide sequence is complementary to a target nucleic acid. For more information on the CRISPR gene editing compositions and methods of the present disclosure, see U.S. Pat. Nos. 8,697,359; 8,889,418; 8,771,945; and 8,871,445, each of which is hereby incorporated in its entirety for all purposes.

In some embodiments, the breeding and selection methods of the present disclosure are compatible with plants that have been modified through meganucleases. In some embodiments, meganucleases are engineered endonucleases capable of targeting selected DNA sequences and inducing DNA breaks. In some embodiments, new meganucleases targeting specific regions are developed through recombinant techniques which combine the DNA binding motifs from various other identified nucleases. In other embodiments, new meganucleases are created through semi-rational mutational analysis, which attempts to modify the structure of existing binding domains to obtain specificity for additional sequences. For more information on the use of meganucleases for genome editing, see Silva et al., 2011 Current Gene Therapy 11 pg 11-27; and Stoddard et al., 2014 Mobile DNA 5 pg 7, each of which is hereby incorporated in its entirety for all purposes.

Genotyping of Poinsettia Varieties for SSR Locus in the EpGST Sequence

To detect the four base pair deletion in the SSR locus in the EpGST sequence, a genotyping approach based on the fluorescent labelling of PCR fragments was applied (Schuelke, 2000, Nature Biotechnol 18:233-234).

Shown in FIG. 2 is an amplification scheme for the fluorescent labelling of PCR fragments to identify the four base pair deletion described above. The hatched boxes indicate deletion specific primers (SEQ ID NO: 9 and SEQ ID NO: 10). The undulating grey box indicates the universal M13(−21) sequence, and the star indicates the fluorescent FAM label. In the first PCR cycles, the forward primer with the M13(−21) tail is incorporated into the PCR products. These products are then the target for the FAM-labelled universal M13(−21) primer, which is incorporated during subsequent cycles at a lower annealing temperature of 53° C. The final labelled product can be analysed, for example, on a laser detection system (Figure adapted from Schuelke, (2000), Nature Biotechnol 18:233-234).

DNA samples from 78 different commercially available Poinsettia genotypes were isolated from approximately 100 mg of leaf tissue using the NucleoSpin® Plant II kit (Macherey-Nagel GmbH & Co. KG, Germany) according to the manufacturer's instructions. The DNA concentration was analysed using NanoDrop™ 2000 (Thermo Fisher Scientific, USA).

Primers were designed surrounding the SSR locus in the EpGST sequence, with an M13-tail added at the 5'-end of the forward primer. The sequences for the primers are the following: F (GTAAAACGACGGCCAGTTGGCCTGCCTTT-TAGAGAAA, SEQ ID NO: 9) and R (ACAAGTTCAGGGGGCTGAG, SEQ ID NO: 10).

The PCR reactions were performed in a 20 µl reaction containing 50 ng of DNA template, 1× Williams buffer, 0.15 mM of each dNTP, 0.0125 µM of forward, 0.07 µM of universal FAM labelled M13 primer, 0.25 µM of reverse primers and 1 U of DCSPol DNA Polymerase (DNA Cloning Service, Germany). The cycling conditions were 94° C. for 3 min; 24 cycles of 94° C. for 45 sec, 59° C. for 1 min and 72° C. for 1 min; 6 cycles of 94° C. for 30 sec, 52° C. for 45 sec and 72° C. for 1 min; and a final extension of 10 min at 72° C. 50 µl of formamide loading dye was added to each reaction and incubated at 95° C. for 5 min. The PCR products were resolved in 6% (w/v) acrylamide gel in vertical electrophoresis using the LI-COR Gene Reader 4200 DNA Analyzer (LI-COR Biosciences, USA).

Figure 3A:
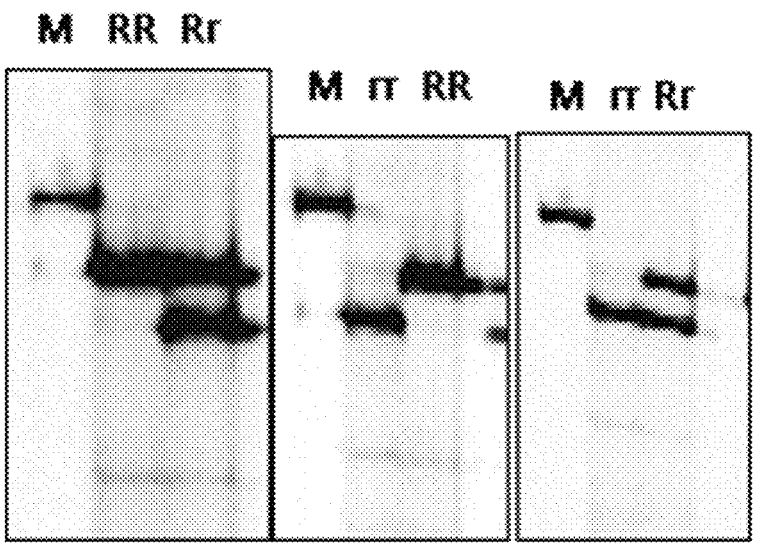
FIG. 3A shows the results of a PCR amplification of the trinucleotide motif SSR locus ($CTTC_3$) in EpGST resolved in 6% (w/v) acrylamide gel in vertical electrophoresis. M=marker; rr=recessive homozygous genotype for the SSR locus in the EpGST; Rr=heterozygous genotype for the SSR locus in the EpGST; RR=dominant homozygous genotype for the SSR locus in the EpGST.
Figure 3B:
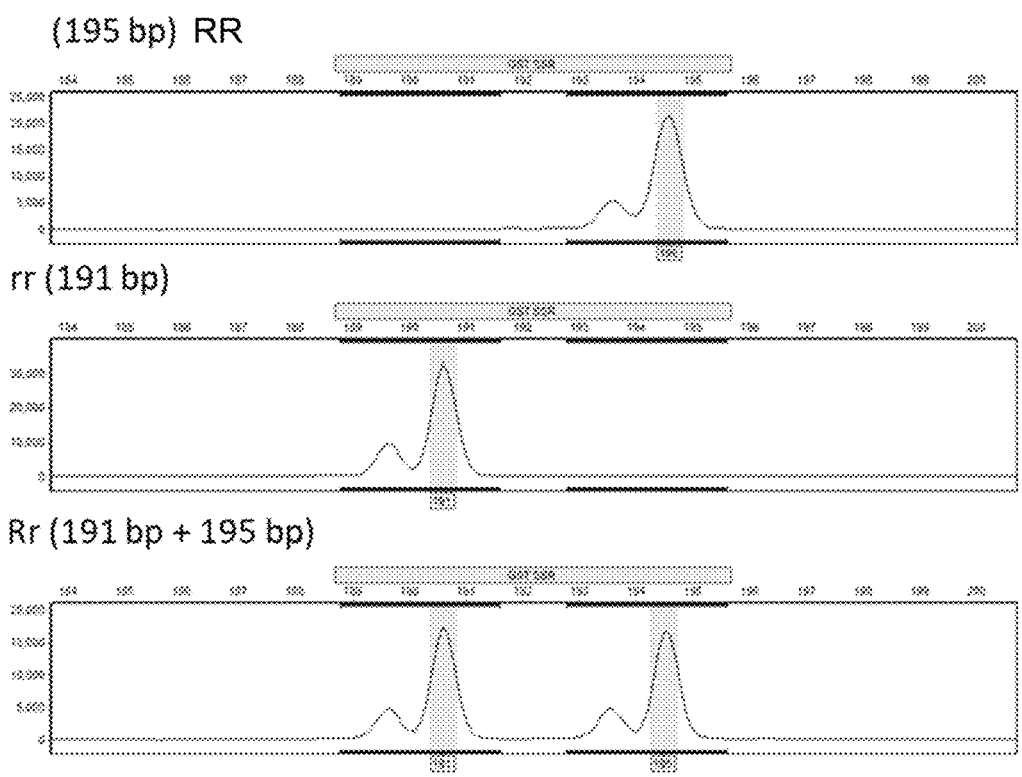
FIG. 3B shows the results of a PCR amplification of the trinucleotide motif SSR locus ($CTTC_3$) in EpGST resolved by capillary electrophoresis. Recessive allele r (comprising the four base pair deletion)=191 bp; Dominant allele R=195 bp.

The electrophoresis analysis results in the generation of a band of 195 bp size in case of the unmutated EpGST allele, whereas the mutated EpGST allele results in a 191 bp DNA fragment, which could clearly be separated from the unmutated EpGST allele by the analysis method (FIGS. 3A and 3B). Here, RR denominates the homozygous presence of only wildtype alleles (band at 195 bp only), Rr the heterozygous presence of the wildtype and the mutated allele (both bands), and rr the homozygous presence of only the mutated allele (band at 191 bp only).

Shown in FIG. 3A are the results of a PCR amplification of the trinucleotide motif SSR locus (CTTC$_3$) in EpGST resolved in 6% (w/v) acrylamide gel in vertical electrophoresis. M=marker; rr=recessive homozygous genotype for the SSR locus in the EpGST; Rr=heterozygous genotype for the SSR locus in the EpGST; and RR=dominant homozygous genotype for the SSR locus in the EpGST. As shown by the gel image, the three genotypes are clearly distinguishable, the homozygous RR dominant genotype having a single band at approximately 195 bp, the homozygous rr recessive genotype having a single band at approximately 191 bp, and the heterozygote exhibits both bands.

FIG. 3B shows the results of a PCR amplification of the trinucleotide motif SSR locus (CTTC$_3$) in EpGST resolved by capillary electrophoresis. Recessive allele r (comprising the four base pair deletion)=191 bp; Dominant allele R=195 bp. As shown by the images, there are clear peaks corresponding to, and distinguishing, the three genotypes.

The list of all tested genotypes, their elucidated zygosity status for the SSR locus and their respective bract colouration is given in Table 1.

TABLE 1

Poinsettia varieties tested

| Genotype ID | Genotype name | Denomination | Zygosity | Bract colour |
|---|---|---|---|---|
| 1 | Chr. Feelings Pearl | NPCW13211 | rr | White, RHS 4D |
| 2 | Chr. Glory White | NPCW17267 | rr | White, RHS 8D |
| 3 | Chr. Joy White | | rr | white |
| 4 | Bravo White | | rr | white |
| 5 | Titan White | | rr | white |
| 6 | SK158 White | | rr | white |
| 7 | SK130 White | | rr | white |
| 8 | Candlelight | NPCW12202 | rr | White, between RHS 158B and RHS 4D |
| 9 | Whitestar | | rr | white-light cream, RHS 4D |
| 10 | Premium Polar | | rr | white-light cream, close to RHS 144B |
| 11 | Chr. Carol White | | rr | White |
| 12 | Chr. Feelings White | | rr | White, RHS 1D |
| 13 | Chr. Star Marble | | rr | white |
| 14 | SK 136 White | | rr | white |
| 15 | Vintage | | RR | red |
| 16 | Chr. Tradition | NPCW14205 | RR | red |
| 17 | Chr. Aurora | NPCW14221 | RR | red |
| 18 | Chr. Morning | NPCW15237 | RR | red |
| 19 | Holy Day | NPCW13218 | RR | red |
| 20 | Chr. Wish Pink | NPCW18281 | RR | pink |
| 21 | Grande Italia | | RR | red |
| 22 | Prima Donna | | RR | red |
| 23 | Scandic Early | | RR | red |
| 24 | Early Millennium | | RR | red |
| 25 | Aries Red | | RR | red |
| 26 | Blissful Red | | RR | red |
| 27 | Maxima | | RR | red |
| 28 | Bouquet | | RR | red |
| 29 | Ferrara | | RR | red |
| 30 | Lyra Red | | RR | red |
| 31 | Tabaluga | | RR | red |
| 32 | Prestige Red | | RR | red |
| 33 | Chr. Spirit | NPCW04095 | RR | red |
| 34 | Chr. Day | NPCW10164 | RR | red |
| 35 | Chr. Eve | NPCW08153 | RR | red |
| 36 | Noel | NPCW10167 | RR | red |
| 37 | Astro Red | | RR | red |
| 38 | Leona Red | | RR | red |
| 39 | Viking Red | | RR | red |
| 40 | Bella Italia | | RR | red |
| 41 | Burning Ember | | RR | red |
| 42 | Mirage Red | | RR | red |
| 43 | Vega Red | | RR | red |
| 44 | Magma | | RR | red |
| 45 | Advantage Red | | RR | red |
| 46 | Chr. Cracker | NPCW17257 | RR | red |
| 47 | Chr. Magic | NPCW18268 | RR | red |
| 48 | Chr. Universe | | RR | red |
| 49 | SK167 | | RR | red |
| 50 | Chr. Feelings | NPCW02044 | Rr | red |
| 51 | Chr. Glory | NPCW12200 | Rr | red |
| 52 | Chr. Joy | NPCW12197 | Rr | red |
| 53 | Bravo Bright Red | | Rr | red |
| 54 | Titan Red | | Rr | red |
| 55 | SK130 | | Rr | red |
| 56 | SK158 | | Rr | red |
| 57 | Chr. Carol | NPCW04107 | Rr | red |
| 58 | Freedom | | Rr | red |
| 59 | Otto | | Rr | red |
| 60 | Chr. Season | KLEW01066 | Rr | red |
| 61 | Mars | | Rr | red |
| 62 | Mira | | Rr | red |
| 63 | Chr. Feelings Merlot | | Rr | red |
| 64 | Chr. Sensation | NPCW18087 | Rr | red |
| 65 | Chr. Break | | Rr | red |
| 66 | SK149 | | Rr | red |
| 67 | Chr. Mouse | | Rr | red |
| 68 | Chr. Feelings Select | NPCW08122 | Rr | red |
| 69 | Premium Red | | Rr | red |
| 70 | Infinity Red 2.0 | | RR | red |
| 71 | Valentino | NPCW11201 | RR | red |
| 72 | Scarlet Red | | RR | red |
| 73 | SK168 | | RR | red |
| 74 | SK176 | | Rr | red |
| 75 | SK175 | | Rr | red |
| 76 | SK172 | | RR | orange |
| 77 | SK173 | | RR | orange |
| 78 | SK174 | | RR | orange |

In some embodiments, the dysfunctionality or functionality of GST is identified by the amplification scheme disclosed herein.

In other embodiments, mutant plants generated by the methods disclosed herein may be identified by any number of mechanisms. Molecular markers may be designed and made, based on the genome of the plants of the present application. In some embodiments, the molecular markers are selected from Isozyme Electrophoresis, Restriction Fragment Length Polymorphisms (RFLPs), Randomly Amplified Polymorphic DNAs (RAPD5), Arbitrarily Primed Polymerase Chain Reaction (AP-PCR), DNA Amplification Fingerprinting (DAF), Sequence Characterized Amplified Regions (SCARs). Amplified Fragment Length Polymorphisms (AFLPs), and Simple Sequence Repeats (SSRs) which are also referred to as Microsatellites, etc. Methods of developing molecular markers and their applications are described by Avise (Molecular markers, natural history, and evolution, Publisher: Sinauer Associates, 2004, ISBN 0878930418, 9780878930418), Srivastava et al. (Plant biotechnology and molecular markers, Publisher: Springer, 2004, ISBN1402019114, 9781402019111), and Vienne (Molecular markers in plant genetics and biotechnology, Publisher: Science Publishers, 2003), each of which is incorporated by reference in its entirety for all purposes.

In other embodiments, dysfunctional or functionality of GST may be identified by biochemical assays. The GST enzyme described herein has a flavonoid binding affinity, i.e. substrate specificity at the N-terminus of the protein. This functionality or dysfunctionality can be determined in a biochemical assay such as a ligand fishing assay (Dixon & Edwards (2010) *J. Biol. Chem.* 285, 36322-36329). In particular, a GST enzyme that binds to an anthocyanin affinity column can be regarded as being a functional enzyme. To this end, a protein mixture from a plant extract can be passed over an affinity matrix comprising anthocyanins (or precursors thereof) immobilized thereon, and functional GST enzyme molecules bind to the said ligands and can be eluted afterwards. Dysfunctional GST enzymes will not bind, or bind to a significantly lesser extent. Dysfunctional GST enzymes that do not bind to an anthocyanin column, or exhibit of binding of less than 60%, but may exhibit as little as 10% compared to the binding of wild type GST enzyme, can result in loss of foliage colouration and can therefore be regarded as dysfunctional. A functional variant or homolog of the GST enzyme will bind with an affinity of at least 60%. In another embodiment the dysfunctionality may also affect the GST capability as a transport protein.

In other embodiments, the dysfunctionality or functionality of GST can also be assessed by a genetic complementation of mutant lines (Li et al. (2011) *Plant Cell Environ.* 34, 374-388, Sun et al. (2012) *Mol. Plant* 5, 387-400, Alfenito et al. (1998) *Plant Cell* 10, 1135-1149, and Smith et al. (2003) *Plant J.* 36, 433-442.

In another embodiment, the molecular markers disclosed herein can be used in molecular marker assisted breeding. For example, the molecular markers can be utilized to monitor the transfer of the genetic material. In some embodiments, the transferred genetic material is a gene of interest, such as genes that contribute to one or more favourable phenotypes when expressed in a plant cell, a plant part, or a plant.

Detection of a Single Sequence Repeat Locus in the EpGST Sequence

The colour range in Poinsettia varieties is obtained either through classical breeding or mutagenic breeding, thus generating a spectrum of bract colours, such as pink, marble, orange and white/creamy. The white genotypes are often obtained through several rounds of radiation mutagenesis starting with a plant having the red genotype, followed by shoot development and trait selection. Therefore, red and white Poinsettias from the same genotype are referred to as 'pairs', due to their similar genetic background. Six pairs of red- and white-bracted varieties of Poinsettia (Christmas Feelings' (SEQ ID NO: 13), 'Christmas Feelings White' (SEQ ID NO: 19), 'Christmas Glory' (SEQ ID NO: 14), 'Christmas Glory White' (SEQ ID NO: 20), 'Christmas Joy' (SEQ ID NO: 15), 'Christmas Joy White' (SEQ ID NO: 21), 'SK130' (SEQ ID NO: 18) and 'SK130 White' (SEQ ID NO: 24), all from Klemm+Sohn; 'Titan Red' (SEQ ID NO: 16) and 'Titan White' (SEQ ID NO: 22) from Syngenta; and 'Bravo Bright Red' (SEQ ID NO: 17) and 'Bravo White' (SEQ ID NO: 23) from Dümmen Orange) were used to analyse the coding sequence of the EpGST gene. Total RNA was isolated from approximately 100 mg of bract tissue using the mirPremier™ miRNA isolation kit (Sigma-Aldrich, USA) according to the manufacturer's instructions. The total RNA concentration was analysed using Nano-Drop™ 2000 (Thermo Fisher Scientific, USA). cDNA synthesis was performed using the FastGene Scriptase Basic cDNA Kit (Nippon Genetics Europe GmbH, Germany) according to the manufacturer's recommendations. The primers used for the PCR amplification were F1 (SEQ ID NO: 4) and R1 (SEQ ID NO: 5). PCR amplification protocol and sequencing strategies were the same used above.

Figure 4:
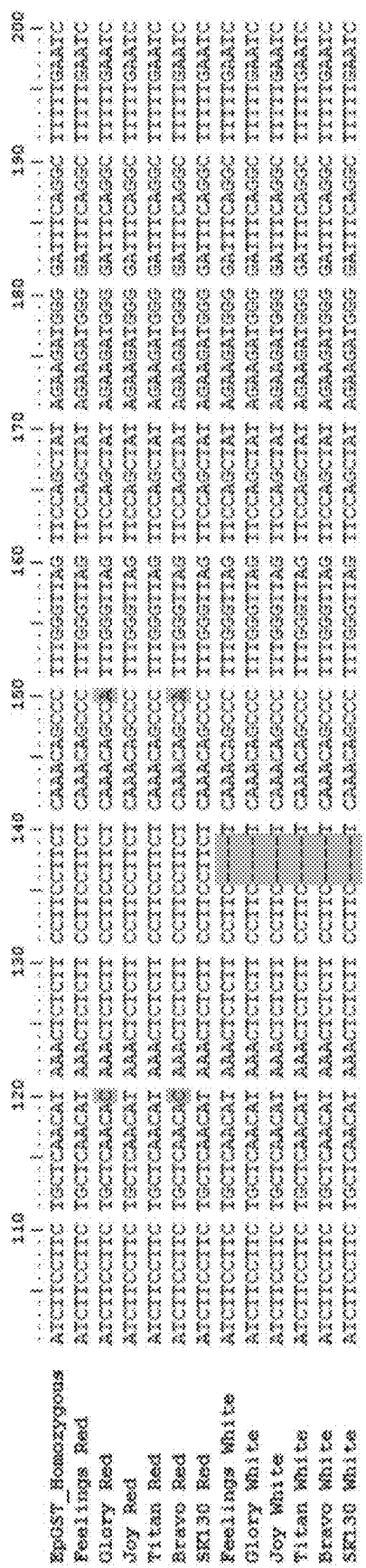
FIG. 4 represents an alignment of the EpGST coding sequences for 12 red- and white-bracted Poinsettia genotypes. The first sequence (named RNASeq_Homozygous) corresponds to the EpGST from the homozygous variety 'Vintage' (Klemm+Sohn) and was used as a reference for the alignment, the remaining 12 sequences correspond to SEQ ID NOs: 13-24.

The sequence alignment of the coding of the EpGST showed high similarity for all genotypes. However, a 4 bp deletion located 8 bp upstream the first exon-intron junction was observed in all white genotypes (FIG. 4). The deletion is located at position 136-139 in the SSR locus described herein, the trinucleotide motif $(CTTC)_3$ (see also FIG. 1A). The 4 bp deletion in the SSR locus results in a putative early stop codon on the amino acid sequence of the GST protein, thus leading to a non-functional protein.

The relation of the 4 bp deletion with the bract colouration in PRINCETTIA® was investigated. PRINCETTIA® is an interspecific hybrid of *E. pulcherrima* and *E. cornastra*. The EpGST coding region from the following 16 Poinsettia and PRINCETTIA® genotypes was analysed: 1) white genotypes—'PRINCETTIA® Pearl' (SEQ ID NO: 25) and 'PRINCETTIA® Pure White' (SEQ ID NO: 26) from Sakata (Japan), 'Alaska' (SEQ ID NO: 27) and 'Alpina' (SEQ ID NO: 28) from Lazzeri (Italy), 'SK158 White' (SEQ ID NO: 29) and 'Christmas Beauty White' (SEQ ID NO: 30) from Klemm+Sohn (Germany); 2) pink genotypes—'PRINCETTIA® Dark Pink' (SEQ ID NO: 31), 'PRINCETTIA® Hot Pink' (SEQ ID NO: 32), 'PRINCETTIA® Pink' (SEQ ID NO: 33) and 'PRINCETTIA® Soft Pink' (SEQ ID NO: 34) from Sakata (Japan); and 3) red genotypes: 'Premium' (SEQ ID NO: 35) and 'Freedom' (SEQ ID NO: 36) from Dümmen Orange (Netherlands), 'Otto' (SEQ ID NO: 37) from Süptitz (Germany), 'Christmas Season' (SEQ ID NO: 38), 'Christmas Beauty' (SEQ ID NO: 39) and 'SK158' (SEQ ID NO: 25) from Klemm+Sohn (Germany).

Figure 5:
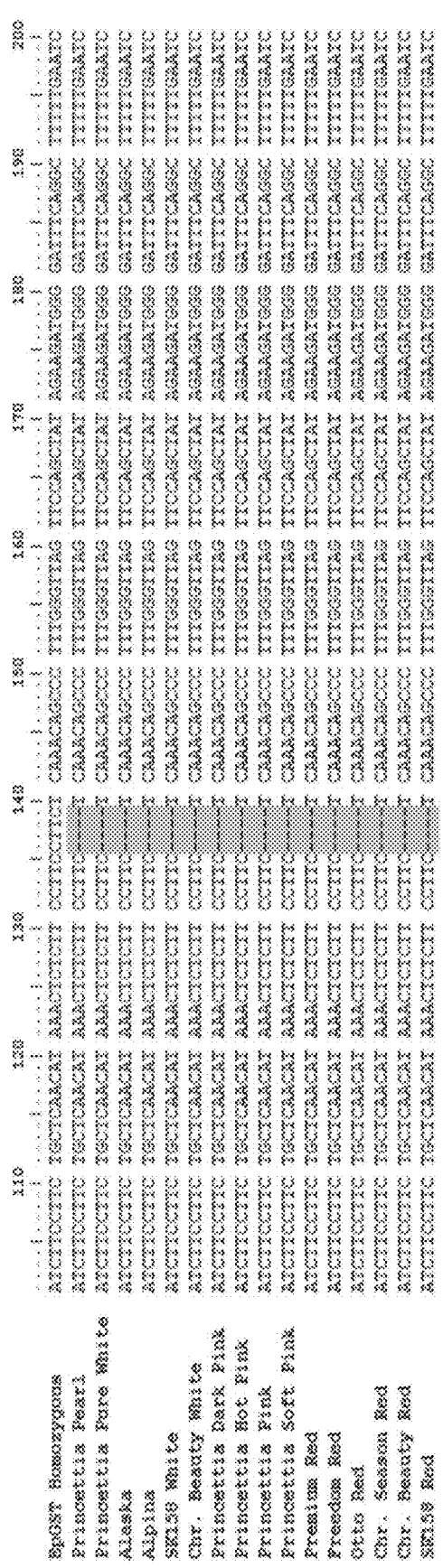
FIG. 5 represents an alignment of the EpGST coding sequence for 16 pink-, red- and white-bracted Poinsettia/PRINCETTIA® genotypes. The first sequence (named Homozygous) corresponds to the EpGST from the homozygous 'Vintage' genotype and was used as a reference for the alignment, the remaining 16 sequences correspond to SEQ ID NOs: 25-40.

FIG. 5 represents an alignment of the EpGST coding sequence for the 16 lines described above. The first sequence (named Homozygous) corresponds to the EpGST from the homozygous 'Vintage' genotype and was used as a reference for the alignment. As shown in FIG. 5, the homozygous 'Vintage' genotype comprises a complete $(CTTC)_3$ repeat motif, whereas the white varieties PRINCETTIA® 'Pearl', PRINCETTIA® 'Pearl White', 'Alaska', 'Alpina', and 'SK158' exhibit a CTTC deletion at position 136-139. All the genotypes showed the 4 bp deletion in the same position. Therefore, a heterozygous locus was believed to be present in the red and pink genotypes. Interestingly, all the white, pink and red PRINCETTIA® varieties exhibited the CTTC deletion at position 136-139 but were found to contain a functional gene as well. This is perhaps due to the interspecific hybrid nature of these lines. The reason for the white foliage phenotype may therefore be of another origin for PRINCETTIA®.

It was further observed that both Poinsettia varieties 'Alaska' and 'Alpina', while being white, nevertheless appeared to be heterozygous for the EpGST gene, i.e. both varieties still having a functional EpGST gene. It is believed that these varieties must have been mutated elsewhere in the genome, e.g. affecting pigment production. For these varieties, another mode of action occurs with regard to the white foliage phenotype, for example a mutation in the carotenoid producing pathway, explaining their bright white phenotype. Indeed, these varieties have an extreme bright white foliage, i.e. without any substantial shades of yellow. In contrast, it was observed that in plants, being homozygous for the mutant EpGST gene, and having the white phenotype of the invention, the white colour of the foliage is not limited to pure white or bright white as observed for 'Alaska' and 'Alpina', but encompasses off-white variations, in particular some yellowish shading and creamy white shading. The mutant plants as described herein usually have an off-white yellowish shading as compared to the 'Alaska' and 'Alpina' varieties. It is hypothesized that the off-white phenotype for homozygous mutants of the EpGST gene is often not as bright as that of 'Alaska' and 'Alpina', for example, as in the EpGST mutants the carotenoids, responsible for the foliage colouring are still produced, while this may not be the case for the 'Alaska' and 'Alpina' varieties.

The method disclosed herein allows for the conversion of wild-type lines to mutant, dysfunctional GST derivatives without the need for crossing and backcrossing, thereby preserving essentially all the physiological and morphological characteristics of the starting material. This is especially beneficial for lines which are vegetatively propagated e.g., chimeras etc.

Shown below in Table 2 are examples of elite original Poinsettia varieties which may be used with the method disclosed herein.

TABLE 2

| Trade Name | Denomination |
| --- | --- |
| Christmas Day | NPCW10164 |
| SK 191 | |
| SK 185 | |
| Christmas Eve | NPCW08153 |
| Noel | NPCW10167 |
| Christmas Aurora ® | NPCW14221 |
| Holy Day/Christmas Wish | NPCW13218 |
| Christmas Cracker | NPCW17257 |
| Christmas Universe/ Christmas Bells | NPCW19282 |
| Christmas Angel | NPCW20275 |
| Happy Mood | NPCW20344 |

Examples of additional varieties can be readily identified using the variety finders of the EU Community Plant Variety Office (available on the world wide web at cpvo.europa.eu/en/applications-and-examinations/cpvo-variety-finder), UPOV (available on the world wide web at upov.int/pluto/en/), USDA (available on the world wide web at ams.usda.gov/datasets/plant-variety), US-PTO (available on the world wide web at patft.uspto.gov/), or other databases known to the person skilled in the art, electronic catalogues, and internet resources.

Phylogenetic Analysis of GST Genes

GST genes play an important role in anthocyanin transportation, since GST mutants show phenotypes with a visible lack of pigmentation, such as bz2 (Bronze-2) from maize, an9 (Anthocyanin 9) from *Petunia*, tt19 (Transparent Testa 19) from *Arabidopsis* and fl3 (Flavonoid3) from *Dianthus* (Marrs et al., (1995) Nature 375:397-400; Alfenito et al., (1998) Plant Cell 10: 1135-1149; Larsen et al., (2003) Plant Cell Rep 21:900-904; Kitamura et al., (2004) Plant J 37:104-114). Moreover, there is a high functional conservation of GSTs involved in flavonoid accumulation (Zhao (2015) Trends Plant Sci 20(9):576-585).

Different phylogenetic analyses were performed to evaluate the similarity of the anthocyanin-related EpGST with genes encoding GST from different plant species. The following anthocyanin-related GSTs from other species were included in the analysis: CkmGST3 (*Cyclamen persicum* x *Cyclamen purpurascens*—AB682678.1; SEQ ID NO: 45), LcGST4 (*Litchi chinensis*—KT946768.1; SEQ ID NO: 47), VvGST4 (*Vitis vinifera*—AY971515.1; SEQ ID NO: 46), PhAN9 (*Petunia hybrida*—Y07721.1; SEQ ID NO: 44), PpRiant1 (*Prunus persica*—KT312847.1; SEQ ID NO: 48), PpRiant2 (*Prunus persica*—KT312848.1; SEQ ID NO: 49), AtGSTF11 (*Arabidopsis thaliana*—NM_111189.3; SEQ ID NO: 41) and AtTT19 (*Arabidopsis thaliana*—NM_121728.4; SEQ ID NO: 42). The nucleotide coding sequence of EpGST (SEQ ID NO: 2) and its version containing a 4 bp deletion (SEQ ID NO: 41) as well as the deducted amino acid sequences were compared with the aforementioned GSTs and deducted amino acid sequences from other species (SEQ ID NOs: 3 and 50-59, respectively).

Sequence alignment was performed using ClustalW and the best DNA/Protein Model was calculated with MEGA v7.0 with the following parameters: i) Tree to use—Neighbour-joining tree and ii) Statistical method—Maximum Likelihood (ML). An ML tree was generated using MEGA v7.0 with bootstrap values calculated from 1000 replicate analyses.

In order to analyse similarities among EpGST and anthocyanin-related GSTs from other species (CkmGST3, LcGST4, VvGST4, PhAN9, PpRiant1, PpRiant2, AtGSTF11 and AtTT19) the gene sequences were analysed.

Figures 1, 6A:
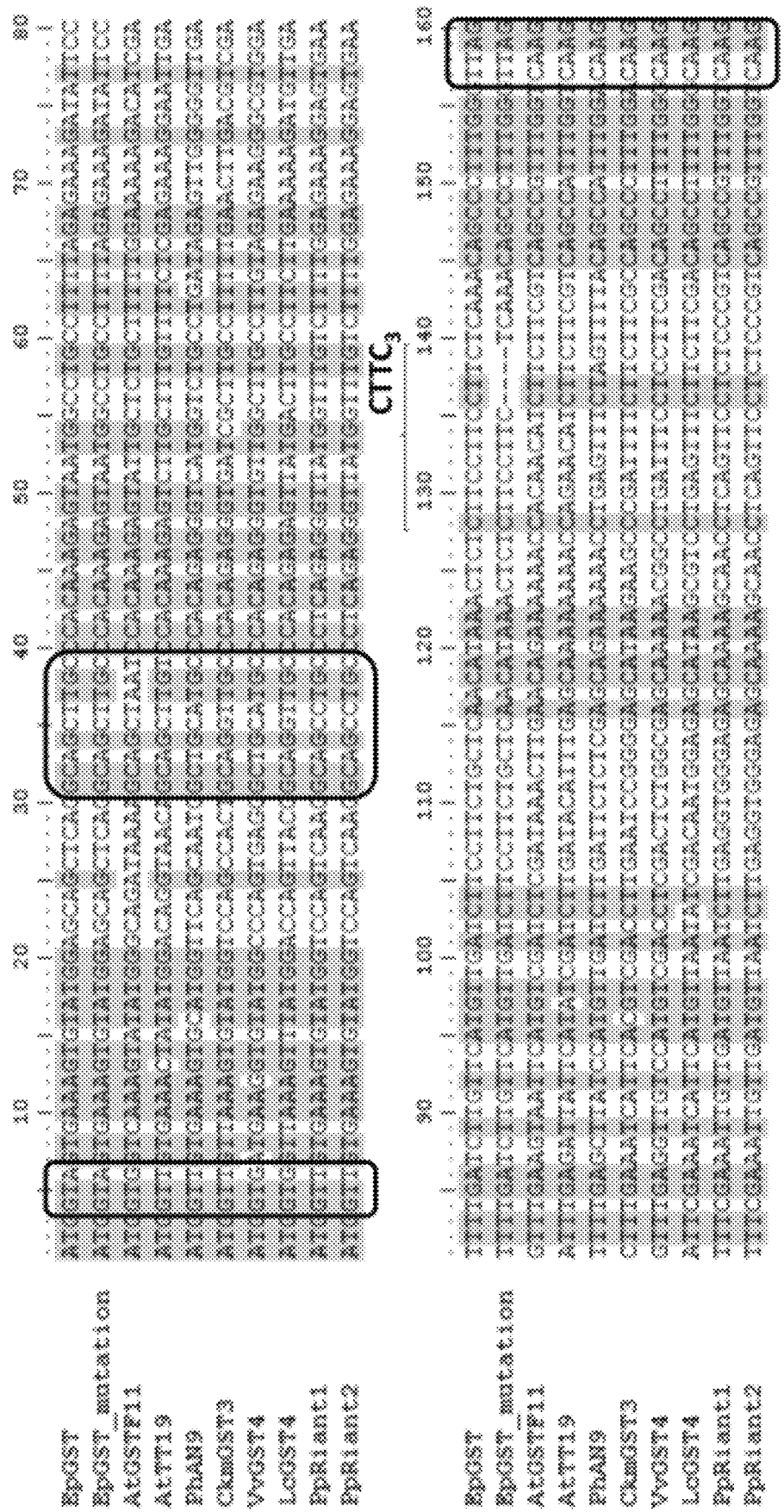
Figures 2, 6A:
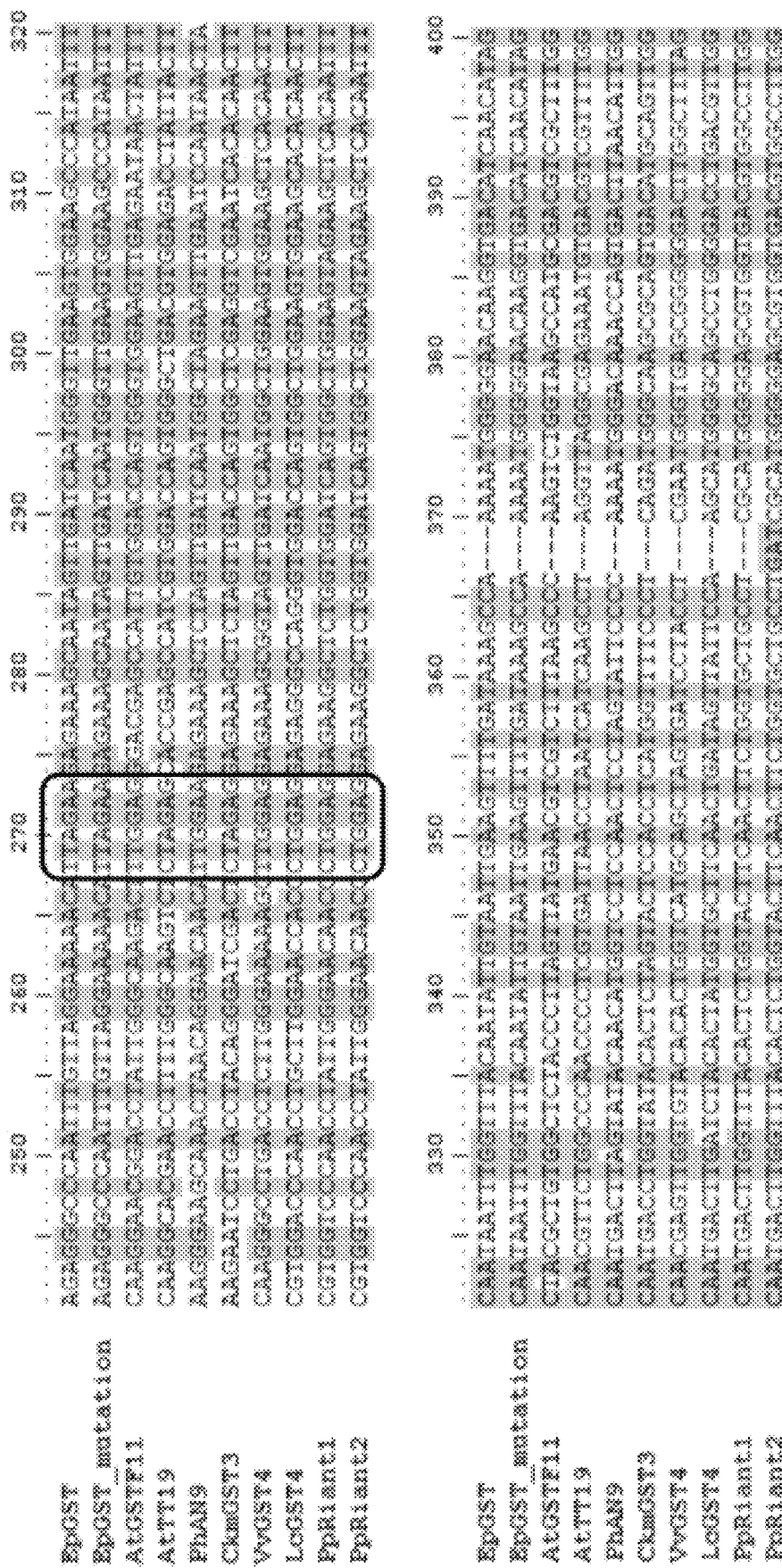
Figures 3, 6A:
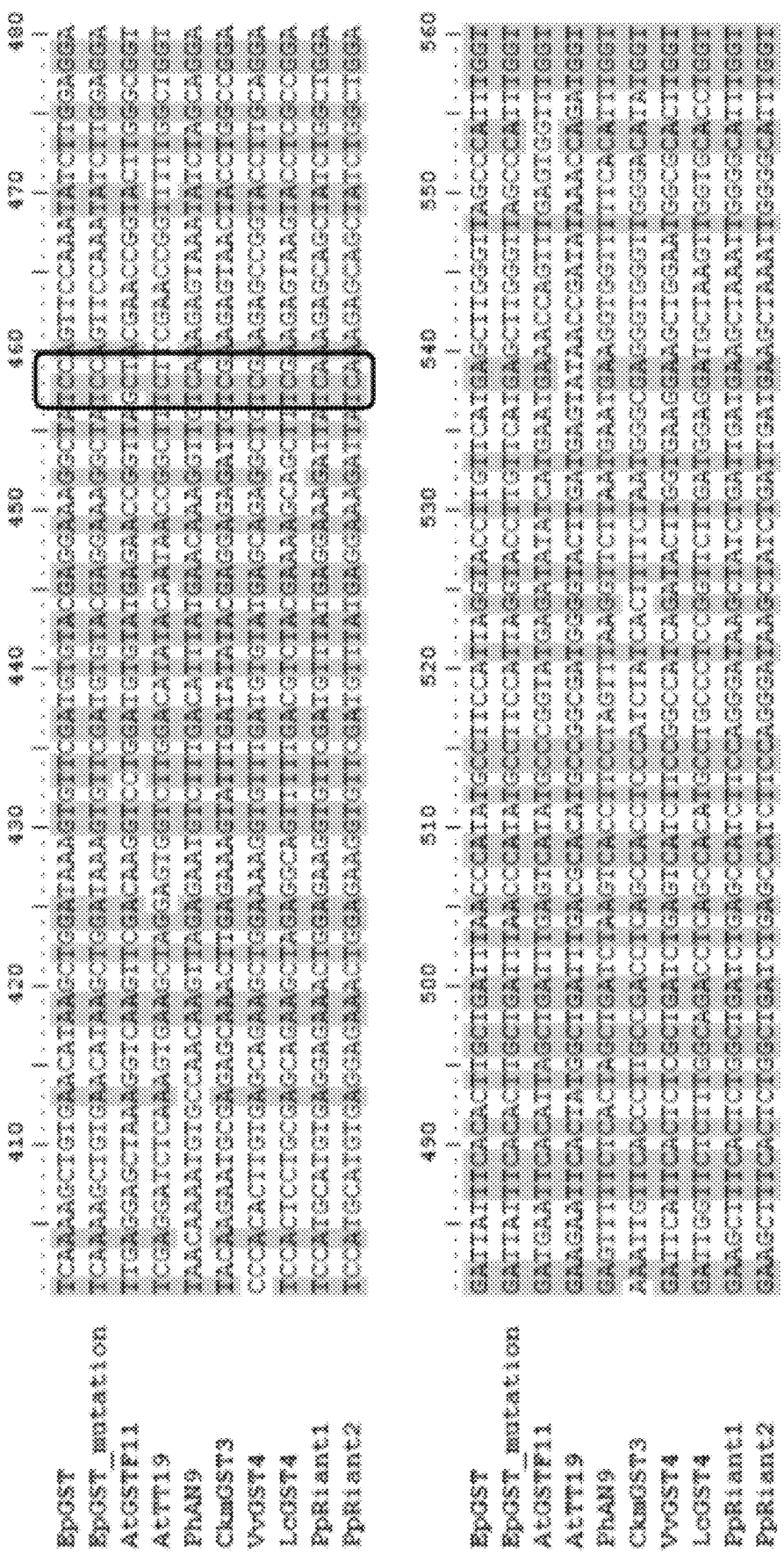
Figures 4, 6A:
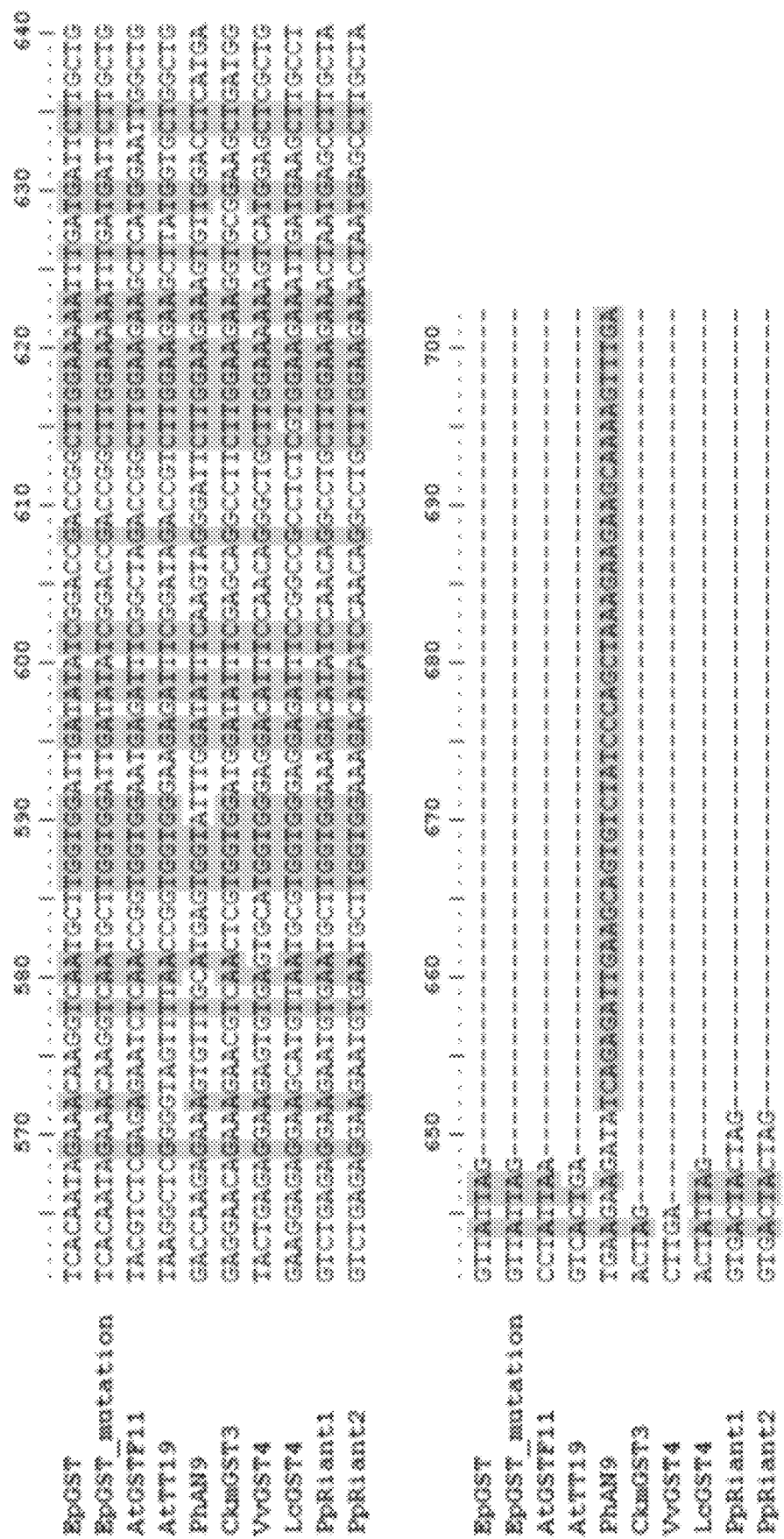

FIGS. 6A-1 to 6A-4 represent a ClustalW sequence alignment of these coding nucleotide sequences. Both wild type and mutated (first and second row, respectively) with known anthocyanin-related GST genes from other plant species: AtGSTF11, AtTT19, PhAN9, CkmGST3, VvGST4, LcGST4, PpRiant1 and PpRiant2 (rows 3-10, respectively). The $CTTC_3$ SSR locus is marked above the alignment. Conserved sequences among all the genes are shown with a grey background. Sequences encoding anthocyanin binding domains are indicated in boxes. By aligning the coding nucleotide sequences of both EpGST alleles (with and without the 4 bp deletion at the $CTTC_3$ SSR locus) with anthocyanin-related GSTs from other species, an overall nucleotide similarity of 64% was observed. Moreover, none of the anthocyanin-related genes contains the same $CTTC_3$ motif as observed in the EpGST.

Figure 6B:
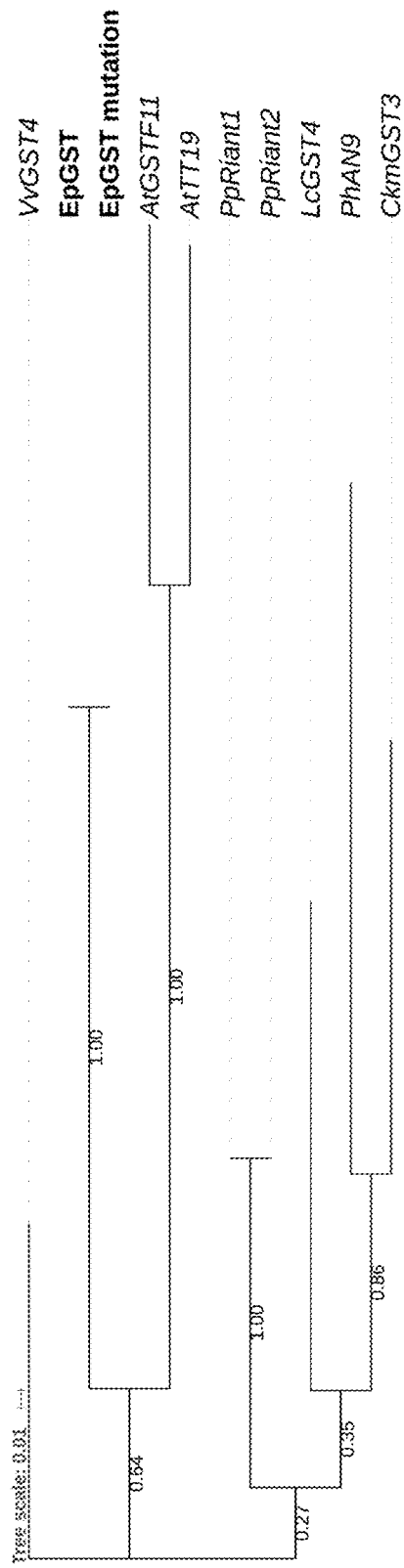
FIG. 6B shows a phylogenetic tree (Constructed Neighbour-Joining tree) of the EpGST coding nucleotide sequence with known anthocyanin-related GST genes from other plant species. Bootstrap values were calculated from 1000 replicate analyses and are shown under the tree branches.

FIG. 6B shows a phylogenetic tree (Constructed Neighbour-Joining tree) of the EpGST coding nucleotide sequence with known anthocyanin-related GST genes from other plant species. Bootstrap values were calculated from 1000 replicate analyses and are shown under the tree branches. The phylogenetic tree shows that the EpGST presents more similarity with AtGSTF11 and AtTT19 from *A. thaliana* than with the other anthocyanin-related genes.

Figures 1, 7A:
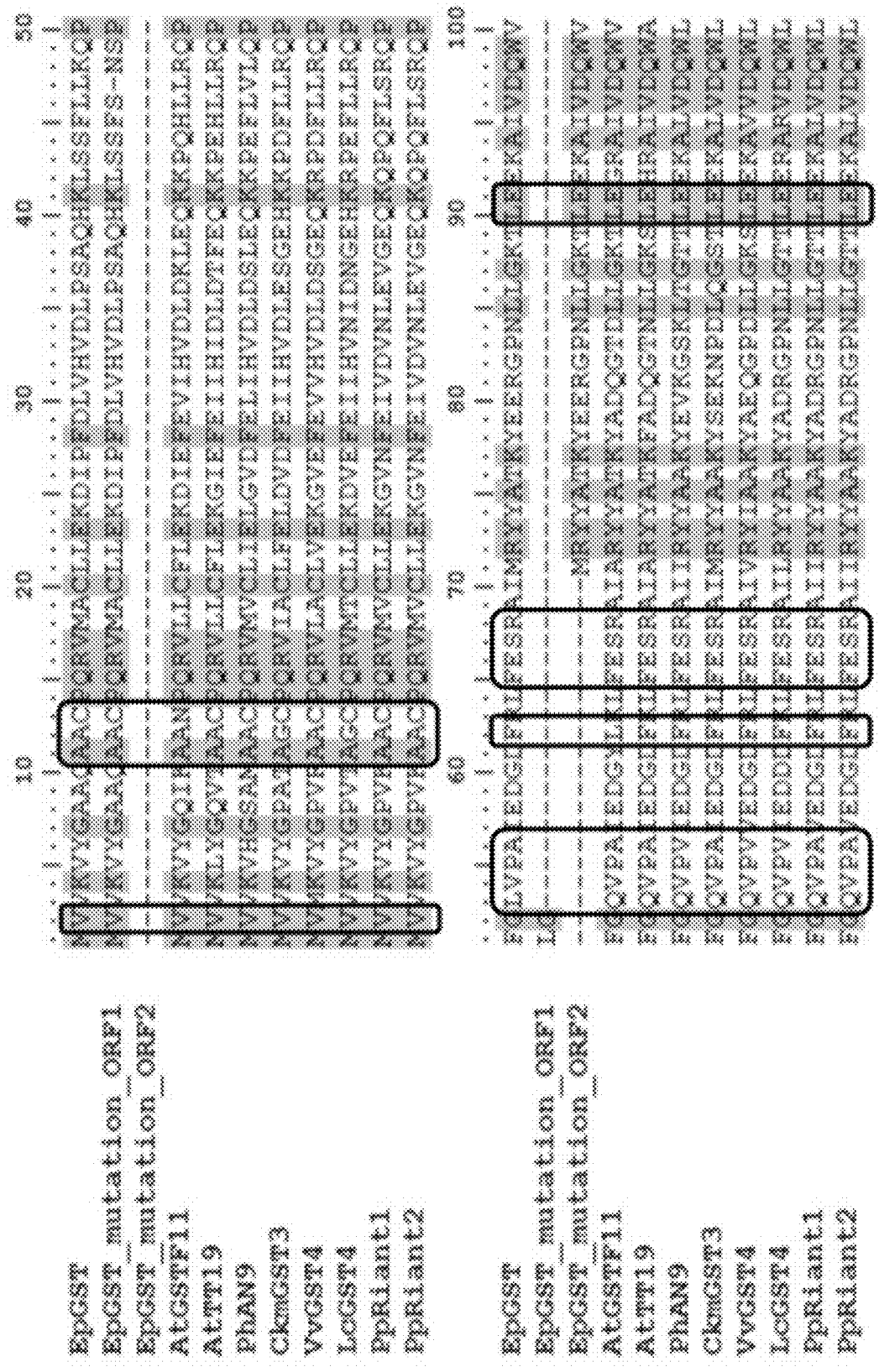
Figures 2, 7A:
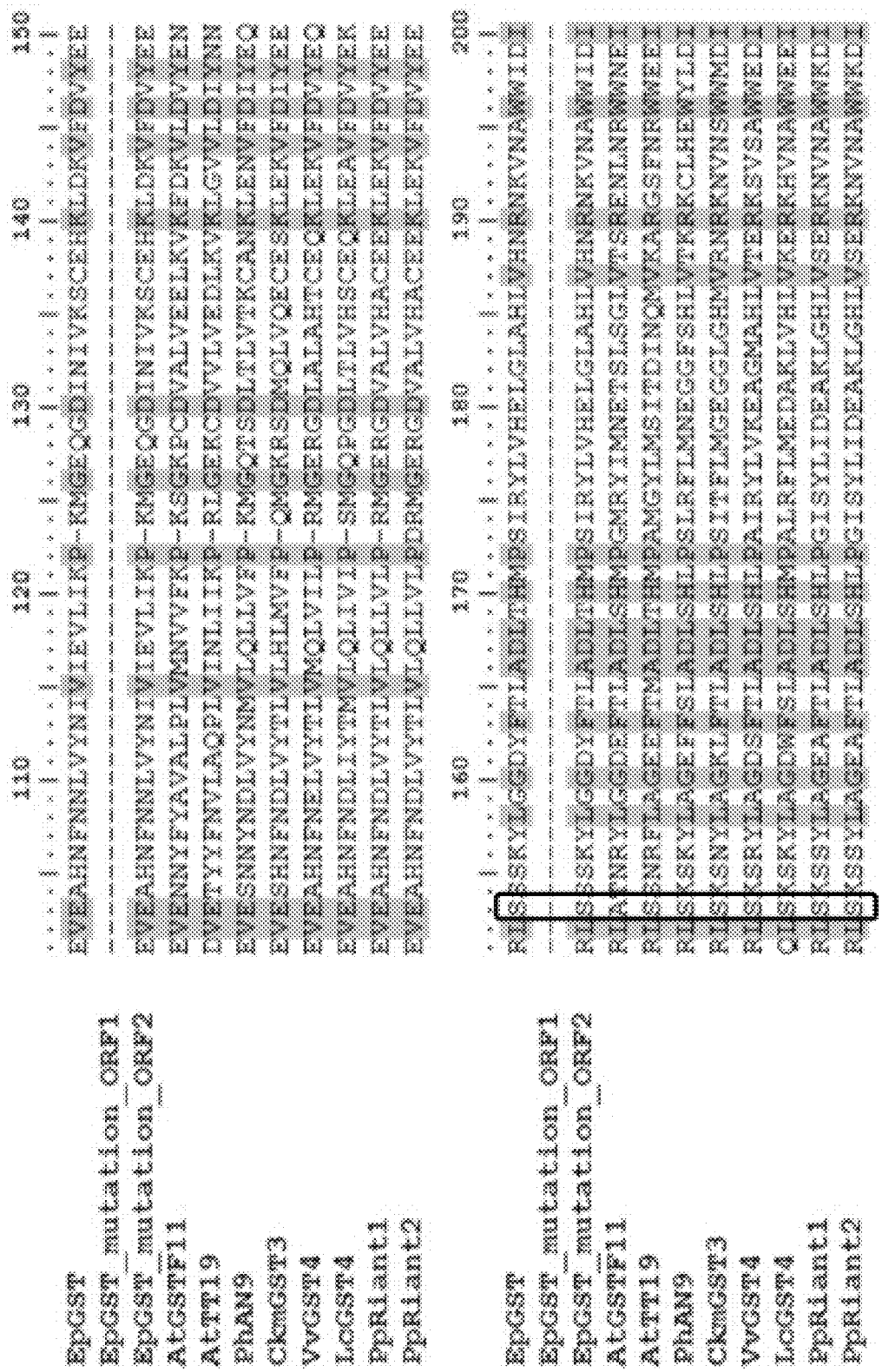

FIGS. 7A-1 to A-3 represent a ClustalW amino acid sequence alignment of the EpGST gene and known anthocyanin-related GST genes from other plant species. Conserved sequences among all the genes are shown with a grey background. Anthocyanin binding domains are indicated in boxes. A further analysis was made with regard to the similarity of the deducted amino acid sequence from the EpGST with the amino acid sequences of the same anthocyanin-related genes. The amino acid alignment showed an overall similarity of 61%.

Figures 3, 7A, 7B:
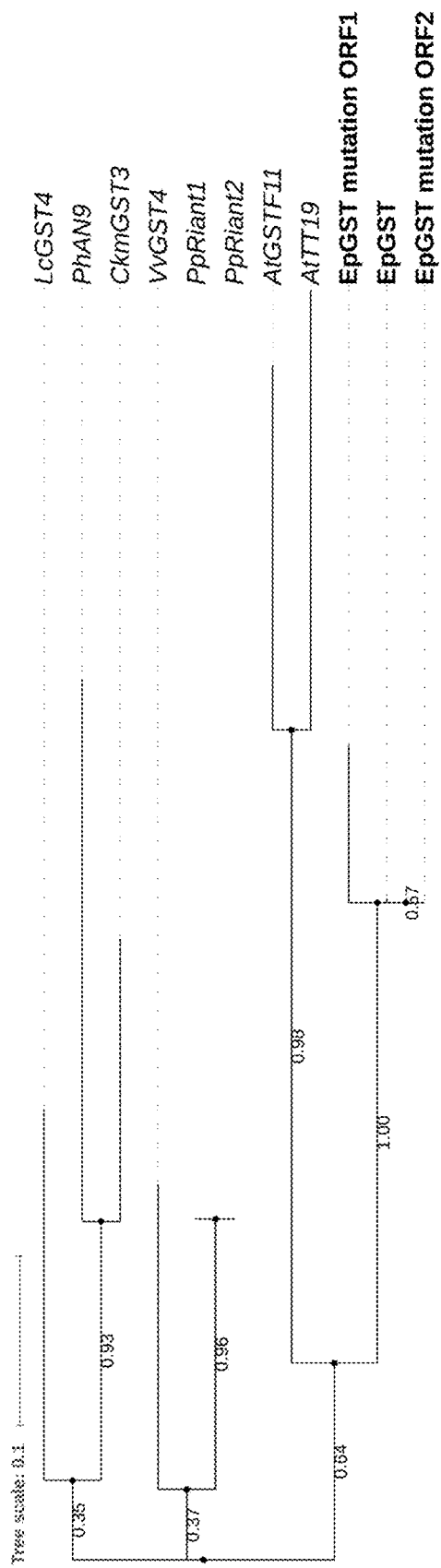

FIG. 7B shows a phylogenetic tree (Constructed Neighbour-Joining tree) of the EpGST amino acid sequence with known anthocyanin-related genes. Bootstrap values were calculated from 1000 replicate analyses and are shown under the tree branches. The phylogenetic tree shows that the deducted amino acid sequence from EpGST presents more similarity with AtGSTF11 and AtTT19 from *A. thaliana* than with the other anthocyanin-related GST genes.

By the finding that plants, being homozygous for the GST gene corresponding to that of the EpGST gene of *Euphorbia pulcherrima* (based on the presence of the above-mentioned domains and functionality) will have a phenotype wherein the anthocyanin mediated colour will be significantly decreased or abolished, such as e.g. the case for *Vitis vinifera*, where the functional loss of GST results in white grapes of varieties that are red in case the corresponding functional GST gene would be present. This approach may be useful as an alternative for producing "Blanc de noirs" wines, sparkling wines or champagnes. Normally a "Blanc de noirs" (literally "white from blacks") wine is a white wine produced entirely from black grapes. This is possible by careful processing of red grapes, as all the anthocyanins are retained in the skin. However, this processing requires hand-picking and careful treatment and is often not perfect resulting in a slight colouring of the wine. These issues can be resolved by the method of the present disclosure as no red anthocyanin pigments would become incorporated in the skin.

In other embodiments, additional species of plants, for example those having petaloid bracts such as *Bougainvillea* and *Cornus*, as well as those analysed herein with anthocyanin-related GST genes, may be targeted for mutagenesis using the methods disclosed herein to generate dysfunctional GST. These species may at least include the species for which the GST target sequences are provided herein: *Cyclamen persicum* x *Cyclamen purpurascens*, *Vitis vinifera*, *Litchi chinensis*, *Prunus hybrida*, *Prunus persica* and *Arabidopsis thaliana*.

EXAMPLES

The following examples are provided to illustrate further the various applications and are not intended to limit the disclosure beyond the limitations set forth in the appended claims.

Example 1: Generation of White-Bracted Poinsettia Plants from Elite Plant Material Through Irradiation Commercial Poinsettia elite lines, selected for superior characteristics, e.g. high cuttings yield, reliable and fast rooting, very good branching, early flowering and excellent shelf life were chosen as starting material for irradiation treatments to achieve white foliage types maintaining all the characteristics of the elite line. Usually the bract colour of the starting elite line is red but may also be pink or marble or alternatively it may show variations or shades of these colours and patterns. Furthermore, usually it is not known whether the allele composition of the GST gene of such elite Poinsettia line is homozygous or heterozygous. However, lines that are pink or marble are more likely to be heterozygous for functional GST.

In a typical experiment to generate a targeted mutation in the anthocyanin-related GST gene, the apical meristems of 30 Poinsettia young plants were irradiated with a total dosage of 30 Gray of X-ray radiation, but alternatively dosages between 15 and 50 Gray may be applied. The aim was to create single cells with a 4 bp mutation at the anthocyanin-related GST gene in one of the alleles. The irradiated Poinsettia plants were then recovered, potted and further cultivated using standard cultivation conditions in a greenhouse. The aim of the further treatment was to accumulate the mutated cell areas on mother plants grown from the irradiated Poinsettia plants. Therefore, developing shoot tips were classified as "normal" or "affected" by observation of distorted leaves. Such distortion served as marker for mutated regions. The uppermost leaf bud related to an affected leaf was identified and the shoot was pinched shortly above the identified bud using a scalpel. In case the shoot tips were completely normal, the whole side shoot was cut down to the lowest side bud. Bracts were removed that cover the centre of the plant and the lower side shoots or buds that were to develop.

After pinching, the plants were grown a further 5 weeks. The newly developed side shoots with 5 to 7 leaves were then subjected to the same pinching procedure as described above. This cycle was repeated two more times. Finally resulting side shoots were harvested, rooted and potted. These plants were grown for a period of 3, 4, 5, 6, 7 or even 8 weeks in long day conditions, meaning the day length was above 12 hours. After this period the plants were grown under short day conditions with an illumination period below 12 hours per day. After a period of further 6 to 8 weeks the upper leaves modified their colour from green to either red, pink, marble, shades and variations of these colours, or the desired white foliage.

The white bract, i.e. white foliage, may be only partial, further it may vary in its intensity. These plants were then selected from the plant stock and subjected to rejuvenation and further propagation with the aim to achieve a Poinsettia plant with pure white bracts and showing all the essential characteristics of the original elite Poinsettia plant. In the event that a white-bracted Poinsettia elite plant could not be obtained with a single irradiation treatment, the irradiation treatment was repeated until the desired white-bracted genotype was found.

Example 2: Molecular Selection of Heterozygous Elite Plant Material

Cross breeding in Poinsettia aims to the creation of superior red genotypes for commercialization. Pink, marble and white sports are generated by repeated rounds of irradiation. This is however only successful in genotypes with a heterozygous allele composition in the responsible gene for foliage colouration. The allele composition of this locus is usually unknown in the art. Using the current method, it is possible to perform a molecular test to elucidate the allelic composition of the responsible EpGST gene as a codominant SSR marker.

To this end, leaf material from each candidate plant was harvested. DNA was isolated from approximately 100 mg of leaf tissue using the NucleoSpin® Plant II kit (Macherey-Nagel GmbH & Co. KG, Germany) according to the manufacturer's instructions. DNA was analysed for the SSR marker by Polymerase Chain Reaction (PCR) using primers Ft (TGGCCTGCCTTTTAGAGAAA, SEQ ID NO: 60) and R (ACAAGTTCAGGGGGCTGAG, SEQ ID NO: 10).

The PCR reactions were performed in a 20 µl reaction containing 50 ng of DNA template, 1x Williams buffer, 0.15 mM of each dNTP, 0.25 µM of primer Ft, 0.25 µM of primer R and 1 u of DCSPol DNA Polymerase (DNA Cloning Service, Germany). The cycling conditions were 94° C. for 3 min; 30 cycles of 94° C. for 45 sec, 59° C. for 1 min and 72° C. for 1 min and 72° C. for 1 min; and a final extension of 10 min at 72° C. The PCR products were resolved in 6% (w/v) acrylamide gel in vertical electrophoresis using the LI-COR Gene Readir 4200 DNA Analyzer (LI-COR Biosciences, Nebraska, US) (FIG. 5A). The gels were subsequently stained with Ethidium bromide and the resulting band pattern was documented photographically. Alternatively, PCR products can be analysed by capillary electrophoresis on an ABI 3730 XL system at Microsynth AG (Balgach, Switzerland) (FIG. 5B).

These analyses resulted in the generation of a 195 bp DNA fragment in case of the unmutated EpGST allele, whereas the mutated allele resulted in a 191 bp DNA fragment, which could clearly be separated from the unmutated EpGST allele by the analysis methods (see for example FIGS. 3A and 3B).

Example 3: Generation of White-Bracted Poinsettia Elite Plants from Red-Bracted Elite Poinsettia Lines with Homozygous Composition of the GST Gene The commercial Poinsettia elite variety 'Christmas Aurora' (Klemm+Sohn) having a homozygous GST allele composition was chosen as starting point for targeted GST mutagenesis. The apical meristems of 30 Poinsettia young plants were irradiated with a total dosage of 15-50 Gray of X-ray radiation. The aim was to create single cells with a 4 bp mutation at the anthocyanin-related GST gene in one of the alleles. The irradiated Poinsettia plants were then recovered, potted and further cultivated using standard cultivation conditions in a greenhouse.

The aim of the further treatment was to accumulate the mutated cell areas on mother plants growing from the irradiated Poinsettia plants. Therefore, developing shoot tips were classified as "normal" or "affected" by observation of distorted leaves. Such distortion served as marker for mutated regions. The uppermost leaf bud related to an affected leaf was identified and the shoot was pinched shortly above the identified bud using a scalpel. In case the shoot tips were completely normal, the whole side shoot was cut down to the lowest side bud. Leaves were removed that cover the centre of the plant and the lower side shoots or buds that were to develop. After pinching, the plants were grown for a further 5 weeks. The newly developed side shoots with 5 to 7 leaves were then subjected to the same pinching procedure as described above. This cycle was repeated twice. Finally, resulting side shoots were harvested, rooted and potted. These plants were subjected to marker analysis described in the above example to detect heterozygous deletion mutants of the GST gene.

Figure 8:
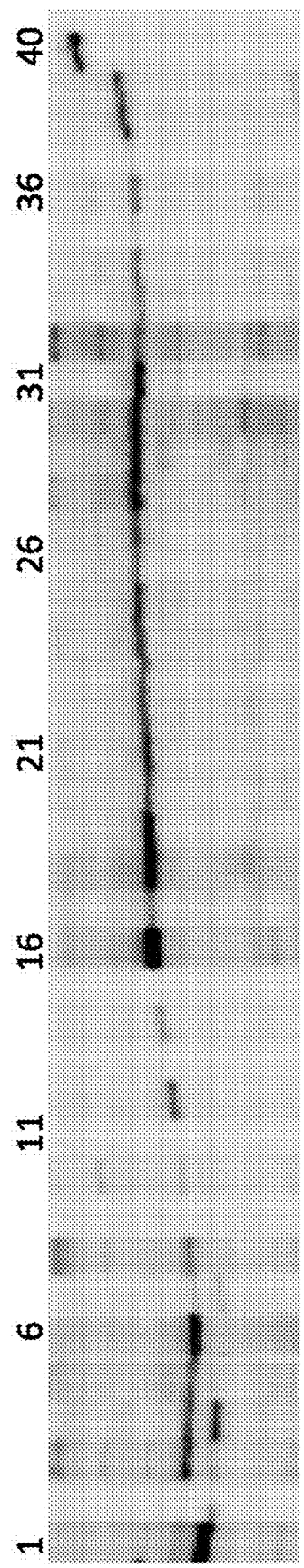
FIG. 8 shows the result of SSR marker genotyping of 35 plants recovered after irradiation of the homozygous red variety 'Christmas Aurora' (Klemm+Sohn), randomly selected out of 200 recovered plants. Lanes 1-5: controls (lane 1: white rr plant; lane 2: negative control; lane 3: red RR plant; lane 4: red Rr plant; lane 5: original variety Christmas Aurora); lanes 6-40: recovered candidate plants.

FIG. 8 shows the result of SSR marker genotyping of 35 plants recovered after irradiation of the homozygous red variety 'Christmas Aurora' (Klemm+Sohn), randomly selected out of 200 recovered plants. Lanes 1-5: controls (lane 1: white rr plant; lane 2: negative control; lane 3: red RR plant; lane 4: red Rr plant; lane 5: original variety 'Christmas Aurora'); lanes 6-40: recovered candidate plants.

Among 200 recovered plants, one line showed one mutated GST allele having the expected 4 bp deletion (FIG. 8, sample 7). Mutation frequency was confirmed to be one plant being uniformly heterozygous for the GST gene among 200 homozygous plants. The selected heterozygous plant was again subjected to the described irradiation treatment for one or several further cycles until the anthocyanin-related GST gene was homozygous for the 4 bp deletion in all tissue layers.

Example 4: Generation of White-Bracted Poinsettia Elite Plants Through UV Treatment Ultraviolet (UV) light, in particular UVA (320-400 nm) and UVB (290-320 nm), has strong genotoxic effects to induce mutations. Commercial Poinsettia elite lines having red-coloured bracts were chosen as starting point for targeted GST mutagenesis induced by UV irradiation. In a typical experiment the apical meristems of these Poinsettia young plants were exposed to UV radiation. The aim was to create single cells with a 4 bp mutation at the anthocyanin-related GST gene in one of the alleles. After the UV treatment the irradiated Poinsettia plants were recovered, potted and further cultivated using standard cultivation conditions in a greenhouse.

The aim of the further treatment was to accumulate the mutated cell areas on mother plants growing from the irradiated Poinsettia plants. The growing and selection procedures corresponded to the protocol for X-ray irradiated Poinsettia plants: Developing shoot tips were classified as "normal" or "affected" by observation of distorted leaves. Such distortion served as marker for mutated regions. The uppermost leaf bud related to an affected leaf was identified and the shoot was pinched shortly above the identified bud using a scalpel. In case the shoot tips were completely normal, the whole side shoot was cut down to the lowest side bud. Leaves were removed that cover the centre of the plant and the lower side shoots or buds that were to develop. After pinching, the plants were grown for a further 5 weeks. The newly developed side shoots with 5 to 7 leaves were then subjected to the same pinching procedure as described above. This cycle was repeated twice. Finally, resulting side shoots were harvested, rooted and potted. These plants were either selected by visual inspection or subjected to marker analysis.

For visual inspection, the said plants were grown under long days for a minimum of 3 weeks followed by a period of cultivation under short days for a minimum of 6 weeks to trigger the colouration of the bracts. At this stage, white-foliaged or partially white-foliaged plants became visible and were selected. Alternatively, the propagation material from irradiated plants was subjected to marker analysis to detect deletion mutants of the GST gene. Depending on the allele composition and the chimeric status of the starting plant material white-foliaged Poinsettia elite lines could be obtained with one or more cycles of UV treatment until the anthocyanin-related GST gene was homozygous for the 4 bp mutation in all tissue layers of the elite Poinsettia plant.

Example 5: Generation of Plants with a Mutant Anthocyanin-Related GST Gene Through EMS Mutagenesis Genetically stable changes in DNA sequence of plant genomes may also be induced by chemical agents. These include e.g. intercalating agents like ethidium bromide or alkylating agents like ethyl methane sulfonate (EMS). Chemical mutagenesis ideally is performed either on seeds or under aseptic conditions using tissue culture. A typical EMS mutagenesis experiment on a Poinsettia elite line starts from young shoots with minimum 4 nodal segments. After defoliation, the residual stems containing the apical meristem were surface-sterilized for 10 min. using 1.5% (v/v) sodium hypochloride with subsequent rinsing the stems with sterile water three times. These segments were then immersed in EMS solution. The concentration of EMS varied between 0.2-1% depending on the respective Poinsettia genotype. The addition of 2% DMSO improved the moistening of the plant material. The incubation time varied from 30 min. up to several hours again depending on the respective Poinsettia elite line.

After this treatment, the EMS solution was washed off in liquid growing media for 24 hrs, while the growing medium was exchanged twice. Then the nodal segments were transferred to growing medium according to Murashige & Skoog (MS) full-strengths medium, containing Vitamins after Nitsch, 30 g/l sucrose, 7.5 g/l plant agar and pH 5.8. No phytohormones were needed, neither for growing and propagating nor for rooting. The recovered Poinsettia plants were maintained in vitro by means of shoot cultures. The cultures were kept at 22° C. under reduced light conditions (approx. 10 $\mu mol \ast m^{-2} \ast sec^{-1}$) using Valoya L18 LED tubes with AP67 spectrum. Daily light period was 16 h. The further maintenance was done by sub-culturing the shoot tips and axillary nodes from in vitro plantlets using identical media and culture conditions.

The aim of these propagation cycles was to accumulate the mutated cell areas on the tissue culture shoots grown from the EMS treated Poinsettia stem segments. This sub-culture was repeated at least twice. Then the resulting shoots were analysed for mutations in the anthocyanin-related GST gene.

Example 6: Generation of Plants with a Mutant Anthocyanin-Related GST Gene Through Targeted Mutagenesis Plants with white foliage are also obtainable by a targeted mutagenesis of the anthocyanin-related GST gene using gene editing approaches like CRISPR/Cas. CRISPR/Cas constructs were used to generate mutations within the coding sequences of the EpGST gene. Target sequences located on the first exon of the EpGST were designed using standard web-based CRISPR/Cas designer tools, e.g. Chopchop (available on the world wide web at chopchop.cbu.uib.no). Candidate sequences were synthesized (Eurofins Genomics) as oligonucleotide pairs. Each oligonucleotide carried extra bases to allow the cloning of the target sequences at the BbsI site located between the U6-26 promoter and the sgRNA scaffold of the plant binary vector pEN-Sa-Chimera (Steinert et al., (2015) Plant J. 84:1295-1305). Resulting specific sgRNA was recombined into the destination vector pDe_Sacas) (available on the world wide web at botanik.kit.edu/molbio/) using the Golden Gate System following the manufacturer's instructions. All the cloning steps were done following standard procedures. Poinsettia genetic transformations were performed as described (Clarke et al., (2008) Plant Cell Rep 27(6):1027-1038) with *Agrobacterium tumefaciens* strain LBA4404 harbouring the generated CRISPR/Cas9 construct.

Regenerated embryos, approximately 0.5 cm tall, were transferred to a selective rooting medium containing 2 mg/l kanamycin and grown in a climate chamber (24-26° C., 16 h/8 h light). Only well-rooted plantlets were transferred to the greenhouse. Plants at the stadium of having 4-5 expanded leaves were screened for the presence of the Cas9/sgRNA cassette by PCR using the Phire Plant Direct PCR Kit (Thermo Fisher Scientific). The amplification reactions were assembled with M13(−21) as forward primer (GTAAAACGACGGCCAG, SEQ ID NO: 11), common to all reactions. The reverse primer Cas9-R (CCTACAGGGAATACCTCGAGAATAT, SEQ ID NO: 12) was specific for the Cas9/sgRNA cassette and consisted of the same oligonucleotide employed for cloning the guide RNA. Leaf samples from TO plants were analysed for mutations in the anthocyanin-related GST gene. Regenerated mutated Poinsettia plants were further cultivated under suitable greenhouse conditions and checked for white bracts.

Numbered Embodiments

Further embodiments contemplated by the disclosure are listed below.

1. The present disclosure relates to a method for the generation of a *Euphorbia pulcherrima* (Poinsettia) plant having a having a white foliage phenotype comprising the steps of: a. providing a target *E. pulcherrima* plant without a white foliage phenotype comprising in its genome at least one functional allele of a glutathione S-transferase gene (EpGST) comprising a simple sequence repeat (SSR) in the region encoding amino acids at positions 40-50 of the protein of SEQ ID NO: 3, comprising a stretch of 12 nucleotides consisting of a threefold CTTC repeat; b. subjecting said *E. pulcherrima* plant to a mutagenesis treatment to produce a mutant *E. pulcherrima* plant; c. selecting a mutant *E. pulcherrima* plant, wherein at least one allele of the EpGST gene comprises a CTTC deletion in said SSR motif; d. repeating steps b. and c. until all alleles of the EpGST gene in the plant genome comprise said CTTC deletion in said SSR motif; and e. selecting a *E. pulcherrima* plant having a white foliage phenotype, wherein said plant is homozygous for said CTTC deletion in said SSR motif.

2. In some embodiments, the present disclosure teaches a method for the generation of *E. pulcherrima* plants having a white foliage phenotype further comprising propagating said *E. pulcherrima* plant being homozygous for the EpGST gene comprising said CTTC deletion in said SSR motif and/or crossing said *E. pulcherrima* plant being homozygous for the EpGST gene comprising said CTTC deletion in said SSR motif with another *Euphorbia* sp. plant.

3. In some embodiments, the present disclosure teaches a method wherein said mutant *E. pulcherrima* plants without a white foliage phenotype are selected by a molecular marker suitable for the detection of said CTTC deletion in said SSR motif of the EpGST gene.

4. In some embodiments, the present disclosure teaches a method wherein the mutagenesis treatment is a human-induced random mutagenesis treatment selected from the group consisting of agents which cause a DNA double-strand break, ultraviolet (UV) irradiation, hydroxylamine, N-methyl-N'-nitro-N-nitrosoguanidine (MNNG), O-methyl hydroxylamine, nitrous acid, ethyl methane sulphonate (EMS), sodium bisulphite, formic acid, and nucleotide analogues.

5. In some embodiments, the present disclosure teaches a method wherein the functional EpGST gene in said target *E. pulcherrima* is selected from the group consisting of: a. A EpGST gene encoding the protein of SEQ ID NO: 3 and functional homologs or variants thereof having at least 60%, amino acid identity to SEQ ID NO: 3, wherein said homologs or variants have a first domain at positions 11-13 of SEQ ID NO: 3 being AAC, AGC or AAN, where N can be any amino acid (SEQ ID NO: 62), a second domain at positions 53-56 of SEQ ID NO: 3 being LVPA, QVPA (SEQ ID NO: 63) or QPVP (SEQ ID NO: 64), and a third amino acid domain at positions 65-68 of SEQ ID NO: 3 being FESR, b. A gene encoding an mRNA corresponding to the cDNA of SEQ ID NO: 2 and functional homologs or variants thereof having at least 90% nucleotide identity to SEQ ID NO: 2, wherein said homologs or variants comprises a stretch of 12 nucleotides consisting of a threefold CTTC repeat in the region of positions 118-150 of SEQ ID NO: 2, c. the EpGST gene of SEQ ID NO: 1 and functional homologs or variants thereof having at least 90% nucleotide identity to SEQ ID NO: 1, wherein said homolog or variant comprises a stretch of 12 nucleotides consisting of a threefold CTTC repeat in the region of positions 128-139 of SEQ ID NO: 1, and d. the EpGST gene of SEQ ID NO: 61 and functional homologs or variants thereof having at least 90% nucleotide identity to SEQ ID NO: 61, wherein said homolog or variant comprises a stretch of 12 nucleotides consisting of a threefold CTTC repeat in the region of positions 155-187 of SEQ ID No 61.

6. In some embodiments, the present disclosure teaches a method wherein the functional homolog or variant of the protein of SEQ ID NO: 3 further has at least one of a V on position 2 of SEQ ID NO: 3, a F or an L on position 62 of SEQ ID NO: 3, a LE on positions 90-91 of SEQ ID NO: 3, and an S on position 153 of SEQ ID NO: 3.

7. In some embodiments, the present disclosure relates to a plant or plant part having white foliage produced by the method disclosed herein, wherein said plant has all of the essential morphological and physiological traits of the target *E. pulcherrima* plant.

8. In some embodiments, the present disclosure teaches a white-foliaged *E. pulcherrima* plant derived from a non-white foliaged cultivated *E. pulcherrima* plant, wherein said non-white plant comprises in its genome a gene encoding a homolog or variant having at least 60% amino acid identity to SEQ ID NO: 3, said homolog or variant having a SSR comprising a stretch of 12 nucleotides consisting of a threefold CTTC repeat at positions 40-50 of the protein of SEQ ID NO: 3, wherein said derived white-foliaged E. pulcherrima plant comprises a CTTC deletion in said SSR, and wherein said white-foliaged E. pulcherrima plant is at least 99.9% genetically identical to said non-white foliaged E. pulcherrima plant.

9. In some embodiments, the present disclosure relates to white-foliaged E. pulcherrima plants, wherein said derived from non-white foliaged cultivated E. pulcherrima plant comprises in its genome a first domain at positions 11-13 of SEQ ID NO: 3 being AAC, AGC or AAN, where N can be any amino acid (SEQ ID NO: 62), a second domain at positions 53-56 of SEQ ID NO: 3 being LVPA, QVPA (SEQ ID NO: 63) or QPVP (SEQ ID NO: 64), and a third amino acid domain at positions 65-68 of SEQ ID NO: 3 being FESR.

10. In some embodiments, the present disclosure relates to seeds, plant parts, plant cells, or a plant population of a white-foliage E. pulcherrima plant.

11. In some embodiments, the present disclosure teaches a method for the generation of a E. pulcherrima plant having a having a white foliage phenotype comprising the steps of: a. providing a target E. pulcherrima plant without a white foliage phenotype comprising in its genome at least one dysfunctional allele of EpGST and one functional allele of EpGST; b. subjecting said E. pulcherrima plant to a mutagenesis treatment to produce a mutant E. pulcherrima plant; c. selecting a mutant E. pulcherrima plant having white foliage and wherein at least one allele of the EpGST gene comprises a CTTC deletion in the region encoding amino acids at positions 40-50 of the protein of SEQ ID NO: 3.

12. In some embodiments, the present disclosure relates to a method of use of the isolated DNA as described above as well as the sequences of SEQ ID NO: 44 to 49, or variants with at least 95% identity therewith for the preparation of a molecular marker as described above or for a method for targeted mutagenesis of a GST gene in a target plant.

13. In some embodiments, the present disclosure teaches a method further comprising propagating said E. pulcherrima plant having at least one allele of EpGST comprising said CTTC deletion and/or crossing said E. pulcherrima plant having at least one allele of EpGST comprising said CTTC deletion with another Euphorbia sp. plant.

14. In some embodiments, the present disclosure teaches a method wherein said mutant E. pulcherrima plants having white foliage are selected by a molecular marker suitable for the detection of said CTTC deletion in the EpGST gene.

15. In some embodiments, the present disclosure teaches a method of generating a E. pulcherrima plant with a white foliage phenotype, wherein said plant is derived from a white foliaged plant as first donor plant by breeding technologies with one or more non-white foliaged second donor E. pulcherrima plants comprising one or more elite properties, wherein said derived plant comprises one or more elite properties from the one or more second donor plants.

16. In some embodiments, the present disclosure relates to isolated nucleic acid of the EpGST gene described by SEQ ID NO: 61 or a variant thereof having at least 80% identity to the sequence described by SEQ ID NO: 1 and encoding a functional homolog or variant of the protein of SEQ ID NO: 3, wherein said homolog or variant has a first domain at positions 11-13 of SEQ ID NO: 3 being AAC, AGC or AAN, where N can be any amino acid (SEQ ID NO: 62), a second domain at positions 53-56 of SEQ ID NO: 3 being LVPA, QVPA (SEQ ID NO: 63) or QPVP (SEQ ID NO: 64), and a third amino acid domain at positions 65-68 of SEQ ID NO: 3 being FESR, and further comprising, in the region encoding amino acids at positions 40-50 of the protein of SEQ ID NO: 3, a stretch of 12 nucleotides consisting of a threefold CTTC repeat.

17. In some embodiments, the present disclosure teaches a method of use of the isolated nucleic acid for the preparation of a molecular marker or for a method for targeted mutagenesis of said EpGST gene.

18. In some embodiments, the present disclosure teaches a method wherein a continuous stretch of at least 17 nucleotides from any of the isolated DNA sequences is used to produce a guide RNA or an expression construct therefore for a CRISPR/Cas-based method of gene editing or to produce a silencing RNA or an expression construct therefore for a method of RNA-mediated gene silencing.

19. In some embodiments, the present disclosure teaches a method wherein the targeted mutagenesis is introduced by a DNA modification enzyme selected from the group consisting of meganucleases (MNs), zinc-finger nucleases (ZFNs), transcription-activator like effector nucleases (TALENs), Cas9 nuclease, Cpf1 nuclease (Cas12a), dCas9-FokI, dCpf1-FokI, chimeric Cas9-cytidine deaminase, chimeric Cas9-adenine deaminase, chimeric FEN1-FokI, and MegaTALs, a nickase Cas9 (nCas9), chimeric dCas9 non-FokI nuclease, dCpf1 non-FokI nuclease, chimeric Cpf1-cytidine deaminase, and Cpf1-adenine deaminase.

20. In some embodiments, the present disclosure teaches a method wherein the DNA sequence used to design a guide RNA is an 18-21 nucleotide sequence and is at least 90% identical to a target sequence.

21. In some embodiments, the present disclosure teaches a method wherein the target sequence is SEQ ID: 61.

22. In some embodiments, the present disclosure teaches a method of use of the isolated nucleic acid disclosed herein for the generation of a molecular marker, wherein said marker is capable of identifying a dysfunctional EpGST allele.

23. In some embodiments, the present disclosure relates to molecular markers which identify a CTTC deletion within positions 128-139 of the EpGST gene of SEQ ID NO: 1.

24. In some embodiments, the present disclosure teaches a method for producing a E. pulcherrima plant having a white foliage phenotype comprising: Screening a population of E. pulcherrima plants for dysfunctional GST using the markers disclosed herein; Selecting a first E. pulcherrima plant having at least one dysfunctional GST allele; Crossing said first selected E. pulcherrima plant having at least one dysfunctional GST allele with a second E. pulcherrima plant having at least one dysfunctional GST allele or itself to produce $F_1$ progeny; and Screening said $F_1$ progeny E. pulcherrima plants using said marker for homozygous dysfunctional GST alleles.

25. In some embodiments, the present disclosure relates to plants or plant parts having white foliage produced by marker-assisted breeding.

26. In some embodiments, the present disclosure teaches a method for the generation of a plant having dysfunctional glutathione S-transferase, comprising the steps of: providing a plant comprising in its genome at least one functional allele of a glutathione S-transferase (GST) gene, said GST gene comprising a simple sequence repeat (SSR) motif comprising a threefold CTTC repeat; subjecting said plant to a mutagen; selecting a mutant plant wherein at least one allele of the GST gene comprises a mutation in said SSR motif, wherein said mutation results in dysfunctional GST.

27. In some embodiments, the present disclosure relates to plants, seeds, plant parts, or a plant cell comprising at least one allele of the GST gene comprising a mutation in said SSR motif, and wherein mutation results in dysfunctional GST.

28. In some embodiments, the present disclosure teaches a method for the generation of a plant having dysfunctional GST, wherein the plant is selected from *Euphorbia pulcherrima*, and other petaloid bract species such as *Bougainvillea* and *Cornus*, *Arabidopsis thaliana*, *Phyllanthus angustifolius*, *Cyclamen*, *Vitis vinifera*, *Litchi chinensis*, and *Prunus persica* and hybrids thereof.

29. In some embodiments, the present disclosure relates to plants, seeds, plant parts, and plant cells having dysfunctional GST.

30. In some embodiments, the present disclosure teaches a method comprising applying plant breeding techniques to said mutant plants comprising dysfunctional GST, crossing, recurrent selection, mutation breeding, wherein said mutation breeding selects for a mutation that is spontaneous or artificially induced, backcrossing, pedigree breeding, marker enhanced selection, haploid/double haploid production, or transformation.

31. In some embodiments, the present disclosure teaches a method further comprising vegetatively propagating said mutant plant.

32. In some embodiments, the present disclosure teaches a method wherein the mutagen is a human-induced random mutagenesis treatment selected from the group consisting of radiation, temperature, long-term seed storage, tissue culture conditions, and chemical mutagens.

33. In some embodiments, the present disclosure teaches a method wherein said radiation is selected from the group comprising X-rays, Gamma rays, neutrons, Beta radiation, and ultraviolet radiation.

34. In some embodiments, the present disclosure teaches a method for producing a plant having dysfunctional GST comprising: Screening a population of plants for dysfunctional GST; Selecting a first plant having at least one dysfunctional GST allele; Crossing said first selected plant having at least one dysfunctional GST allele with a second plant having at least one dysfunctional GST allele or itself to produce F1 progeny; and Screening said F1 progeny plants for homozygous dysfunctional GST alleles.

35. In some embodiments, the present disclosure relates to a plant, plant part, or plant cell produced by the method disclosed herein.

36. In some embodiments, the present disclosure teaches a method wherein said screening is selected from the group comprising molecular markers, biochemical assays, and the genetic complementation assay.

37. In some embodiments, the present disclosure teaches a method wherein the molecular markers correspond the PCR primers of SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, or combinations thereof.

38. In some embodiments, the present disclosure teaches a method further comprising a human-induced random mutagenesis treatment selected from the group consisting of radiation, temperature, long-term seed storage, tissue culture conditions, and chemical mutagens.

39. In some embodiments, the present disclosure teaches a method of editing a GST gene of a plant, wherein said method is selected from the group comprising zinc finger nucleases, transcription activator-like effector nucleases (TALENs), engineered homing endonucleases/meganucleases, and the clustered regularly interspaced short palindromic repeat (CRISPR)-associated protein9 (Cas9) system.

40. In some embodiments, the present disclosure relates to plants wherein said GST gene is a homolog or variant of the protein of SEQ ID NO: 3 with at least 60% amino acid identity, wherein said homolog or variant has a first domain at positions 11-13 of SEQ ID NO: 3 being AAC, AGC or AAN, where N can be any amino acid (SEQ ID NO: 62), a second domain at positions 53-56 of SEQ ID NO: 3 being LVPA, QVPA (SEQ ID NO: 63) or QPVP (SEQ ID NO: 64), and a third domain at positions 65-68 of SEQ ID NO: 3 being FESR.

41. In some embodiments, the present disclosure relates to plants wherein said functional homolog or variant of the protein of SEQ ID NO: 3 further has a V on position 2 of SEQ ID NO: 3, and/or an F or an L on position 62 of SEQ ID NO: 3, and/or LE on positions 90-91 of SEQ ID NO: 3, and/or an S on position 153 of SEQ ID NO: 3.

42. In some embodiments, the present disclosure relates to a molecular marker or method of targeted mutatgenesis comprising continuous stretch of at least 17 nucleotides from any isolated DNA sequences disclosed herein to (a) produce a guide RNA or an expression construct therefor for a CRISPR/Cas-based method of gene editing or (b) produce a silencing RNA or an expression construct therefor for a method of RNA-mediated gene silencing.

43. In some embodiments, the present disclosure also teaches a method for the production of plants having a reduced level of anthocyanins comprising the steps of: a. providing a plant comprising in its genome at least one functional copy of a glutathione S-transferase GST gene encoding a protein selected from the group consisting of SEQ ID NO: 3, and 53 to 59 or encoding a functional homolog or variant of said protein with at least 60%, amino acid identity, the homolog or variant having a first domain corresponding to positions 11-13 of SEQ ID NO: 3 being AAC, AGC or AAN, where N can be any amino acid (SEQ ID NO: 62), a second domain corresponding to positions 53-56 of SEQ ID NO: 3 being LVPA, QVPA (SEQ ID NO: 63) or QPVP (SEQ ID NO: 64), and a third amino acid domain corresponding to positions 65-68 of SEQ ID NO: 3 being FESR; b. subjecting the plant of step a. to targeted mutagenesis treatment to produce a mutant GST gene therein, and c. selecting a plant with reduced level of anthocyanins being homozygous for mutated GST gene.

44. In some embodiments, the present disclosure relates to mutations in the GST gene, wherein the mutations are selected from the group consisting of a loss-of-function mutation, a partial loss-of-function mutation, a restored frameshift mutation, an in-frame deletion mutation, or a promoter deletion.

45. In some embodiments, the present disclosure teaches a method of GST mutagenesis involving the use of at least one DNA sequence selected from the group consisting of: (i) the sequences of any of the claims 11-13, (ii) the sequences of SEQ ID NO: 44 to 49, or variants thereof with at least 95% identity, (iii) the complements to the sequences under (i) and (ii), and (iv) a fragment of the sequences under (i) to (iii) of at least 17 contiguous nucleotides, wherein said DNA sequence is used to produce a guide RNA targeting GST.

46. In some embodiments, the present disclosure relates to isolated nucleic acid having at least 80% identity to the sequence described by SEQ ID NO: 1 and encoding a functional homolog or variant of the protein of SEQ ID NO: 3, wherein said isolated nucleic acid selected from the group consisting of SEQ ID NO: 44, SEQ ID NO: 45, SEQ ID NO:

46, SEQ ID NO: 47, SEQ ID NO: 48, SEQ ID NO: 49, or variants thereof with at least 95% identity.

47. In some embodiments, the present disclosure teaches a white-foliaged *E. pulcherrima* plant derived from a non-white foliaged cultivated *E. pulcherrima* plant, wherein said non-white plant comprises in its genome a gene encoding a homolog or variant having at least 60% amino acid identity to SEQ ID NO: 3, said homolog or variant having a SSR comprising a stretch of 12 nucleotides consisting of a threefold CTTC repeat at positions 40-50 of the protein of SEQ ID NO: 3, wherein said derived white-foliaged *E. pulcherrima* plant comprises a CTTC deletion in said SSR, and wherein said white-foliaged *E. pulcherrima* plant is at least 99.9% genetically identical to said non-white foliaged *E. pulcherrima* plant, and wherein the less than 0.1% changes are limited to (i) the CTTC deletions, (ii) any off-target genetic change caused by method of mutagenesis and (iii) any genetic changes occurring during asexual propagation of said plant.

48. In some embodiments, the present disclosure teaches a method for producing a plant having reduced levels of anthocyanins comprising: a. Providing a plant comprising in its genome at least one functional allele of a glutathione S-transferase gene; b. subjecting said plant to targeted mutagenesis treatment to produce a mutant GST gene therein, wherein said mutation is selected from the group consisting of loss-of-function, partial loss-of-function, a restored frameshift, an in-frame deletion, or a promoter deletion, and wherein said targeted mutagenesis uses at least one of the sequences of SEQ ID NO: 44-49, or variants thereof having at least 95% identity, to produce a guide RNA; and; c. selecting a plant having reduced levels of anthocyanins.

While a number of exemplary aspects and embodiments have been discussed above, those of skill in the art will recognize certain modifications, permutations, additions, and sub-combinations thereof. It is therefore intended that the following appended claims and claims hereafter are interpreted to include all such modifications, permutations, additions, and sub-combinations as are within their true spirit and scope.

The invention claimed is:

1. A method for the generation of a *Euphorbia pulcherrima* plant having a white foliage phenotype comprising the steps of:
   a) selecting a target *E. pulcherrima* plant which comprises in its genome at least one dysfunctional allele of a glutathione S-transferase gene (EpGST) comprising a CTTC deletion in a simple sequence repeat (SSR) in the region encoding amino acids at positions 40-50 of the functional EpGST protein of SEQ ID NO: 3, comprising a stretch of 12 nucleotides consisting of a threefold CTTC repeat, wherein the selecting comprises using a molecular marker suitable to detect the presence or absence of a CTTC deletion in said SSR motif of the EpGST gene;
   b) subjecting the target *E. pulcherrima* plant to a mutagenesis treatment to produce a mutant *E. pulcherrima* plant;
   c) selecting a white foliaged *E. pulcherrima* plant homozygous for said CTTC deletion in said SSR motif.

2. The method of claim 1, wherein step b) is repeated with a selection step using said molecular marker.

3. The method of claim 1, further comprising propagating said white foliaged *E. pulcherrima* plant.

4. The method of claim 1, further comprising crossing said white foliaged *E. pulcherrima* plant with another *Euphorbia* sp. plant.

5. The method of claim 1, wherein the mutagenesis treatment is a human-induced random mutagenesis treatment selected from the group consisting of agents which cause a DNA double-strand break, ultraviolet (UV) irradiation, hydroxylamine, N-methyl-N'-nitro-N-nitrosoguanidine (MNNG), O-methyl hydroxylamine, nitrous acid, ethyl methane sulphonate (EMS), sodium bisulphite, formic acid, and nucleotide analogues.

6. A method for the generation of a *Euphorbia pulcherrima* plant having a white foliage phenotype comprising the steps of:
   a) providing a target *E. pulcherrima* plant without a white foliage phenotype comprising in its genome at least one functional allele of a glutathione S-transferase gene (EpGST) comprising a simple sequence repeat (SSR) in the region encoding amino acids at positions 40-50 of the protein of SEQ ID NO: 3, comprising a stretch of 12 nucleotides consisting of a threefold CTTC repeat;
   b) subjecting said *E. pulcherrima* plant to a mutagenesis treatment to produce a mutant *E. pulcherrima* plant;
   c) selecting a mutant *E. pulcherrima* plant, wherein at least one allele of the EpGST gene comprises a CTTC deletion in said SSR motif, wherein the selecting comprises using a molecular marker suitable for the detection of said CTTC deletion in said SSR motif of the EpGST gene;
   d) repeating steps b) and c) until all alleles of the EpGST gene in the plant genome comprise said CTTC deletion in said SSR motif; and
   e) selecting a white foliaged *E. pulcherrima* plant homozygous for said CTTC deletion in said SSR motif.

7. The method of claim 6, wherein the functional EpGST gene in said target *E. pulcherrima* is selected from the group consisting of:
   a) an EpGST gene encoding the protein of SEQ ID NO: 3 and functional homologs or variants thereof having at least 90%, amino acid identity to SEQ ID NO: 3;
   b) a gene encoding an mRNA corresponding to the cDNA of SEQ ID NO: 2 and functional homologs or variants thereof having at least 90% nucleotide identity to SEQ ID NO: 2;
   c) the EpGST gene of SEQ ID NO: 1 and functional homologs or variants thereof having at least 90% nucleotide identity to SEQ ID NO: 1; and
   d) the EpGST gene of SEQ ID NO: 61 and functional homologs or variants thereof having at least 90% nucleotide identity to SEQ ID NO: 61.

8. The method of claim 7, wherein said homologs or variants have a first domain at positions 11-13 of SEQ ID NO: 3 being AAC, AGC or AAN, where N can be any amino acid (SEQ ID NO: 62), a second domain at positions 53-56 of SEQ ID NO: 3 being LVPA, QVPA (SEQ ID NO: 63) or QPVP (SEQ ID NO: 64), and a third amino acid domain at positions 65-68 of SEQ ID NO: 3 being FESR.

9. The method of claim 8, wherein the functional homolog or variant of the protein of SEQ ID NO: 3 further has at least one of a V at position 2 of SEQ ID NO: 3, an F or an L at position 62 of SEQ ID NO: 3, an LE at positions 90-91 of SEQ ID NO: 3, and an S at position 153 of SEQ ID NO: 3.

10. The method of claim 6, wherein the molecular marker is a PCR product produced using any one of the following PCR primers: SEQ ID NO: 4, SEQ ID NO: 5, SEQ ID NO: 6, SEQ ID NO: 7, SEQ ID NO: 8, SEQ ID NO: 10, and combinations thereof.

* * * * *

SEQUENCE LISTING

```
<160> NUMBER OF SEQ ID NOS: 64

<210> SEQ ID NO 1
<211> LENGTH: 2314
<212> TYPE: DNA
<213> ORGANISM: Euphorbia pulcherrima

<400> SEQUENCE: 1
atggtagtga aagtgtatgg agcagctcag gcagcttgcc cacaaagagt aatggcctgc      60
cttttagaga aagatattcc ttttgatctt gttcatgttg atcttccttc tgctcaacat     120
aaactctctt ccttccttct caaacaggtt ctttacttcc ctttttttac tatacatttc     180
ttctaggcct aatatacatc tagacccoct atagttgttc ctgaaaaccc ctcagccccc     240
tgaacttgtt aaagtggatc ttacagcccc ttaaacttgg tcaaactgaa cctcaaaacc     300
ccttaatggt aacatgccca gttttgttcc ggtaaatcag ttttcgattc aatctttgac     360
gaaacaatct tagattcaat ctttagaaaa ataatacttg acatatcagc atcaagcggc     420
tatggggttc acttttaaca agttcagggt gctataaagt ccactttaat aaattcaggg     480
ttaaggatac cttttgtaag tttaggtggt tgaggggttt taagggaact ataggaggcc     540
tagatttatt agctctcttg tttgatgtca caattaatta tgtttattta tttattctgt     600
agccctttgg gttagttcca gctatagaag atggggattt caggcttttt ggtatgtttc     660
ttaatctttt catttcagtg atagccctca gtatttcgtt ttactaagat ttcgggacca     720
caattcgttt ttgtagtgtc actatggata attgttaaaa atgagacatg tacaaaacaa     780
atcctattcg aatcttctat cgttggtcat aaccacatgg atatctacgc ataaaaatac     840
caaaaaatat tttaacatgt acatgttctt ttgtattccg tccactattt cgataagcat     900
cgatttatcg ttttttggct ttaaattata atggactaaa ctaaaatgat tcattaaact     960
gtctgaactt ctttattgtg aaatcacgga tagctgttgc aactccactt cagggtcaat    1020
tggaaacaac atctctgtaa ttacatgggt aaggctgcat acactcaacc ccccgacact    1080
gcttgtgagg gagccttatt aggcattggg gtgatgttgt tgttttacac gttattttgt    1140
atcattgtaa tctatcaaac tattataatt acttattacc aagtataatt tattacattg    1200
attaaagtat aatttattcc actaaattta tgttttatgc accttacccct gaactttgat    1260
```

-continued

```
tttttattta gtattataaa atgttgttta agtaaataaa atagatacta tttaaaaata   1320
atttagaaaa aaataataaa atagagcaag gtctccatac aaaaccatcg tacttatttg   1380
aacagatata tatgtagtgt tattcatatt ttttttttata ataacataga actgatgaat   1440
ctggattaga aatgatgata taatggcttg cctcattcac gatcacacaa ttgataagtc   1500
tgattttacc aacaaatatc agttttcaa tattatgtgt tgctattttc ttgaagaaga   1560
aattttgcac gaccatattt aagaataggc ttagattgat cggtcaaaca aaatcttagg   1620
ttattttttc attttccttt tctcattagt tagaatcaaa atttggaatt aaattttttg   1680
ttttaatttt acttctaact attgagatca tatatcacca aatatatgct ttctttatta   1740
tttctacata aaaaaatata tggttttaca actacctaac tatgctttt tttaaagttt    1800 gcctcattag gcttacaact accaaactat gttgaattaa tataattttg tttgtgtgtg   1860
tgaagaatca agagccataa tgagatacta tgcaacaaaa tatgaagaaa gagggcccaa   1920
tttgttagga aaaacattag aagagaaagc aatagttgat caatgggttg aagtggaagc   1980
ccataatttc aataatttgg tttacaatat tgtaattgaa gttttgataa agccaaaaat   2040 ggggaacaa ggtgacatca acatagtcaa aagctgtgaa cataagctgg ataaagtgtt    2100
cgatgtgtac gaggaaaggc tatccagttc caaatatctt ggaggagatt atttcacact   2160
tgctgattta acccatatgc cttccattag gtaccttgtt catgagcttg ggttagccca   2220
tttggttcac aatagaaaca aggtcaatgc ttggtggatt gatatatcgg accgaccggc   2280
ttggaaaaat ttgatgattc ttgctggtta ttag                               2314
```

```
<210> SEQ ID NO 2
<211> LENGTH: 645
<212> TYPE: DNA
<213> ORGANISM: Euphorbia pulcherrima

<400> SEQUENCE: 2
```

```
atggtagtga aagtgtatgg agcagctcag gcagcttgcc cacaaagagt aatggcctgc    60
cttttagaga aagatattcc ttttgatctt gttcatgttg atcttccttc tgctcaacat   120
aaactctctt ccttccttct caaacagccc tttgggttag ttccagctat agaagatggg   180
gatttcaggc ttttgaatc aagagccata atgagatact atgcaacaaa atatgaagaa    240
agagggccca atttgttagg aaaaacatta gaagagaaag caatagttga tcaatgggtt   300
gaagtggaag cccataattt caataatttg gtttacaata ttgtaattga agttttgata   360
aagccaaaaa tggggaaca aggtgacatc aacatagtca aaagctgtga acataagctg    420
gataaagtgt tcgatgtgta cgaggaaagg ctatccagtt ccaaatatct tggaggagat   480
tatttcacac ttgctgattt aacccatatg ccttccatta ggtaccttgt tcatgagctt   540
gggttagccc atttggttca atagaaac aaggtcaatg cttggtggat tgatatatcg     600
gaccgaccgg cttggaaaaa tttgatgatt cttgctggtt attag                   645
```

```
<210> SEQ ID NO 3
<211> LENGTH: 214
<212> TYPE: PRT
<213> ORGANISM: Euphorbia pulcherrima

<400> SEQUENCE: 3
```

```
Met Val Val Lys Val Tyr Gly Ala Ala Gln Ala Ala Cys Pro Gln Arg
1               5                   10                  15

Val Met Ala Cys Leu Leu Glu Lys Asp Ile Pro Phe Asp Leu Val His
            20                  25                  30
```

```
Val Asp Leu Pro Ser Ala Gln His Lys Leu Ser Ser Phe Leu Leu Lys
        35                  40                  45

Gln Pro Phe Gly Leu Val Pro Ala Ile Glu Asp Gly Asp Phe Arg Leu
 50                  55                  60

Phe Glu Ser Arg Ala Ile Met Arg Tyr Tyr Ala Thr Lys Tyr Glu Glu
 65                  70                  75                  80

Arg Gly Pro Asn Leu Leu Gly Lys Thr Leu Glu Glu Lys Ala Ile Val
                 85                  90                  95

Asp Gln Trp Val Glu Val Glu Ala His Asn Phe Asn Asn Leu Val Tyr
            100                 105                 110

Asn Ile Val Ile Glu Val Leu Ile Lys Pro Lys Met Gly Glu Gln Gly
        115                 120                 125

Asp Ile Asn Ile Val Lys Ser Cys Glu His Lys Leu Asp Lys Val Phe
130                 135                 140

Asp Val Tyr Glu Glu Arg Leu Ser Ser Ser Lys Tyr Leu Gly Gly Asp
145                 150                 155                 160

Tyr Phe Thr Leu Ala Asp Leu Thr His Met Pro Ser Ile Arg Tyr Leu
                165                 170                 175

Val His Glu Leu Gly Leu Ala His Leu Val His Asn Arg Asn Lys Val
            180                 185                 190

Asn Ala Trp Trp Ile Asp Ile Ser Asp Arg Pro Ala Trp Lys Asn Leu
        195                 200                 205

Met Ile Leu Ala Gly Tyr
    210

<210> SEQ ID NO 4
<211> LENGTH: 23
<212> TYPE: DNA
<213> ORGANISM: artificial
<220> FEATURE:
<223> OTHER INFORMATION: amplification primer

<400> SEQUENCE: 4
tccgatctaa gaaatcaagg cta                                           23

<210> SEQ ID NO 5
<211> LENGTH: 20
<212> TYPE: DNA
<213> ORGANISM: artificial
<220> FEATURE:
<223> OTHER INFORMATION: amplification primer

<400> SEQUENCE: 5
cagtcggccg ctacatagat                                               20

<210> SEQ ID NO 6
<211> LENGTH: 20
<212> TYPE: DNA
<213> ORGANISM: artificial
<220> FEATURE:
<223> OTHER INFORMATION: amplification primer

<400> SEQUENCE: 6
tggcctgcct tttagagaaa                                               20

<210> SEQ ID NO 7
<211> LENGTH: 20
<212> TYPE: DNA
<213> ORGANISM: artificial
<220> FEATURE:
```

<223> OTHER INFORMATION: amplification primer

<400> SEQUENCE: 7
aaagcctgaa atccccatct                                                    20

<210> SEQ ID NO 8
<211> LENGTH: 20
<212> TYPE: DNA
<213> ORGANISM: artificial
<220> FEATURE:
<223> OTHER INFORMATION: amplification primer

<400> SEQUENCE: 8
tatgggcttc cacttcaacc                                                    20

<210> SEQ ID NO 9
<211> LENGTH: 37
<212> TYPE: DNA
<213> ORGANISM: artificial
<220> FEATURE:
<223> OTHER INFORMATION: amplification primer

<400> SEQUENCE: 9
gtaaaacgac ggccagttgg cctgcctttt agagaaa                                 37

<210> SEQ ID NO 10
<211> LENGTH: 19
<212> TYPE: DNA
<213> ORGANISM: artificial
<220> FEATURE:
<223> OTHER INFORMATION: amplification primer

<400> SEQUENCE: 10
acaagttcag ggggctgag                                                     19

<210> SEQ ID NO 11
<211> LENGTH: 16
<212> TYPE: DNA
<213> ORGANISM: artificial
<220> FEATURE:
<223> OTHER INFORMATION: amplification primer

<400> SEQUENCE: 11
gtaaaacgac ggccag                                                        16

<210> SEQ ID NO 12
<211> LENGTH: 25
<212> TYPE: DNA
<213> ORGANISM: artificial
<220> FEATURE:
<223> OTHER INFORMATION: amplification primer

<400> SEQUENCE: 12
cctacaggga atacctcgag aatat                                              25

<210> SEQ ID NO 13
<211> LENGTH: 645
<212> TYPE: DNA
<213> ORGANISM: Euphorbia pulcherrima var. Feelings Red

<400> SEQUENCE: 13
atggtagtga aagtgtatgg agcagctcag gcagcttgcc cacaaagagt aatggcctgc        60
cttttagaga aagatattcc ttttgatctt gttcatgttg atcttccttc tgctcaacat       120
aaactctctt ccttccttct caaacagccc tttgggttag ttccagctat agaagatggg       180

```
gatttcaggc tttttgaatc aagagccata atgagatact atgcaacaaa atatgaagaa        240
agagggccca atttgttagg aaaaacatta gaagagaaag caatagttga tcaatgggtt        300
gaagtggaag cccataattt caataatttg gtttacaata ttgtaattga agttttgata        360
aagccaaaaa tgggggaaca aggtgacatc aacatagtca aaagctgtga acataagctg        420
gataaagtgt tcgatgtgta cgaggaaagg ctatccagtt ccaaatatct tggaggagat        480
tatttcacac ttgctgattt aacccatatg ccttccatta ggtaccttgt tcatgagctt        540
gggttagccc atttggttca caatagaaac aaggtcaatg cttggtggat tgatatatcg        600
gaccgaccgg cttggaaaaa tttgatgatt cttgctggtt attag                       645
```

<210> SEQ ID NO 14
<211> LENGTH: 645
<212> TYPE: DNA
<213> ORGANISM: Euphorbia pulcherrima var. Glory Red

<400> SEQUENCE: 14

```
atggtagtga aagtgtatgg agcagctcag gcagcttgcc cacaaagagt aatggcctgc         60
cttttagaga aagatattcc ttttgatcta gttcatgttg atcttccttc tgctcaacac        120
aaactctctt ccttccttct caaacagcca tttgggttag ttccagctat agaagatggg        180
gatttcaggc tttttgaatc aagagccata atgagatact atgcaacaaa atatgaagaa        240
agagggccca atttgttagg aaaaacatta gaagagaaag caatagttga tcaatgggtt        300
gaagtggaag cccataattt caataatttg gtttacaata ttgtaattga agttttgata        360
aagccaaaaa tgggggaaca aggtgacatc aacatagtca aaagctgtga acataagctg        420
gataaagtgt tcgatgtgta cgaggaaagg ctatccagtt ccaaatatct tggaggagat        480
tatttcacac ttgctgattt aacccatatg ccttccatta ggtatcttgt tcatgagctt        540
gggttagccc atttggttca caatagaaac aaggtcagtg cttggtggat tgatatatcg        600
gacagaccgg cttggaaaaa tttgatgatt cttgctggtt attag                       645
```

<210> SEQ ID NO 15
<211> LENGTH: 645
<212> TYPE: DNA
<213> ORGANISM: Euphorbia pulcherrima var. Joy Red

<400> SEQUENCE: 15

```
atggtagtga aagtgtatgg agcagctcag gcagcttgcc cacaaagagt aatggcctgc         60
cttttagaga aagatattcc ttttgatctt gttcatgttg atcttccttc tgctcaacat        120
aaactctctt ccttccttct caaacagccc tttgggttag ttccagctat agaagatggg        180
gatttcaggc tttttgaatc aagagccata atgagatact atgcaacaaa atatgaagaa        240
agagggccca atttgttagg aaaaacatta gaagagaaag caatagttga tcaatgggtt        300
gaagtggaag cccataattt caataatttg gtttacaata ttgtaattga agttttgata        360
aagccaaaaa tgggggaaca aggtgacatc aacatagtca aaagctgtga acataagctg        420
gataaagtgt tcgatgtgta cgaggaaagg ctatccagtt ccaaatatct tggaggagat        480
tatttcacac ttgctgattt aacccatatg ccttccatta ggtaccttgt tcatgagctt        540
gggttagccc atttggttca caatagaaac aaggtcaatg cttggtggat tgatatatcg        600
gaccgaccgg cttggaaaaa tttgatgatt cttgctggtt attag                       645
```

<210> SEQ ID NO 16

<211> LENGTH: 645
<212> TYPE: DNA
<213> ORGANISM: Euphorbia pulcherrima var. Titan Red

<400> SEQUENCE: 16

```
atggtagtga aagtgtatgg agcagctcag gcagcttgcc cacaaagagt aatggcctgc      60
cttttagaga aagatattcc ttttgatctt gttcatgttg atcttccttc tgctcaacat     120
aaactctctt ccttccttct caaacagccc tttgggttag ttccagctat agaagatggg     180
gatttcaggc ttttttgaatc aagagccata atgagatact atgcaacaaa atatgaagaa    240
agagggccca atttgttagg aaaaacatta gaagagaaag caatagttga tcaatgggtt     300
gaagtggaag cccataattt caataatttg gtttacaata ttgtaattga agttttgata     360
aagccaaaaa tggggaaaca aggtgacatc aacatagtca aaagctgtga acataagctg     420
gataaagtgt tcgatgtgta cgaggaaagg ctatccagtt ccaaatatct tggaggagat     480
tatttcacac ttgctgattt aacccatatg ccttccatta ggtaccttgt tcatgagctt     540
gggttagccc atttggttca caatagaaac aaggtcaatg cttggtggat tgatatatcg     600
gaccgaccgg cttggaaaaa tttgatgatt cttgctggtt attag                     645
```

<210> SEQ ID NO 17
<211> LENGTH: 645
<212> TYPE: DNA
<213> ORGANISM: Euphorbia pulcherrima var. Bravo Red

<400> SEQUENCE: 17

```
atggtagtga aagtgtatgg agcagctcag gcagcttgcc cacaaagagt aatggcctgc      60
cttttagaga aagatattcc ttttgatcta gttcatgttg atcttccttc tgctcaacac     120
aaactctctt ccttccttct caaacagcca tttgggttag ttccagctat agaagatggg     180
gatttcaggc ttttttgaatc aagagccata atgagatact atgcaacaaa atatgaagaa    240
agagggccca atttgttagg aaaaacatta gaagagaaag caatagttga tcaatgggtt     300
gaagtggaag cccataattt caataatttg gtttacaata ttgtaattga agttttgata     360
aagccaaaaa tggggaaaca aggtgacatc aacatagtca aaagctgtga acataagctg     420
gataaagtgt tcgatgtgta cgaggaaagg ctatccagtt ccaaatatct tggaggagat     480
tatttcacac ttgctgattt aacccatatg ccttccatta ggtatcttgt tcatgagctt     540
gggttagccc atttggttca caatagaaac aaggtcagtg cttggtggat tgatatatcg     600
gacagaccgg cttggaaaaa tttgatgatt cttgctggtt attag                     645
```

<210> SEQ ID NO 18
<211> LENGTH: 645
<212> TYPE: DNA
<213> ORGANISM: Euphorbia pulcherrima var. SK130 Red

<400> SEQUENCE: 18

```
atggtagtga aagtgtatgg agcagctcag gcagcttgcc cacaaagagt aatggcctgc      60
cttttagaga aagatattcc ttttgatctt gttcatgttg atcttccttc tgctcaacat     120
aaactctctt ccttccttct caaacagccc tttgggttag ttccagctat agaagatggg     180
gatttcaggc ttttttgaatc aagagccata atgagatact atgcaacaaa atatgaagaa    240
agagggccca atttgttagg aaaaacatta gaagagaaag caatagttga tcaatgggtt     300
gaagtggaag cccataattt caataatttg gtttacaata ttgtaattga agttttgata     360
aagccaaaaa tggggaaaca aggtgacatc aacatagtca aaagctgtga acataagctg     420
```

```
gataaagtgt tcgatgtgta cgaggaaagg ctatccagtt ccaaatatct tggaggagat    480
tatttcacac ttgctgattt aacccatatg ccttccatta ggtaccttgt tcatgagctt    540
gggttagccc atttggttca caatagaaac aaggtcaatg cttggtggat tgatatatcg    600
gaccgaccgg cttggaaaaa tttgatgatt cttgctggtt attag                   645
```

<210> SEQ ID NO 19
<211> LENGTH: 641
<212> TYPE: DNA
<213> ORGANISM: Euphorbia pulcherrima var. Feelings White

<400> SEQUENCE: 19

```
atggtagtga aagtgtatgg agcagctcag gcagcttgcc cacaaagagt aatggcctgc    60
cttttagaga aagatattcc ttttgatctt gttcatgttg atcttccttc tgctcaacat   120
aaactctctt ccttctcaaa cagccctttg ggttagttcc agctatagaa gatggggatt   180
tcaggctttt tgaatcaaga gccataatga gatactatgc aacaaaatat gaagaaagag   240
ggcccaattt gttaggaaaa acattagaag agaaagcaat agttgatcaa tgggttgaag   300
tggaagccca taatttcaat aatttggttt acaatattgt aattgaagtt ttgataaagc   360
caaaaatggg ggaacaaggt gacatcaaca tagtcaaaag ctgtgaacat aagctggata   420
aagtgttcga tgtgtacgag gaaaggctat ccagttccaa atatcttgga ggagattatt   480
tcacacttgc tgatttaacc catatgcctt ccattaggta ccttgttcat gagcttgggt   540
tagcccattt ggttcacaat agaaacaagg tcaatgcttg gtggattgat atatcggacc   600
gaccggcttg gaaaaatttg atgattcttg ctggttatta g                        641
```

<210> SEQ ID NO 20
<211> LENGTH: 641
<212> TYPE: DNA
<213> ORGANISM: Euphorbia pulcherrima var. Glory White

<400> SEQUENCE: 20

```
atggtagtga aagtgtatgg agcagctcag gcagcttgcc cacaaagagt aatggcctgc    60
cttttagaga aagatattcc ttttgatctt gttcatgttg atcttccttc tgctcaacat   120
aaactctctt ccttctcaaa cagccctttg ggttagttcc agctatagaa gatggggatt   180
tcaggctttt tgaatcaaga gccataatga gatactatgc aacaaaatat gaagaaagag   240
ggcccaattt gttaggaaaa acattagaag agaaagcaat agttgatcaa tgggttgaag   300
tggaagccca taatttcaat aatttggttt acaatattgt aattgaagtt ttgataaagc   360
caaaaatggg ggaacaaggt gacatcaaca tagtcaaaag ctgtgaacat aagctggata   420
aagtgttcga tgtgtacgag gaaaggctat ccagttccaa atatcttgga ggagattatt   480
tcacacttgc tgatttaacc catatgcctt ccattaggta ccttgttcat gagcttgggt   540
tagcccattt ggttcacaat agaaacaagg tcaatgcttg gtggattgat atatcggacc   600
gaccggcttg gaaaaatttg atgattcttg ctggttatta g                        641
```

<210> SEQ ID NO 21
<211> LENGTH: 641
<212> TYPE: DNA
<213> ORGANISM: Euphorbia pulcherrima var. Joy White

<400> SEQUENCE: 21

```
atggtagtga aagtgtatgg agcagctcag gcagcttgcc cacaaagagt aatggcctgc    60
```

```
cttttagaga aagatattcc ttttgatctt gttcatgttg atcttccttc tgctcaacat    120
aaactctctt ccttctcaaa cagcccttg ggttagttcc agctatagaa gatggggatt    180
```

```
cttttagaga aagatattcc ttttgatctt gttcatgttg atcttccttc tgctcaacat    120
aaactctctt ccttctcaaa cagcccttg ggttagttcc agctatagaa gatggggatt    180
tcaggctttt tgaatcaaga gccataatga gatactatgc aacaaaatat gaagaaagag    240
ggcccaattt gttaggaaaa acattagaag agaaagcaat agttgatcaa tgggttgaag    300
tggaagccca taatttcaat aatttggttt acaatattgt aattgaagtt ttgataaagc    360
caaaaatggg ggaacaaggt gacatcaaca tagtcaaaag ctgtgaacat aagctggata    420
aagtgttcga tgtgtacgag gaaaggctat ccagttccaa atatcttgga ggagattatt    480
tcacacttgc tgatttaacc catatgcctt ccattaggta ccttgttcat gagcttgggt    540
tagcccattt ggttcacaat agaaacaagg tcaatgcttg gtggattgat atatcggacc    600
gaccggcttg gaaaaatttg atgattcttg ctggttatta g                        641

<210> SEQ ID NO 22
<211> LENGTH: 641
<212> TYPE: DNA
<213> ORGANISM: Euphorbia pulcherrima var. Titan white

<400> SEQUENCE: 22
atggtagtga aagtgtatgg agcagctcag gcagcttgcc cacaaagagt aatggcctgc    60
cttttagaga aagatattcc ttttgatctt gttcatgttg atcttccttc tgctcaacat    120
aaactctctt ccttctcaaa cagcccttg ggttagttcc agctatagaa gatggggatt    180
tcaggctttt tgaatcaaga gccataatga gatactatgc aacaaaatat gaagaaagag    240
ggcccaattt gttaggaaaa acattagaag agaaagcaat agttgatcaa tgggttgaag    300
tggaagccca taatttcaat aatttggttt acaatattgt aattgaagtt ttgataaagc    360
caaaaatggg ggaacaaggt gacatcaaca tagtcaaaag ctgtgaacat aagctggata    420
aagtgttcga tgtgtacgag gaaaggctat ccagttccaa atatcttgga ggagattatt    480
tcacacttgc tgatttaacc catatgcctt ccattaggta ccttgttcat gagcttgggt    540
tagcccattt ggttcacaat agaaacaagg tcaatgcttg gtggattgat atatcggacc    600
gaccggcttg gaaaaatttg atgattcttg ctggttatta g                        641

<210> SEQ ID NO 23
<211> LENGTH: 641
<212> TYPE: DNA
<213> ORGANISM: Euphorbia pulcherrima var. Bravo White

<400> SEQUENCE: 23
atggtagtga aagtgtatgg agcagctcag gcagcttgcc cacaaagagt aatggcctgc    60
cttttagaga aagatattcc ttttgatctt gttcatgttg atcttccttc tgctcaacat    120
aaactctctt ccttctcaaa cagcccttg ggttagttcc agctatagaa gatggggatt    180
tcaggctttt tgaatcaaga gccataatga gatactatgc aacaaaatat gaagaaagag    240
ggcccaattt gttaggaaaa acattagaag agaaagcaat agttgatcaa tgggttgaag    300
tggaagccca taatttcaat aatttggttt acaatattgt aattgaagtt ttgataaagc    360
caaaaatggg ggaacaaggt gacatcaaca tagtcaaaag ctgtgaacat aagctggata    420
aagtgttcga tgtgtacgag gaaaggctat ccagttccaa atatcttgga ggagattatt    480
tcacacttgc tgatttaacc catatgcctt ccattaggta ccttgttcat gagcttgggt    540
tagcccattt ggttcacaat agaaacaagg tcaatgcttg gtggattgat atatcggacc    600
gaccggcttg gaaaaatttg atgattcttg ctggttatta g                        641
```

<210> SEQ ID NO 24
<211> LENGTH: 641
<212> TYPE: DNA
<213> ORGANISM: Euphorbia pulcherrima var. SK130 White

<400> SEQUENCE: 24

```
atggtagtga aagtgtatgg agcagctcag gcagcttgcc cacaaagagt aatggcctgc    60
cttttagaga aagatattcc ttttgatctt gttcatgttg atcttccttc tgctcaacat   120
aaactctctt ccttctcaaa cagcccttttg ggttagttcc agctatagaa gatggggatt   180
tcaggctttt tgaatcaaga gccataatga gatactatgc aacaaaatat gaagaaagag   240
ggcccaattt gttaggaaaa acattagaag agaaagcaat agttgatcaa tgggttgaag   300
tggaagccca taatttcaat aatttggttt acaatattgt aattgaagtt ttgataaagc   360
caaaaatggg ggaacaaggt gacatcaaca tagtcaaaag ctgtgaacat aagctggata   420
aagtgttcga tgtgtacgag gaaaggctat ccagttccaa atatcttgga ggagattatt   480
tcacacttgc tgatttaacc catatgcctt ccattaggta ccttgttcat gagcttgggt   540
tagcccattt ggttcacaat agaaacaagg tcaatgcttg gtggattgat atatcggacc   600
gaccggcttg gaaaaatttg atgattcttg ctggttatta g                        641
```

<210> SEQ ID NO 25
<211> LENGTH: 641
<212> TYPE: DNA
<213> ORGANISM: Euphorbia pulcherrima x Euphorbia cornastra var. Pearl

<400> SEQUENCE: 25

```
atggtagtga aagtgtatgg agcagctcag gcagcttgcc cacaaagagt aatggcctgc    60
cttttagaga aagatattcc ttttgatctt gttcatgttg atcttccttc tgctcaacat   120
aaactctctt ccttctcaaa cagcccttttg ggttagttcc agctatagaa gatggggatt   180
tcaggctttt tgaatcaaga gccataatga gatactatgc aacaaaatat gaagaaagag   240
ggcccaattt gttaggaaaa acattagaag agaaagcaat agttgatcaa tgggttgaag   300
tggaagccca taatttcaat aatttggttt acaatattgt aattgaagtt ttgataaagc   360
caaaaatggg ggaacaaggt gacatcaaca tagtcaaaag ctgtgaacat aagctggata   420
aagtgttcga tgtgtacgag gaaaggctat ccagttccaa atatcttgga ggagattatt   480
tcacacttgc tgatttaacc catatgcctt ccattaggta ccttgttcat gagcttgggt   540
tagcccattt ggttcacaat agaaacaagg tcaatgcttg gtggattgat atatcggacc   600
gaccggcttg gaaaaatttg atgattcttg ctggttatta g                        641
```

<210> SEQ ID NO 26
<211> LENGTH: 641
<212> TYPE: DNA
<213> ORGANISM: Euphorbia pulcherrima x Euphorbia cornastra var. Pure White

<400> SEQUENCE: 26

```
atggtagtga aagtgtatgg agcagctcag gcagcttgcc cacaaagagt aatggcctgc    60
cttttagaga aagatattcc ttttgatctt gttcatgttg atcttccttc tgctcaacat   120
aaactctctt ccttctcaaa cagcccttttg ggttagttcc agctatagaa gatggggatt   180
tcaggctttt tgaatcaaga gccataatga gatactatgc aacaaaatat gaagaaagag   240
ggcccaattt gttaggaaaa acattagaag agaaagcaat agttgatcaa tgggttgaag   300
```

```
tggaagccca taatttcaat aatttggttt acaatattgt aattgaagtt ttgataaagc    360
caaaaatggg ggaacaaggt gacatcaaca tagtcaaaag ctgtgaacat aagctggata    420
aagtgttcga tgtgtacgag gaaaggctat ccagttccaa atatcttgga ggagattatt    480
tcacacttgc tgatttaacc catatgcctt ccattaggta ccttgttcat gagcttgggt    540
tagcccattt ggttcacaat agaaacaagg tcaatgcttg gtggattgat atatcggacc    600
gaccggcttg gaaaaatttg atgattcttg ctggttatta g                        641
```

<210> SEQ ID NO 27
<211> LENGTH: 641
<212> TYPE: DNA
<213> ORGANISM: Euphorbia pulcherrima var. Alaska

<400> SEQUENCE: 27

```
atggtagtga aagtgtatgg agcagctcag gcagcttgcc cacaaagagt aatggcctgc     60
cttttagaga aagatattcc ttttgatctt gttcatgttg atcttccttc tgctcaacat    120
aaactctctt ccttctcaaa cagcccttty ggttagttcc agctatagaa gatggggatt    180
tcaggctttt tgaatcaaga gccataatga gatactatgc aacaaaatat gaagaaagag    240
ggcccaattt gttaggaaaa acattagaag agaaagcaat agttgatcaa tgggttgaag    300
tggaagccca taatttcaat aatttggttt acaatattgt aattgaagtt ttgataaagc    360
caaaaatggg ggaacaaggt gacatcaaca tagtcaaaag ctgtgaacat aagctggata    420
aagtgttcga tgtgtacgag gaaaggctat ccagttccaa atatcttgga ggagattatt    480
tcacacttgc tgatttaacc catatgcctt ccattaggta ccttgttcat gagcttgggt    540
tagcccattt ggttcacaat agaaacaagg tcaatgcttg gtggattgat atatcggacc    600
gaccggcttg gaaaaatttg atgattcttg ctggttatta g                        641
```

<210> SEQ ID NO 28
<211> LENGTH: 641
<212> TYPE: DNA
<213> ORGANISM: Euphorbia pulcherrima var. Alpina

<400> SEQUENCE: 28

```
atggtagtga aagtgtatgg agcagctcag gcagcttgcc cacaaagagt aatggcctgc     60
cttttagaga aagatattcc ttttgatctt gttcatgttg atcttccttc tgctcaacat    120
aaactctctt ccttctcaaa cagcccttty ggttagttcc agctatagaa gatggggatt    180
tcaggctttt tgaatcaaga gccataatga gatactatgc aacaaaatat gaagaaagag    240
ggcccaattt gttaggaaaa acattagaag agaaagcaat agttgatcaa tgggttgaag    300
tggaagccca taatttcaat aatttggttt acaatattgt aattgaagtt ttgataaagc    360
caaaaatggg ggaacaaggt gacatcaaca tagtcaaaag ctgtgaacat aagctggata    420
aagtgttcga tgtgtacgag gaaaggctat ccagttccaa atatcttgga ggagattatt    480
tcacacttgc tgatttaacc catatgcctt ccattaggta ccttgttcat gagcttgggt    540
tagcccattt ggttcacaat agaaacaagg tcaatgcttg gtggattgat atatcggacc    600
gaccggcttg gaaaaatttg atgattcttg ctggttatta g                        641
```

<210> SEQ ID NO 29
<211> LENGTH: 585
<212> TYPE: DNA
<213> ORGANISM: Euphorbia pulcherrima SK158 White

<400> SEQUENCE: 29

```
cagctcaggc agcttgccca caaagagtaa tggcctgcct tttagagaaa gatattcctt      60
ttgatcttgt tcatgttgat cttccttctg ctcaacataa actctcttcc ttctcaaaca     120
gcccttgggt tagttccag ctatagaaga tggggatttc aggcttttg aatcaagagc      180
cataatgaga tactatgcaa caaatatga agaaagaggg cccaatttgt taggaaaaac     240
attagaagag aaagcaatag ttgatcaatg ggttgaagtg gaagcccata atttcaataa     300
tttggtttac aatattgtaa ttgaagtttt gataaagcca aaaatggggg aacaaggtga     360
catcaacata gtcaaaagct gtgaacataa gctggataaa gtgttcgatg tgtacgagga     420
aaggctatcc agttccaaat atcttggagg agattatttc acacttgctg atttaaccca     480
tatgccttcc attaggtacc ttgttcatga gcttgggtta gcccatttgg ttcacaatag     540
aaacaaggtc aatgcttggt ggattgatat atcggaccga ccggc                    585
```

<210> SEQ ID NO 30
<211> LENGTH: 641
<212> TYPE: DNA
<213> ORGANISM: Euphorbia pulcherrima Beauty White

<400> SEQUENCE: 30

```
atggtagtga agtgtatgg agcagctcag gcagcttgcc cacaaagagt aatggcctgc      60
cttttagaga aagatattcc ttttgatctt gttcatgttg atcttccttc tgctcaacat     120
aaactctctt ccttctcaaa cagccctttg ggttagttcc agctatagaa gatggggatt     180
tcaggctttt tgaatcaaga gccataatga gatactatgc aacaaatat gaagaaagag     240
ggcccaattt gttaggaaaa acattagaag agaaagcaat agttgatcaa tgggttgaag     300
tggaagccca taattcaat aatttggttt acaatattgt aattgaagtt ttgataaagc     360
caaaaatggg ggaacaaggt gacatcaaca tagtcaaaag ctgtgaacat aagctggata     420
aagtgttcga tgtgtacgag gaaaggctat ccagttccaa atatcttgga ggagattatt     480
tcacacttgc tgatttaacc catatgcctt ccattaggta ccttgttcat gagcttgggt     540
tagcccattt ggttcacaat agaaacaagg tcaatgcttg gtggattgat atatcggacc     600
gaccggcttg aaaaatttg atgattcttg ctggttatta g                         641
```

<210> SEQ ID NO 31
<211> LENGTH: 591
<212> TYPE: DNA
<213> ORGANISM: Euphorbia pulcherrima x Euphorbia cornastra var. Dark
      Pink

<400> SEQUENCE: 31

```
ggagcagctc aggcagcttg cccacaaaga gtaatggcct gccttttaga gaaagatatt      60
ccttttgatc ttgttcatgt tgatcttcct tctgctcaac ataaactctc ttccttctca     120
aacagccctt tgggttagtt ccagctatag aagatgggga tttcaggctt tttgaatcaa     180
gagccataat gagatactat gcaacaaaat atgaagaaag agggcccaat tgttaggaa      240
aaacattaga agagaaagca atagttgatc aatgggttga agtggaagcc cataatttca     300
ataatttggt ttacaatatt gtaattgaag ttttgataaa gccaaaaatg ggaacaag      360
gtgacatcaa catagtcaaa agctgtgaac ataagctgga taaagtgttc gatgtgtacg     420
aggaaaggct atccagttcc aaatatcttg gaggagatta tttcacactt gctgatttaa     480
cccatatgcc ttccattagg taccttgttc atgagcttgg gttagcccat tggttcaca      540
```
atagaaacaa ggtcaatgct tggtggattg atatatcgga ccgaccggct g    591

<210> SEQ ID NO 32
<211> LENGTH: 641
<212> TYPE: DNA
<213> ORGANISM: Euphorbia pulcherrima x Euphorbia cornastra var. Hot
      Pink

<400> SEQUENCE: 32
atggtagtga aagtgtatgg agcagctcag gcagcttgcc cacaaagagt aatggcctgc    60
cttttagaga aagatattcc ttttgatctt gttcatgttg atcttccttc tgctcaacat    120
aaactctctt ccttctcaaa cagccctttg ggttagttcc agctatagaa gatggggatt    180
tcaggctttt tgaatcaaga gccataatga gatactatgc aacaaaatat gaagaaagag    240
ggcccaattt gttaggaaaa acattagaag agaaagcaat agttgatcaa tgggttgaag    300
tggaagccca taatttcaat aatttggttt acaatattgt aattgaagtt ttgataaagc    360
caaaaatggg ggaacaaggt gacatcaaca tagtcaaaag ctgtgaacat aagctggata    420
aagtgttcga tgtgtacgag gaaaggctat ccagttccaa atatcttgga ggagattatt    480
tcacacttgc tgatttaacc catatgcctt ccattaggta ccttgttcat gagcttgggt    540
tagcccattt ggttcacaat agaaacaagg tcaatgcttg gtggattgat atatcggacc    600
gaccggcttg gaaaaatttg atgattcttg ctggttatta g    641

<210> SEQ ID NO 33
<211> LENGTH: 641
<212> TYPE: DNA
<213> ORGANISM: Euphorbia pulcherrima x Euphorbia cornastra var. Pink

<400> SEQUENCE: 33
atggtagtga aagtgtatgg agcagctcag gcagcttgcc cacaaagagt aatggcctgc    60
cttttagaga aagatattcc ttttgatctt gttcatgttg atcttccttc tgctcaacat    120
aaactctctt ccttctcaaa cagccctttg ggttagttcc agctatagaa gatggggatt    180
tcaggctttt tgaatcaaga gccataatga gatactatgc aacaaaatat gaagaaagag    240
ggcccaattt gttaggaaaa acattagaag agaaagcaat agttgatcaa tgggttgaag    300
tggaagccca taatttcaat aatttggttt acaatattgt aattgaagtt ttgataaagc    360
caaaaatggg ggaacaaggt gacatcaaca tagtcaaaag ctgtgaacat aagctggata    420
aagtgttcga tgtgtacgag gaaaggctat ccagttccaa atatcttgga ggagattatt    480
tcacacttgc tgatttaacc catatgcctt ccattaggta ccttgttcat gagcttgggt    540
tagcccattt ggttcacaat agaaacaagg tcaatgcttg gtggattgat atatcggacc    600
gaccggcttg gaaaaatttg atgattcttg ctggttatta g    641

<210> SEQ ID NO 34
<211> LENGTH: 641
<212> TYPE: DNA
<213> ORGANISM: Euphorbia pulcherrima x Euphorbia cornastra var. Soft
      Pink

<400> SEQUENCE: 34
atggtagtga aagtgtatgg agcagctcag gcagcttgcc cacaaagagt aatggcctgc    60
cttttagaga aagatattcc ttttgatctt gttcatgttg atcttccttc tgctcaacat    120
aaactctctt ccttctcaaa cagccctttg ggttagttcc agctatagaa gatggggatt    180
tcaggctttt tgaatcaaga gccataatga gatactatgc aacaaaatat gaagaaagag    240

```
ggcccaattt gttaggaaaa acattagaag agaaagcaat agttgatcaa tgggttgaag      300
tggaagccca taatttcaat aatttggttt acaatattgt aattgaagtt ttgataaagc      360
caaaaatggg ggaacaaggt gacatcaaca tagtcaaaag ctgtgaacat aagctggata      420
aagtgttcga tgtgtacgag gaaaggctat ccagttccaa atatcttgga ggagattatt      480
tcacacttgc tgatttaacc catatgcctt ccattaggta ccttgttcat gagcttgggt      540
tagcccattt ggttcacaat agaaacaagg tcaatgcttg gtggattgat atatcggacc      600
gaccggcttg gaaaaatttg atgattcttg ctggttatta g                         641
```

<210> SEQ ID NO 35
<211> LENGTH: 641
<212> TYPE: DNA
<213> ORGANISM: Euphorbia pulcherrima var. Premium Red

<400> SEQUENCE: 35

```
atggtagtga aagtgtatgg agcagctcag gcagcttgcc cacaaagagt aatggcctgc       60
cttttagaga aagatattcc ttttgatctt gttcatgttg atcttccttc tgctcaacat      120
aaactctctt ccttctcaaa cagcccttg ggttagttcc agctatagaa gatggggatt       180
tcaggctttt tgaatcaaga gccataatga gatactatgc aacaaaatat gaagaaagag      240
ggcccaattt gttaggaaaa acattagaag agaaagcaat agttgatcaa tgggttgaag      300
tggaagccca taatttcaat aatttggttt acaatattgt aattgaagtt ttgataaagc      360
caaaaatggg ggaacaaggt gacatcaaca tagtcaaaag ctgtgaacat aagctggata      420
aagtgttcga tgtgtacgag gaaaggctat ccagttccaa atatcttgga ggagattatt      480
tcacacttgc tgatttaacc catatgcctt ccattaggta ccttgttcat gagcttgggt      540
tagcccattt ggttcacaat agaaacaagg tcaatgcttg gtggattgat atatcggacc      600
gaccggcttg gaaaaatttg atgattcttg ctggttatta g                         641
```

<210> SEQ ID NO 36
<211> LENGTH: 641
<212> TYPE: DNA
<213> ORGANISM: Euphorbia pulcherrima var. Freedom Red

<400> SEQUENCE: 36

```
atggtagtga aagtgtatgg agcagctcag gcagcttgcc cacaaagagt aatggcctgc       60
cttttagaga aagatattcc ttttgatctt gttcatgttg atcttccttc tgctcaacat      120
aaactctctt ccttctcaaa cagcccttg ggttagttcc agctatagaa gatggggatt       180
tcaggctttt tgaatcaaga gccataatga gatactatgc aacaaaatat gaagaaagag      240
ggcccaattt gttaggaaaa acattagaag agaaagcaat agttgatcaa tgggttgaag      300
tggaagccca taatttcaat aatttggttt acaatattgt aattgaagtt ttgataaagc      360
caaaaatggg ggaacaaggt gacatcaaca tagtcaaaag ctgtgaacat aagctggata      420
aagtgttcga tgtgtacgag gaaaggctat ccagttccaa atatcttgga ggagattatt      480
tcacacttgc tgatttaacc catatgcctt ccattaggta ccttgttcat gagcttgggt      540
tagcccattt ggttcacaat agaaacaagg tcaatgcttg gtggattgat atatcggacc      600
gaccggcttg gaaaaatttg atgattcttg ctggttatta g                         641
```

<210> SEQ ID NO 37
<211> LENGTH: 641
<212> TYPE: DNA

<213> ORGANISM: Euphorbia pulcherrima var. Otto Red

<400> SEQUENCE: 37

```
atggtagtga aagtgtatgg agcagctcag gcagcttgcc cacaaagagt aatggcctgc      60
cttttagaga aagatattcc ttttgatctt gttcatgttg atcttccttc tgctcaacat     120
aaactctctt ccttctcaaa cagccctttg ggttagttcc agctatagaa gatggggatt     180
tcaggctttt tgaatcaaga gccataatga gatactatgc aacaaaatat gaagaaagag     240
ggcccaattt gttaggaaaa acattagaag agaaagcaat agttgatcaa tgggttgaag     300
tggaagccca taatttcaat aatttggttt acaatattgt aattgaagtt ttgataaagc     360
caaaaatggg ggaacaaggt gacatcaaca tagtcaaaag ctgtgaacat aagctggata     420
aagtgttcga tgtgtacgag gaaaggctat ccagttccaa atatcttgga ggagattatt     480
tcacacttgc tgatttaacc catatgcctt ccattaggta ccttgttcat gagcttgggt     540
tagcccattt ggttcacaat agaaacaagg tcaatgcttg gtggattgat atatcggacc     600
gaccggcttg gaaaaatttg atgattcttg ctggttatta g                         641
```

<210> SEQ ID NO 38
<211> LENGTH: 641
<212> TYPE: DNA
<213> ORGANISM: Euphorbia pulcherrima var. Season Red

<400> SEQUENCE: 38

```
atggtagtga aagtgtatgg agcagctcag gcagcttgcc cacaaagagt aatggcctgc      60
cttttagaga aagatattcc ttttgatctt gttcatgttg atcttccttc tgctcaacat     120
aaactctctt ccttctcaaa cagccctttg ggttagttcc agctatagaa gatggggatt     180
tcaggctttt tgaatcaaga gccataatga gatactatgc aacaaaatat gaagaaagag     240
ggcccaattt gttaggaaaa acattagaag agaaagcaat agttgatcaa tgggttgaag     300
tggaagccca taatttcaat aatttggttt acaatattgt aattgaagtt ttgataaagc     360
caaaaatggg ggaacaaggt gacatcaaca tagtcaaaag ctgtgaacat aagctggata     420
aagtgttcga tgtgtacgag gaaaggctat ccagttccaa atatcttgga ggagattatt     480
tcacacttgc tgatttaacc catatgcctt ccattaggta ccttgttcat gagcttgggt     540
tagcccattt ggttcacaat agaaacaagg tcaatgcttg gtggattgat atatcggacc     600
gaccggcttg gaaaaatttg atgattcttg ctggttatta g                         641
```

<210> SEQ ID NO 39
<211> LENGTH: 641
<212> TYPE: DNA
<213> ORGANISM: Euphorbia pulcherrima var. Beauty Red

<400> SEQUENCE: 39

```
atggtagtga aagtgtatgg agcagctcag gcagcttgcc cacaaagagt aatggcctgc      60
cttttagaga aagatattcc ttttgatctt gttcatgttg atcttccttc tgctcaacat     120
aaactctctt ccttctcaaa cagccctttg ggttagttcc agctatagaa gatggggatt     180
tcaggctttt tgaatcaaga gccataatga gatactatgc aacaaaatat gaagaaagag     240
ggcccaattt gttaggaaaa acattagaag agaaagcaat agttgatcaa tgggttgaag     300
tggaagccca taatttcaat aatttggttt acaatattgt aattgaagtt ttgataaagc     360
caaaaatggg ggaacaaggt gacatcaaca tagtcaaaag ctgtgaacat aagctggata     420
aagtgttcga tgtgtacgag gaaaggctat ccagttccaa atatcttgga ggagattatt     480
```

```
tcacacttgc tgatttaacc catatgcctt ccattaggta ccttgttcat gagcttgggt      540
tagcccattt ggttcacaat agaaacaagg tcaatgcttg gtggattgat atatcggacc      600
gaccggcttg gaaaaatttg atgattcttg ctggttatta g                         641
```

<210> SEQ ID NO 40
<211> LENGTH: 641
<212> TYPE: DNA
<213> ORGANISM: Euphorbia pulcherirma var. SK158 Red

<400> SEQUENCE: 40

```
atggtagtga aagtgtatgg agcagctcag gcagcttgcc cacaaagagt aatggcctgc       60
cttttagaga aagatattcc ttttgatctt gttcatgttg atcttccttc tgctcaacat      120
aaactctctt ccttctcaaa cagcccttgg ggttagttcc agctatagaa gatggggatt      180
tcaggctttt tgaatcaaga gccataatga gatactatgc aacaaaatat gaagaaagag      240
ggcccaattt gttaggaaaa acattagaag agaaagcaat agttgatcaa tgggttgaag      300
tggaagccca taatttcaat aatttggttt acaatattgt aattgaagtt ttgataaagc      360
caaaaatggg ggaacaaggt gacatcaaca tagtcaaaag ctgtgaacat aagctggata      420
aagtgttcga tgtgtacgag gaaaggctat ccagttccaa atatcttgga ggagattatt      480
tcacacttgc tgatttaacc catatgcctt ccattaggta ccttgttcat gagcttgggt      540
tagcccattt ggttcacaat agaaacaagg tcaatgcttg gtggattgat atatcggacc      600
gaccggcttg gaaaaatttg atgattcttg ctggttatta g                         641
```

<210> SEQ ID NO 41
<211> LENGTH: 641
<212> TYPE: DNA
<213> ORGANISM: Euphorbia pulcherrima

<400> SEQUENCE: 41

```
atggtagtga aagtgtatgg agcagctcag gcagcttgcc cacaaagagt aatggcctgc       60
cttttagaga aagatattcc ttttgatctt gttcatgttg atcttccttc tgctcaacat      120
aaactctctt ccttctcaaa cagcccttgg ggttagttcc agctatagaa gatggggatt      180
tcaggctttt tgaatcaaga gccataatga gatactatgc aacaaaatat gaagaaagag      240
ggcccaattt gttaggaaaa acattagaag agaaagcaat agttgatcaa tgggttgaag      300
tggaagccca taatttcaat aatttggttt acaatattgt aattgaagtt ttgataaagc      360
caaaaatggg ggaacaaggt gacatcaaca tagtcaaaag ctgtgaacat aagctggata      420
aagtgttcga tgtgtacgag gaaaggctat ccagttccaa atatcttgga ggagattatt      480
tcacacttgc tgatttaacc catatgcctt ccattaggta ccttgttcat gagcttgggt      540
tagcccattt ggttcacaat agaaacaagg tcaatgcttg gtggattgat atatcggacc      600
gaccggcttg gaaaaatttg atgattcttg ctggttatta g                         641
```

<210> SEQ ID NO 42
<211> LENGTH: 645
<212> TYPE: DNA
<213> ORGANISM: Arabidopsis thaliana

<400> SEQUENCE: 42

```
atggtggtca aagtatatgg gcagataaaa gcagctaatc cacaaagagt attgctctgc       60
tttttggaaa aagacatcga gtttgaagta attcatgtcg atctcgataa acttgaacag      120
```

| | |
|---|---|
| aaaaaaccac aacatcttct tcgtcagccg tttggtcaag ttccagctat tgaagatgga | 180 |
| tatctgaagc tttttgaatc gcgagccata gcgaggtact acgcgacaaa gtatgcggac | 240 |
| caaggaacgg acctattggg caagactttg gagggacgag ccattgtgga ccagtgggtg | 300 |
| gaagttgaga ataactattt ctacgctgtg gctctaccct tagttatgaa cgtcgtcttt | 360 |
| aagcccaagt ctggtaagcc atgcgacgtc gctttggttg aggagctaaa ggtcaagttc | 420 |
| gacaaggtcc tggatgtgta tgagaaccgg ttagctacga accggtactt gggcggtgat | 480 |
| gaattcacat tagctgattt gagtcatatg cccggtatga gatatatcat gaatgaaacc | 540 |
| agtttgagtg gtttggttac gtctcgagag aatctcaacc ggtggtggaa tgagatttcg | 600 |
| gctagaccgg cttggaagaa gctcatggaa ttggctgcct attaa | 645 |

<210> SEQ ID NO 43
<211> LENGTH: 645
<212> TYPE: DNA
<213> ORGANISM: Arabidopsis thaliana

<400> SEQUENCE: 43

| | |
|---|---|
| atggttgtga aactatatgg acaggtaaca gcagcttgtc cacaaagagt cttgctttgt | 60 |
| tttctcgaga aggaattga atttgagatt attcatatcg atcttgatac atttgagcaa | 120 |
| aaaaaaccag aacatcttct tcgtcagcca tttggtcaag ttccagccat agaagatgga | 180 |
| gatttcaagc tttttgaatc acgagccatc gcgagatact acgctaccaa gttcgcggac | 240 |
| caaggcacga accttttggg caagtctcta gagcaccgag ccatcgtgga ccagtgggct | 300 |
| gacgtggaga cctattactt caacgttctg gcccaacccc tcgtgattaa cctaatcatc | 360 |
| aagcctaggt taggcgagaa atgtgacgtc gttttggtcg aggatctcaa agtgaagcta | 420 |
| ggagtggtct tggacatata caataaccgg cttttcttcga accggttttt ggctggtgaa | 480 |
| gaattcacta tggctgattt gacgcacatg ccggcgatgg ggtacttgat gagtataacc | 540 |
| gatataaacc agatggttaa ggctcggggt agttttaacc ggtggtggga agagatttcg | 600 |
| gatagaccgt cttggaagaa gcttatggtg ctggctggtc actga | 645 |

<210> SEQ ID NO 44
<211> LENGTH: 699
<212> TYPE: DNA
<213> ORGANISM: Petunia x hybrida

<400> SEQUENCE: 44

| | |
|---|---|
| atggttgtga aagtgcatgg ttcagcaatg gctgcatgcc acagagggt catggtctgc | 60 |
| ctgatagagt tgggggttga ttttgagctt atccatgttg atcttgattc tctcgagcag | 120 |
| aaaaaacctg agtttctagt tttacagcca tttggacaag ttcctgtcat tgaagatggt | 180 |
| gatttaggc tttttgaatc cagagcaata attaggtact atgcagcaaa gtatgaagtc | 240 |
| aagggaagca aactaacagg aacaacattg gaagagaaag ctctagttga tcaatggcta | 300 |
| gaagttgaat ccaataacta caatgactta gtatacaaca tggtcctcca actcctagta | 360 |
| ttccccaaaa tgggacaaac cagtgactta acattggtaa caaaatgtgc caacaagtta | 420 |
| gagaatgtct ttgacatttta tgaacaaagg ttgtcaaaga gtaaatatct agcaggagag | 480 |
| tttttctcac tagctgatct aagtcacctt cctagtttaa ggttcttaat gaatgaaggt | 540 |
| ggtttttcac atttggtgac caagagaaag tgtttgcatg agtggtattt ggatatttca | 600 |
| agtagggatt cttggaagaa agtgttggac ctcatgatga agaagatatc agagattgaa | 660 |
| gcagtgtcta tcccagctaa agaagaagca aaagtttga | 699 |

<210> SEQ ID NO 45
<211> LENGTH: 642
<212> TYPE: DNA
<213> ORGANISM: Cyclamen persicum x Cyclamen purpurascens

<400> SEQUENCE: 45

| | | | | | |
|---|---|---|---|---|---|
| atggttgtta | aagtgtatgg | tccagccact | gcaggttgcc | cacagagggt | gatcgcttgc | 60 |
| cttttgaac | ttgacgtcga | ctttgaaatc | attcacgtcg | accttgaatc | cggggagcat | 120 |
| aagaagcccg | attttcttct | cgccagccc | tttggacaag | tcccagccat | agaggatgga | 180 |
| gatttcaggc | ttttcgagtc | ccgggcaatc | atgagatact | atgcagcaaa | gtattccgag | 240 |
| aagaatcctg | acctacaggg | atcgactcta | gaggagaaag | ctctagttga | ccagtggctc | 300 |
| gaggtcgaat | cacacaactt | caatgacctg | gtatacactc | tagtactcca | cctcatggtt | 360 |
| ttccctcaga | tgggcaagcg | cagtgacatg | cagttggtac | aagaatgcga | gagcaaactt | 420 |
| gagaaagtat | ttgatatata | cgaggagaga | ttgtcgaaga | gtaactacct | ggccggaaaa | 480 |
| ttgttcaccc | ttgccgacct | cagccacctc | ccatctatca | cttttctaat | gggcgagggt | 540 |
| gggttgggac | atatggtgag | gaacagaaag | aacgtcaact | cgtggtggat | ggatatttcg | 600 |
| agcaggcctt | cttggaagaa | ggtgcggaag | ctgatggact | ag | | 642 |

<210> SEQ ID NO 46
<211> LENGTH: 642
<212> TYPE: DNA
<213> ORGANISM: Vitis vinifera

<400> SEQUENCE: 46

| | | | | | |
|---|---|---|---|---|---|
| atggtgatga | aggtgtatgg | cccagtgagg | gctgcatgcc | cacagagggt | gttggcttgc | 60 |
| cttgtagaga | agggcgtgga | gtttgaggtt | gtccatgtcg | acctcgactc | tggcgagcaa | 120 |
| aaacggcctg | atttcctcct | tcgacagcct | tttgggcaag | ttccagtggt | agaagatggc | 180 |
| gatttcaggc | tgtttgagtc | gagggcgatt | gtgaggtaca | tcgcggccaa | gtacgcggag | 240 |
| caagggcctg | acctcttggg | aaaaagcttg | gaggagaaag | cggtagttga | tcaatggctg | 300 |
| gaagtggaag | ctcacaactt | caacgagttg | gtgtacacac | tggtcatgca | gctagtgatc | 360 |
| ctacctcgaa | tgggtgagcg | ggggacttg | gctttagccc | acacttgtga | gcagaagctg | 420 |
| gaaaaggtgt | ttgatgtgta | tgagcagagg | ctgtcgaaga | gccggtacct | tgcaggagat | 480 |
| tcattcactc | tcgctgatct | gagtcatctt | ccggccatca | gatacttggt | gaaggaagct | 540 |
| ggaatggcgc | acttggttac | tgagaggaag | agtgtgagtg | catggtggga | ggacatttcc | 600 |
| aacagggctg | cttggaaaaa | agtcatggag | ctcgctgctt | ga | | 642 |

<210> SEQ ID NO 47
<211> LENGTH: 645
<212> TYPE: DNA
<213> ORGANISM: Litchi chinensis

<400> SEQUENCE: 47

| | | | | | |
|---|---|---|---|---|---|
| atggtggtta | aagtttatgg | accagttacg | gcaggttgcc | cacagagagt | tatgacttgc | 60 |
| cttcttgaaa | aagatgttga | attcgaaatc | attcatgtta | atatcgacaa | tggagagcat | 120 |
| aagcgtcctg | agtttcttct | tcgacagcct | tttgggcaag | ttccagtaat | tgaagatgac | 180 |
| gattttaagc | ttttttgaatc | aagggcaata | ctgcggtact | acgcggccaa | gtatgcggac | 240 |
| cgtggaccca | acctgcttgg | aaccaccctg | gaggagaggg | ccagggtgga | ccagtggctg | 300 |

```
gaagtggaag cacacaactt caatgacttg atctacacta tggtgcttca actgatagtt    360
attccaagca tggggcagcc tggggacctg acgttggtcc actcctgcga gcagaagcta    420
gaggcagttt ttgacgtcta cgaaaagcag ctttcgaaga gtaagtacct cgccggagat    480
tggttctctt tggcagacct cagccacatg cctgccctcc ggttcttgat ggaggatgct    540
aagttggtgc acctggtgaa ggagaggaag catgttaatg cgtggtggga ggagatttcc    600
ggccgcctct cgtggaagaa attgatgaag cttgcctact attag                    645
```

<210> SEQ ID NO 48
<211> LENGTH: 648
<212> TYPE: DNA
<213> ORGANISM: Prunus persica

<400> SEQUENCE: 48

```
atggttgtga aagtgtatgg tccagtcaag gcagcctgcc ctcagagggt tatggtttgt    60
cttttggaga aggagtgaa tttcgaaatt gttgatgtta atcttgaggt gggagagcaa    120
aagcaacctc agttcctctc ccgtcagccg tttggtcaag ttccagcagt agaagatggt    180
gatttcaggc tatttgagtc tagggctatt atcagatact acgcagccaa gtacgccgac    240
cgtggtccca acctattggg aacaaccctg gaggagaagg ctctggtgga tcagtggctg    300
gaagtagaag ctcacaattt caatgacttg gtttacactc tggtacttca acttctggtg    360
ctgcctcgca tggggagcg tggtgacgtg gccttggtcc atgcatgtga ggagaaactg    420
gagaaggtgt cgatgtttta tgaggaaaga ttatcaaaga gcagctatct ggctggagaa    480
gctttcactc tggctgatct gagccatctt ccagggataa gctatctgat tgatgaagct    540 aaattgggc atttggtgtc tgagaggaag aatgtgaatg cttggtggaa agacatatcc    600
aacaggcctg cttggaagaa actaatgagc cttgctagtg actactag                648
```

<210> SEQ ID NO 49
<211> LENGTH: 651
<212> TYPE: DNA
<213> ORGANISM: Prunus persica

<400> SEQUENCE: 49

```
atggttgtga aagtgtatgg tccagtcaag gcagcctgcc ctcagagggt tatggtttgt    60
cttttggaga aggagtgaa tttcgaaatt gttgatgtta atcttgaggt gggagagcaa    120
aagcaacctc agttcctctc ccgtcagccg tttggtcaag ttccagcagt agaagatggt    180
gatttcaggc tatttgagtc tagggctatt atcagatact acgcagccaa gtacgccgac    240
cgtggtccca acctattggg aacaaccctg gaggagaagg ctctggtgga tcagtggctg    300
gaagtagaag ctcacaattt caatgacttg gtttacactc tggtacttca acttctggtg    360
ctgcctgatc gcatgggga gcgtggtgac gtggccttgg tccatgcatg tgaggagaaa    420
ctggagaagg tgttcgatgt ttatgaggaa agattatcaa agagcagcta tctggctgga    480
gaagctttca ctctggctga tctgagccat cttccaggga taagctatct gattgatgaa    540
gctaaattgg ggcatttggt gtctgagagg aagaatgtga atgcttggtg gaaagacata    600
tccaacaggc tgcttggaa gaaactaatg agccttgcta gtgactacta g               651
```

<210> SEQ ID NO 50
<211> LENGTH: 51
<212> TYPE: PRT
<213> ORGANISM: Euphorbia pulcherrima

<400> SEQUENCE: 50

```
Met Val Val Lys Val Tyr Gly Ala Ala Gln Ala Ala Cys Pro Gln Arg
1               5                   10                  15

Val Met Ala Cys Leu Leu Glu Lys Asp Ile Pro Phe Asp Leu Val His
            20                  25                  30

Val Asp Leu Pro Ser Ala Gln His Lys Leu Ser Ser Phe Ser Asn Ser
        35                  40                  45

Pro Leu Gly
    50
```

<210> SEQ ID NO 51
<211> LENGTH: 145
<212> TYPE: PRT
<213> ORGANISM: Euphorbia pulcherrima
<220> FEATURE:
<221> NAME/KEY: misc_feature
<222> LOCATION: (145)..(145)
<223> OTHER INFORMATION: Xaa can be any naturally occurring amino acid

<400> SEQUENCE: 51

```
Met Arg Tyr Tyr Ala Thr Lys Tyr Glu Glu Arg Gly Pro Asn Leu Leu
1               5                   10                  15

Gly Lys Thr Leu Glu Glu Lys Ala Ile Val Asp Gln Trp Val Glu Val
            20                  25                  30

Glu Ala His Asn Phe Asn Asn Leu Val Tyr Asn Ile Val Glu Val
        35                  40                  45

Leu Ile Lys Pro Lys Met Gly Glu Gln Gly Asp Ile Asn Ile Val Lys
    50                  55                  60

Ser Cys Glu His Lys Leu Asp Lys Val Phe Asp Val Tyr Glu Glu Arg
65                  70                  75                  80

Leu Ser Ser Ser Lys Tyr Leu Gly Gly Asp Tyr Phe Thr Leu Ala Asp
                85                  90                  95

Leu Thr His Met Pro Ser Ile Arg Tyr Leu Val His Glu Leu Gly Leu
            100                 105                 110

Ala His Leu Val His Asn Arg Asn Lys Val Asn Ala Trp Trp Ile Asp
        115                 120                 125

Ile Ser Asp Arg Pro Ala Trp Lys Asn Leu Met Ile Leu Ala Gly Tyr
    130                 135                 140

Xaa
145
```

<210> SEQ ID NO 52
<211> LENGTH: 214
<212> TYPE: PRT
<213> ORGANISM: Arabidopsis thaliana

<400> SEQUENCE: 52

```
Met Val Val Lys Val Tyr Gly Gln Ile Lys Ala Ala Asn Pro Gln Arg
1               5                   10                  15

Val Leu Leu Cys Phe Leu Glu Lys Asp Ile Glu Phe Glu Val Ile His
            20                  25                  30

Val Asp Leu Asp Lys Leu Glu Gln Lys Lys Pro Gln His Leu Leu Arg
        35                  40                  45

Gln Pro Phe Gly Gln Val Pro Ala Ile Glu Asp Gly Tyr Leu Lys Leu
    50                  55                  60

Phe Glu Ser Arg Ala Ile Ala Arg Tyr Tyr Ala Thr Lys Tyr Ala Asp
65                  70                  75                  80

Gln Gly Thr Asp Leu Leu Gly Lys Thr Leu Glu Gly Arg Ala Ile Val
```

```
                    85                  90                  95
Asp Gln Trp Val Glu Val Glu Asn Asn Tyr Phe Tyr Ala Val Ala Leu
                100                 105                 110

Pro Leu Val Met Asn Val Val Phe Lys Pro Lys Ser Gly Lys Pro Cys
            115                 120                 125

Asp Val Ala Leu Val Glu Glu Leu Lys Val Lys Phe Asp Lys Val Leu
        130                 135                 140

Asp Val Tyr Glu Asn Arg Leu Ala Thr Asn Arg Tyr Leu Gly Gly Asp
145                 150                 155                 160

Glu Phe Thr Leu Ala Asp Leu Ser His Met Pro Gly Met Arg Tyr Ile
                165                 170                 175

Met Asn Glu Thr Ser Leu Ser Gly Leu Val Thr Ser Arg Glu Asn Leu
            180                 185                 190

Asn Arg Trp Trp Asn Glu Ile Ser Ala Arg Pro Ala Trp Lys Lys Leu
        195                 200                 205

Met Glu Leu Ala Ala Tyr
    210

<210> SEQ ID NO 53
<211> LENGTH: 214
<212> TYPE: PRT
<213> ORGANISM: Arabidopsis thaliana

<400> SEQUENCE: 53

Met Val Val Lys Leu Tyr Gly Gln Val Thr Ala Ala Cys Pro Gln Arg
1               5                   10                  15

Val Leu Leu Cys Phe Leu Glu Lys Gly Ile Glu Phe Glu Ile Ile His
            20                  25                  30

Ile Asp Leu Asp Thr Phe Glu Gln Lys Pro Glu His Leu Leu Arg
        35                  40                  45

Gln Pro Phe Gly Gln Val Pro Ala Ile Glu Asp Gly Asp Phe Lys Leu
    50                  55                  60

Phe Glu Ser Arg Ala Ile Ala Arg Tyr Tyr Ala Thr Lys Phe Ala Asp
65                  70                  75                  80

Gln Gly Thr Asn Leu Leu Gly Lys Ser Leu Glu His Arg Ala Ile Val
                85                  90                  95

Asp Gln Trp Ala Asp Val Glu Thr Tyr Tyr Phe Asn Val Leu Ala Gln
                100                 105                 110

Pro Leu Val Ile Asn Leu Ile Ile Lys Pro Arg Leu Gly Glu Lys Cys
            115                 120                 125

Asp Val Val Leu Val Glu Asp Leu Lys Val Lys Leu Gly Val Val Leu
        130                 135                 140

Asp Ile Tyr Asn Asn Arg Leu Ser Ser Asn Arg Phe Leu Ala Gly Glu
145                 150                 155                 160

Glu Phe Thr Met Ala Asp Leu Thr His Met Pro Ala Met Gly Tyr Leu
                165                 170                 175

Met Ser Ile Thr Asp Ile Asn Gln Met Val Lys Ala Arg Gly Ser Phe
            180                 185                 190

Asn Arg Trp Trp Glu Glu Ile Ser Asp Arg Pro Ser Trp Lys Lys Leu
        195                 200                 205

Met Val Leu Ala Gly His
    210

<210> SEQ ID NO 54
<211> LENGTH: 232
```

<212> TYPE: PRT
<213> ORGANISM: Petunia x hybrida

<400> SEQUENCE: 54

```
Met Val Val Lys Val His Gly Ser Ala Met Ala Ala Cys Pro Gln Arg
1               5                   10                  15

Val Met Val Cys Leu Ile Glu Leu Gly Val Asp Phe Glu Leu Ile His
                20                  25                  30

Val Asp Leu Asp Ser Leu Glu Gln Lys Lys Pro Glu Phe Leu Val Leu
            35                  40                  45

Gln Pro Phe Gly Gln Val Pro Val Ile Glu Asp Gly Asp Phe Arg Leu
        50                  55                  60

Phe Glu Ser Arg Ala Ile Ile Arg Tyr Tyr Ala Ala Lys Tyr Glu Val
65                  70                  75                  80

Lys Gly Ser Lys Leu Thr Gly Thr Thr Leu Glu Glu Lys Ala Leu Val
                85                  90                  95

Asp Gln Trp Leu Glu Val Glu Ser Asn Asn Tyr Asn Asp Leu Val Tyr
                100                 105                 110

Asn Met Val Leu Gln Leu Leu Val Phe Pro Lys Met Gly Gln Thr Ser
            115                 120                 125

Asp Leu Thr Leu Val Thr Lys Cys Ala Asn Lys Leu Glu Asn Val Phe
        130                 135                 140

Asp Ile Tyr Glu Gln Arg Leu Ser Lys Ser Lys Tyr Leu Ala Gly Glu
145                 150                 155                 160

Phe Phe Ser Leu Ala Asp Leu Ser His Leu Pro Ser Leu Arg Phe Leu
                165                 170                 175

Met Asn Glu Gly Gly Phe Ser His Leu Val Thr Lys Arg Lys Cys Leu
                180                 185                 190

His Glu Trp Tyr Leu Asp Ile Ser Ser Arg Asp Ser Trp Lys Lys Val
            195                 200                 205

Leu Asp Leu Met Met Lys Lys Ile Ser Glu Ile Glu Ala Val Ser Ile
        210                 215                 220

Pro Ala Lys Glu Glu Ala Lys Val
225                 230
```

<210> SEQ ID NO 55
<211> LENGTH: 213
<212> TYPE: PRT
<213> ORGANISM: Cyclamen persicum x Cyclamen purpurascens

<400> SEQUENCE: 55

```
Met Val Val Lys Val Tyr Gly Pro Ala Thr Ala Gly Cys Pro Gln Arg
1               5                   10                  15

Val Ile Ala Cys Leu Phe Glu Leu Asp Val Asp Phe Glu Ile Ile His
                20                  25                  30

Val Asp Leu Glu Ser Gly Glu His Lys Lys Pro Asp Phe Leu Leu Arg
            35                  40                  45

Gln Pro Phe Gly Gln Val Pro Ala Ile Glu Asp Gly Asp Phe Arg Leu
        50                  55                  60

Phe Glu Ser Arg Ala Ile Met Arg Tyr Tyr Ala Ala Lys Tyr Ser Glu
65                  70                  75                  80

Lys Asn Pro Asp Leu Gln Gly Ser Thr Leu Glu Glu Lys Ala Leu Val
                85                  90                  95

Asp Gln Trp Leu Glu Val Glu Ser His Asn Phe Asn Asp Leu Val Tyr
                100                 105                 110
```

```
Thr Leu Val Leu His Leu Met Val Phe Pro Gln Met Gly Lys Arg Ser
            115                 120                 125

Asp Met Gln Leu Val Gln Glu Cys Glu Ser Lys Leu Glu Lys Val Phe
    130                 135                 140

Asp Ile Tyr Glu Glu Arg Leu Ser Lys Ser Asn Tyr Leu Ala Gly Lys
145                 150                 155                 160

Leu Phe Thr Leu Ala Asp Leu Ser His Leu Pro Ser Ile Thr Phe Leu
                165                 170                 175

Met Gly Glu Gly Gly Leu Gly His Met Val Arg Asn Arg Lys Asn Val
            180                 185                 190

Asn Ser Trp Trp Met Asp Ile Ser Ser Arg Pro Ser Trp Lys Lys Val
        195                 200                 205

Arg Lys Leu Met Asp
    210

<210> SEQ ID NO 56
<211> LENGTH: 213
<212> TYPE: PRT
<213> ORGANISM: Vitis vinifera

<400> SEQUENCE: 56

Met Val Met Lys Val Tyr Gly Pro Val Arg Ala Ala Cys Pro Gln Arg
1               5                   10                  15

Val Leu Ala Cys Leu Val Glu Lys Gly Val Glu Phe Glu Val Val His
            20                  25                  30

Val Asp Leu Asp Ser Gly Glu Gln Lys Arg Pro Asp Phe Leu Leu Arg
        35                  40                  45

Gln Pro Phe Gly Gln Val Pro Val Val Glu Asp Gly Asp Phe Arg Leu
    50                  55                  60

Phe Glu Ser Arg Ala Ile Val Arg Tyr Ile Ala Ala Lys Tyr Ala Glu
65                  70                  75                  80

Gln Gly Pro Asp Leu Leu Gly Lys Ser Leu Glu Glu Lys Ala Val Val
            85                  90                  95

Asp Gln Trp Leu Glu Val Glu Ala His Asn Phe Asn Glu Leu Val Tyr
        100                 105                 110

Thr Leu Val Met Gln Leu Val Ile Leu Pro Arg Met Gly Glu Arg Gly
    115                 120                 125

Asp Leu Ala Leu Ala His Thr Cys Glu Gln Lys Leu Glu Lys Val Phe
130                 135                 140

Asp Val Tyr Glu Gln Arg Leu Ser Lys Ser Arg Tyr Leu Ala Gly Asp
145                 150                 155                 160

Ser Phe Thr Leu Ala Asp Leu Ser His Leu Pro Ala Ile Arg Tyr Leu
                165                 170                 175

Val Lys Glu Ala Gly Met Ala His Leu Val Thr Glu Arg Lys Ser Val
            180                 185                 190

Ser Ala Trp Trp Glu Asp Ile Ser Asn Arg Ala Ala Trp Lys Lys Val
        195                 200                 205

Met Glu Leu Ala Ala
    210

<210> SEQ ID NO 57
<211> LENGTH: 214
<212> TYPE: PRT
<213> ORGANISM: Litchi chinensis

<400> SEQUENCE: 57
```

```
Met Val Val Lys Val Tyr Gly Pro Val Thr Ala Gly Cys Pro Gln Arg
1               5                   10                  15

Val Met Thr Cys Leu Leu Glu Lys Asp Val Glu Phe Glu Ile Ile His
            20                  25                  30

Val Asn Ile Asp Asn Gly Glu His Lys Arg Pro Glu Phe Leu Leu Arg
        35                  40                  45

Gln Pro Phe Gly Gln Val Pro Val Ile Glu Asp Asp Phe Lys Leu
    50                  55                  60

Phe Glu Ser Arg Ala Ile Leu Arg Tyr Tyr Ala Lys Tyr Ala Asp
65                  70                  75                  80

Arg Gly Pro Asn Leu Leu Gly Thr Thr Leu Glu Glu Arg Ala Arg Val
                85                  90                  95

Asp Gln Trp Leu Glu Val Glu Ala His Asn Phe Asn Asp Leu Ile Tyr
            100                 105                 110

Thr Met Val Leu Gln Leu Ile Val Ile Pro Ser Met Gly Gln Pro Gly
            115                 120                 125

Asp Leu Thr Leu Val His Ser Cys Glu Gln Lys Leu Glu Ala Val Phe
        130                 135                 140

Asp Val Tyr Glu Lys Gln Leu Ser Lys Ser Lys Tyr Leu Ala Gly Asp
145                 150                 155                 160

Trp Phe Ser Leu Ala Asp Leu Ser His Met Pro Ala Leu Arg Phe Leu
            165                 170                 175

Met Glu Asp Ala Lys Leu Val His Leu Val Lys Glu Arg Lys His Val
            180                 185                 190

Asn Ala Trp Trp Glu Glu Ile Ser Gly Arg Leu Ser Trp Lys Lys Leu
            195                 200                 205

Met Lys Leu Ala Tyr Tyr
    210

<210> SEQ ID NO 58
<211> LENGTH: 215
<212> TYPE: PRT
<213> ORGANISM: Prunus persica

<400> SEQUENCE: 58

Met Val Val Lys Val Tyr Gly Pro Val Lys Ala Ala Cys Pro Gln Arg
1               5                   10                  15

Val Met Val Cys Leu Leu Glu Lys Gly Val Asn Phe Glu Ile Val Asp
            20                  25                  30

Val Asn Leu Glu Val Gly Glu Gln Lys Gln Pro Gln Phe Leu Ser Arg
        35                  40                  45

Gln Pro Phe Gly Gln Val Pro Ala Val Glu Asp Gly Asp Phe Arg Leu
    50                  55                  60

Phe Glu Ser Arg Ala Ile Ile Arg Tyr Tyr Ala Lys Tyr Ala Asp
65                  70                  75                  80

Arg Gly Pro Asn Leu Leu Gly Thr Thr Leu Glu Glu Lys Ala Leu Val
                85                  90                  95

Asp Gln Trp Leu Glu Val Glu Ala His Asn Phe Asn Asp Leu Val Tyr
            100                 105                 110

Thr Leu Val Leu Gln Leu Leu Val Leu Pro Arg Met Gly Glu Arg Gly
            115                 120                 125

Asp Val Ala Leu Val His Ala Cys Glu Glu Lys Leu Glu Lys Val Phe
        130                 135                 140

Asp Val Tyr Glu Glu Arg Leu Ser Lys Ser Ser Tyr Leu Ala Gly Glu
145                 150                 155                 160
```

```
Ala Phe Thr Leu Ala Asp Leu Ser His Leu Pro Gly Ile Ser Tyr Leu
            165                 170                 175

Ile Asp Glu Ala Lys Leu Gly His Leu Val Ser Glu Arg Lys Asn Val
        180                 185                 190

Asn Ala Trp Trp Lys Asp Ile Ser Asn Arg Pro Ala Trp Lys Lys Leu
        195                 200                 205

Met Ser Leu Ala Ser Asp Tyr
    210                 215

<210> SEQ ID NO 59
<211> LENGTH: 216
<212> TYPE: PRT
<213> ORGANISM: Prunus persica

<400> SEQUENCE: 59

Met Val Val Lys Val Tyr Gly Pro Val Lys Ala Ala Cys Pro Gln Arg
1               5                   10                  15

Val Met Val Cys Leu Leu Glu Lys Gly Val Asn Phe Glu Ile Val Asp
            20                  25                  30

Val Asn Leu Glu Val Gly Glu Gln Lys Gln Pro Gln Phe Leu Ser Arg
        35                  40                  45

Gln Pro Phe Gly Gln Val Pro Ala Val Glu Asp Gly Asp Phe Arg Leu
    50                  55                  60

Phe Glu Ser Arg Ala Ile Ile Arg Tyr Tyr Ala Ala Lys Tyr Ala Asp
65                  70                  75                  80

Arg Gly Pro Asn Leu Leu Gly Thr Thr Leu Glu Glu Lys Ala Leu Val
            85                  90                  95

Asp Gln Trp Leu Glu Val Glu Ala His Asn Phe Asn Asp Leu Val Tyr
        100                 105                 110

Thr Leu Val Leu Gln Leu Leu Val Leu Pro Asp Arg Met Gly Glu Arg
    115                 120                 125

Gly Asp Val Ala Leu Val His Ala Cys Glu Glu Lys Leu Glu Lys Val
    130                 135                 140

Phe Asp Val Tyr Glu Glu Arg Leu Ser Lys Ser Ser Tyr Leu Ala Gly
145                 150                 155                 160

Glu Ala Phe Thr Leu Ala Asp Leu Ser His Leu Pro Gly Ile Ser Tyr
            165                 170                 175

Leu Ile Asp Glu Ala Lys Leu Gly His Leu Val Ser Glu Arg Lys Asn
        180                 185                 190

Val Asn Ala Trp Trp Lys Asp Ile Ser Asn Arg Pro Ala Trp Lys Lys
        195                 200                 205

Leu Met Ser Leu Ala Ser Asp Tyr
    210                 215

<210> SEQ ID NO 60
<211> LENGTH: 20
<212> TYPE: DNA
<213> ORGANISM: artificial
<220> FEATURE:
<223> OTHER INFORMATION: amplification primer

<400> SEQUENCE: 60
tggcctgcct tttagagaaa                                               20

<210> SEQ ID NO 61
<211> LENGTH: 2351
<212> TYPE: DNA
```

<213> ORGANISM: Euphorbia pulcherrima

<400> SEQUENCE: 61

```
aaaactctat aacaaacaag aaatcaaggc taaaaaaatg gtagtgaaag tgtatggagc      60
agctcaggca gcttgcccac aaagagtaat ggcctgcctt ttagagaaag atattccttt     120
tgatcttgtt catgttgatc ttccttctgc tcaacataaa ctctcttcct tccttctcaa     180
acaggttctt tacttccctt tttttactat acatttcttc taggcctaat atacatctag     240
accccctata gttgttcctg aaacccctc agcccctga acttgttaaa gtggatctta      300
cagcccctta aacttggtca aactgaacct caaaacccct taatggtaac atgcccagtt     360
ttgttccggt aaatcagttt tcgattcaat ctttgacgaa acaatcttag attcaatctt     420
tagaaaaata atacttgaca tatcagcatc aagcggctat ggggttcact tttaacaagt     480
tcagggtgct ataaagtcca ctttaataaa ttcagggtta aggatacctt ttgtaagttt     540
aggtggttga ggggttttaa gggaactata ggaggcctag atttattagc tctcttgttt     600
gatgtcacaa ttaattatgt ttatttattt attctgtagc cctttgggtt agttccagct     660
atagaagatg gggatttcag gcttttggt atgtttctta atcttttcat ttcagtgata      720
gccctcagta tttcgtttta ctaagatttc gggaccacaa ttcgttttg tagtgtcact      780
atggataatt gttaaaaatg agacatgtac aaaacaaatc ctattcgaat cttctatcgt     840
tggtcataac cacatggata tctacgcata aaaataccaa aaaatatttt aacatgtaca     900
tgttcttttg tattccgtcc actatttcga taagcatcga tttatcgttt tttggcttta     960
aattataatg gactaaacta aaatgattca ttaaactgtc tgaacttctt tattgtgaaa    1020
tcacggatag ctgttgcaac tccacttcag ggtcaattgg aaacaacatc tctgtaatta    1080
catgggtaag gctgcataca ctcaaccccc cgacactgct tgtgagggag ccttattagg    1140
cattggggtg atgttgttgt tttacacgtt attttgtatc attgtaatct atcaaactat    1200
tataattact tattaccaag tataattat tacattgatt aaagtataat ttattccact     1260
aaatttatgt tttatgcacc ttaccctgaa ctttgatttt ttatttagta ttataaaatg    1320
ttgtttaagt aaataaaata gatactattt aaaaataatt tagaaaaaaa taataaaata    1380
gagcaaggtc tccatacaaa accatcgtac ttatttgaac agatatatat gtagtgttat    1440
tcatatttt ttttataata acatagaact gatgaatctg gattagaaat gatgatataa     1500
tggcttgcct cattcacgat cacacaattg ataagtctga ttttaccaac aaatatcagt    1560
ttttcaatat tatgtgttgc tattttcttg aagaagaaat tttgcacgac catatttaag    1620
aataggctta gattgatcgg tcaaacaaaa tcttaggtta ttttttcatt ttcctttct     1680
cattagttag aatcaaaatt tggaattaaa ttttttgttt taattttact tctaactatt    1740
gagatcatat atcaccaaat atatgctttc tttattattt ctacataaaa aaatatatgg    1800
ttttacaact acctaactat gcttttttt aaagtttgcc tcattaggct tacaactacc     1860
aaactatgtt gaattaatat aattttgttt gtgtgtgtga agaatcaaga gccataatga    1920
gatactatgc aacaaaatat gaagaaagag ggcccaattt gttaggaaaa acattagaag    1980
agaaagcaat agttgatcaa tgggttgaag tggaagccca taatttcaat aatttggttt    2040
acaatattgt aattgaagtt ttgataaagc caaaatggg ggaacaaggt gacatcaaca     2100
tagtcaaaag ctgtgaacat aagctggata aagtgttcga tgtgtacgag gaaaggctat    2160
ccagttccaa atatcttgga ggagattatt tcacacttgc tgatttaacc catatgcctt    2220
ccattaggta ccttgttcat gagcttgggt tagcccattt ggttcacaat agaaacaagg    2280
```

```
tcaatgcttg gtggattgat atatcggacc gaccggcttg gaaaaatttg atgattcttg    2340
ctggttatta g                                                        2351
```

<210> SEQ ID NO 62
<211> LENGTH: 214
<212> TYPE: PRT
<213> ORGANISM: Artificial Sequence
<220> FEATURE:
<223> OTHER INFORMATION: EpGST variant
<220> FEATURE:
<221> NAME/KEY: MISC_FEATURE
<222> LOCATION: (12)..(12)
<223> OTHER INFORMATION: Xaa is Ala or Gly
<220> FEATURE:
<221> NAME/KEY: MISC_FEATURE
<222> LOCATION: (13)..(13)
<223> OTHER INFORMATION: Xaa is Cys or Asn
<220> FEATURE:
<221> NAME/KEY: MISC_FEATURE
<222> LOCATION: (53)..(53)
<223> OTHER INFORMATION: Xaa is Leu or Gln
<220> FEATURE:
<221> NAME/KEY: MISC_FEATURE
<222> LOCATION: (54)..(54)
<223> OTHER INFORMATION: Xaa is Val or Pro
<220> FEATURE:
<221> NAME/KEY: MISC_FEATURE
<222> LOCATION: (55)..(55)
<223> OTHER INFORMATION: Xaa is Pro or Val
<220> FEATURE:
<221> NAME/KEY: MISC_FEATURE
<222> LOCATION: (56)..(56)
<223> OTHER INFORMATION: Xaa is Ala or Pro

<400> SEQUENCE: 62

```
Met Val Val Lys Val Tyr Gly Ala Ala Gln Ala Xaa Xaa Pro Gln Arg
1               5                   10                  15

Val Met Ala Cys Leu Leu Glu Lys Asp Ile Pro Phe Asp Leu Val His
                20                  25                  30

Val Asp Leu Pro Ser Ala Gln His Lys Leu Ser Ser Phe Leu Leu Lys
            35                  40                  45

Gln Pro Phe Gly Xaa Xaa Xaa Xaa Ile Glu Asp Gly Asp Phe Arg Leu
        50                  55                  60

Phe Glu Ser Arg Ala Ile Met Arg Tyr Tyr Ala Thr Lys Tyr Glu Glu
65                  70                  75                  80

Arg Gly Pro Asn Leu Leu Gly Lys Thr Leu Glu Glu Lys Ala Ile Val
                85                  90                  95

Asp Gln Trp Val Glu Val Glu Ala His Asn Phe Asn Asn Leu Val Tyr
            100                 105                 110

Asn Ile Val Ile Glu Val Leu Ile Lys Pro Lys Met Gly Glu Gln Gly
        115                 120                 125

Asp Ile Asn Ile Val Lys Ser Cys Glu His Lys Leu Asp Lys Val Phe
130                 135                 140

Asp Val Tyr Glu Glu Arg Leu Ser Ser Lys Tyr Leu Gly Gly Asp
145                 150                 155                 160

Tyr Phe Thr Leu Ala Asp Leu Thr His Met Pro Ser Ile Arg Tyr Leu
                165                 170                 175

Val His Glu Leu Gly Leu Ala His Leu Val His Asn Arg Asn Lys Val
            180                 185                 190

Asn Ala Trp Trp Ile Asp Ile Ser Asp Arg Pro Ala Trp Lys Asn Leu
        195                 200                 205

Met Ile Leu Ala Gly Tyr
```

<210> SEQ ID NO 63
<211> LENGTH: 214
<212> TYPE: PRT
<213> ORGANISM: Artificial Sequence
<220> FEATURE:
<223> OTHER INFORMATION: EpGST variant domain

<400> SEQUENCE: 63

```
Met Val Val Lys Val Tyr Gly Ala Ala Gln Ala Ala Cys Pro Gln Arg
1               5                   10                  15

Val Met Ala Cys Leu Leu Glu Lys Asp Ile Pro Phe Asp Leu Val His
            20                  25                  30

Val Asp Leu Pro Ser Ala Gln His Lys Leu Ser Ser Phe Leu Leu Lys
        35                  40                  45

Gln Pro Phe Gly Gln Val Pro Ala Ile Glu Asp Gly Asp Phe Arg Leu
    50                  55                  60

Phe Glu Ser Arg Ala Ile Met Arg Tyr Tyr Ala Thr Lys Tyr Glu Glu
65                  70                  75                  80

Arg Gly Pro Asn Leu Leu Gly Lys Thr Leu Glu Glu Lys Ala Ile Val
                85                  90                  95

Asp Gln Trp Val Glu Val Glu Ala His Asn Phe Asn Asn Leu Val Tyr
            100                 105                 110

Asn Ile Val Ile Glu Val Leu Ile Lys Pro Lys Met Gly Glu Gln Gly
        115                 120                 125

Asp Ile Asn Ile Val Lys Ser Cys Glu His Lys Leu Asp Lys Val Phe
    130                 135                 140

Asp Val Tyr Glu Glu Arg Leu Ser Ser Ser Lys Tyr Leu Gly Gly Asp
145                 150                 155                 160

Tyr Phe Thr Leu Ala Asp Leu Thr His Met Pro Ser Ile Arg Tyr Leu
                165                 170                 175

Val His Glu Leu Gly Leu Ala His Leu Val His Asn Arg Asn Lys Val
            180                 185                 190

Asn Ala Trp Trp Ile Asp Ile Ser Asp Arg Pro Ala Trp Lys Asn Leu
        195                 200                 205

Met Ile Leu Ala Gly Tyr
    210
```

<210> SEQ ID NO 64
<211> LENGTH: 214
<212> TYPE: PRT
<213> ORGANISM: Artificial Sequence
<220> FEATURE:
<223> OTHER INFORMATION: EpGST variant domain

<400> SEQUENCE: 64

```
Met Val Val Lys Val Tyr Gly Ala Ala Gln Ala Ala Cys Pro Gln Arg
1               5                   10                  15

Val Met Ala Cys Leu Leu Glu Lys Asp Ile Pro Phe Asp Leu Val His
            20                  25                  30

Val Asp Leu Pro Ser Ala Gln His Lys Leu Ser Ser Phe Leu Leu Lys
        35                  40                  45

Gln Pro Phe Gly Gln Pro Val Pro Ile Glu Asp Gly Asp Phe Arg Leu
    50                  55                  60

Phe Glu Ser Arg Ala Ile Met Arg Tyr Tyr Ala Thr Lys Tyr Glu Glu
65                  70                  75                  80
```

```
Arg Gly Pro Asn Leu Leu Gly Lys Thr Leu Glu Glu Lys Ala Ile Val
            85              90              95

Asp Gln Trp Val Glu Val Glu Ala His Asn Phe Asn Asn Leu Val Tyr
            100             105             110

Asn Ile Val Ile Glu Val Leu Ile Lys Pro Lys Met Gly Glu Gln Gly
            115             120             125

Asp Ile Asn Ile Val Lys Ser Cys Glu His Lys Leu Asp Lys Val Phe
            130             135             140

Asp Val Tyr Glu Glu Arg Leu Ser Ser Ser Lys Tyr Leu Gly Gly Asp
145             150             155             160

Tyr Phe Thr Leu Ala Asp Leu Thr His Met Pro Ser Ile Arg Tyr Leu
                165             170             175

Val His Glu Leu Gly Leu Ala His Leu Val His Asn Arg Asn Lys Val
                180             185             190

Asn Ala Trp Trp Ile Asp Ile Ser Asp Arg Pro Ala Trp Lys Asn Leu
                195             200             205

Met Ile Leu Ala Gly Tyr
210
```